United States Patent
Hatch

(10) Patent No.: US 10,822,596 B2
(45) Date of Patent: Nov. 3, 2020

(54) COMPOSITIONS AND METHODS FOR TREATING CRANIOSYNOSTOSIS

(71) Applicant: Alexion Pharmaceuticals, Inc., Boston, MA (US)

(72) Inventor: Nan Hatch, Ann Arbor, MI (US)

(73) Assignee: Alexion Pharmaceuticals, Inc., Boston, MA (US)

( * ) Notice: Subject to any disclaimer, the term of this patent is extended or adjusted under 35 U.S.C. 154(b) by 163 days.

(21) Appl. No.: 15/325,369

(22) PCT Filed: Jul. 10, 2015

(86) PCT No.: PCT/US2015/039973
§ 371 (c)(1),
(2) Date: Jan. 10, 2017

(87) PCT Pub. No.: WO2016/007873
PCT Pub. Date: Jan. 14, 2016

(65) Prior Publication Data
US 2017/0175094 A1    Jun. 22, 2017

Related U.S. Application Data

(60) Provisional application No. 62/158,964, filed on May 8, 2015, provisional application No. 62/023,620, filed on Jul. 11, 2014.

(51) Int. Cl.
| | | |
|---|---|---|
| *C12N 9/16* | (2006.01) | |
| *A61K 48/00* | (2006.01) | |
| *C12N 9/00* | (2006.01) | |
| *A61K 38/46* | (2006.01) | |
| *A61K 38/00* | (2006.01) | |

(52) U.S. Cl.
CPC ............. *C12N 9/16* (2013.01); *A61K 38/465* (2013.01); *A61K 48/00* (2013.01); *C12N 9/00* (2013.01); *C12Y 301/03001* (2013.01); *A61K 38/00* (2013.01); *C07K 2319/00* (2013.01)

(58) Field of Classification Search
None
See application file for complete search history.

(56) References Cited

U.S. PATENT DOCUMENTS

| | | |
|---|---|---|
| 5,336,759 A | 8/1994 | Matsuo et al. |
| 5,338,830 A | 8/1994 | Matsuo et al. |
| 5,340,920 A | 8/1994 | Matsuo et al. |
| 5,352,770 A | 10/1994 | Matsuo |
| 5,428,130 A | 6/1995 | Capon et al. |
| 5,434,133 A | 7/1995 | Tanaka et al. |
| 5,583,108 A | 12/1996 | Wei et al. |
| 5,665,704 A | 9/1997 | Lowe et al. |
| 5,714,147 A | 2/1998 | Capon et al. |
| 5,767,239 A | 6/1998 | Immer et al. |
| 5,846,932 A | 12/1998 | Lowe et al. |
| 5,948,761 A | 9/1999 | Seilhamer et al. |
| 5,973,134 A | 10/1999 | Matsuo et al. |
| 6,020,168 A | 2/2000 | Matsuo et al. |
| 6,028,055 A | 2/2000 | Lowe et al. |
| 6,034,231 A | 3/2000 | Tanaka et al. |
| 6,290,952 B1 | 9/2001 | Poelstra et al. |
| 6,406,697 B1 | 6/2002 | Capon et al. |
| 6,407,211 B1 | 6/2002 | Burnett, Jr. et al. |
| 6,420,384 B2 | 7/2002 | Weigele et al. |
| 6,436,386 B1 | 8/2002 | Roberts et al. |
| 6,455,495 B1 | 9/2002 | Orgel et al. |
| 6,458,579 B2 | 10/2002 | Hopwood et al. |
| 6,525,022 B1 | 2/2003 | Lowe et al. |
| 6,541,610 B1 | 4/2003 | Smith |
| 6,743,425 B2 | 6/2004 | Nakao |
| 6,790,649 B1 | 9/2004 | Crine et al. |
| 6,818,619 B2 | 11/2004 | Burnett, Jr. et al. |
| 6,830,885 B1 | 12/2004 | Lanctot et al. |
| 6,849,714 B1 | 2/2005 | Bridon et al. |
| 6,887,470 B1 | 5/2005 | Bridon et al. |
| 6,905,689 B2 | 6/2005 | Schneidinger et al. |
| 6,946,484 B2 | 9/2005 | Adams et al. |
| 7,026,293 B2 | 4/2006 | Kitakaze |
| 7,033,997 B2 | 4/2006 | Forssmann et al. |
| 7,070,974 B1 | 7/2006 | Desgroseillers et al. |
| 7,105,539 B2 | 9/2006 | Gravel et al. |
| 7,179,903 B2 | 2/2007 | McArthur et al. |
| 7,256,253 B2 | 8/2007 | Bridon et al. |
| 7,271,149 B2 | 9/2007 | Glaesner et al. |
| 7,276,481 B2 | 10/2007 | Golembo et al. |
| 7,341,838 B2 | 3/2008 | Buechler et al. |
| 7,365,091 B2 | 4/2008 | Gravel et al. |

(Continued)

FOREIGN PATENT DOCUMENTS

| | | |
|---|---|---|
| EP | 0478797 B1 | 4/1995 |
| EP | 0769554 A2 | 4/1997 |

(Continued)

OTHER PUBLICATIONS

Mornet, Orphanet Journal of Rare Diseases, 2007, 2: 1-8.*
Sequence alignment, 2018.*
Rocco et al., Archives de Pédiatrie, 2017, 24: 5589-5592.*
Appeal Brief as Filed in U.S. Appl. No. 12/638,527, mailed Oct. 9, 2015 (101 pages).
Reply Brief as Filed in U.S. Appl. No. 12/638,527, mailed Apr. 22, 2016 (4 pages).
Examiner's Answer to Appeal Brief for U.S. Appl. No. 12/638,527, mailed Feb. 23, 2016 (9 pages).
Phillips et al., "Significantly improved muscle strength, running speed, and agility in children with hypophosphatasia treated with asfotase alfa," Endocrine Society's 97th Annual Meeting and Expo, Mar. 5-8, San Diego, CA. Abstract OR29-4 (2015) (2 pages).

(Continued)

*Primary Examiner* — Ileana Popa
(74) *Attorney, Agent, or Firm* — Clark & Elbing LLP

(57) ABSTRACT

Provided herein are compositions and methods for treating craniosynostosis. In particular, provided herein are methods of treating and preventing craniosynostosis by administering an isolated TNAP polypeptide or a nucleic acid molecule that encodes a TNAP polypeptide.

13 Claims, 23 Drawing Sheets

Specification includes a Sequence Listing.

(56) References Cited

U.S. PATENT DOCUMENTS

| | | |
|---|---|---|
| 7,384,917 B2 | 6/2008 | Burnett, Jr. et al. |
| 7,399,466 B2 | 7/2008 | Boileau |
| 7,414,107 B2 | 8/2008 | Larsen |
| 7,425,531 B2 | 9/2008 | Lanctot et al. |
| 7,427,498 B2 | 9/2008 | Crine et al. |
| 7,470,668 B2 | 12/2008 | Lanctot et al. |
| 7,488,713 B2 | 2/2009 | Vesely |
| 7,527,939 B2 | 5/2009 | Davey et al. |
| 7,563,769 B2 | 7/2009 | Bogin et al. |
| 7,625,564 B2 | 12/2009 | Wang et al. |
| 7,642,243 B2 | 1/2010 | Nakao et al. |
| 7,648,962 B2 | 1/2010 | James et al. |
| 7,662,773 B2 | 2/2010 | James et al. |
| 7,678,391 B2 | 3/2010 | Graham et al. |
| 7,732,406 B2 | 6/2010 | Mitrovic et al. |
| 7,736,653 B2 | 6/2010 | Kim et al. |
| 7,754,852 B2 | 7/2010 | Burnett, Jr. et al. |
| 7,763,712 B2 | 7/2010 | Crine et al. |
| 7,803,769 B2 | 9/2010 | Sullivan et al. |
| 7,803,901 B2 | 9/2010 | Burnett, Jr. et al. |
| 7,825,092 B2 | 11/2010 | Vesely |
| 7,846,900 B2 | 12/2010 | Vesely |
| 7,858,560 B2 | 12/2010 | Koster et al. |
| 7,919,591 B2 | 4/2011 | Sheffer et al. |
| 7,943,126 B2 | 5/2011 | Tomatsu et al. |
| 7,960,529 B2 | 6/2011 | Crine et al. |
| 8,058,242 B2 | 11/2011 | Alewood et al. |
| 8,691,208 B2 | 4/2014 | Tomatsu et al. |
| 9,266,939 B2 | 2/2016 | Crine et al. |
| 9,988,620 B2 | 6/2018 | Crine et al. |
| 10,000,532 B2 | 6/2018 | Crine et al. |
| 2002/0183276 A1 | 12/2002 | Millan et al. |
| 2003/0158132 A1 | 8/2003 | Kovesdi |
| 2004/0023916 A1 | 2/2004 | Millan et al. |
| 2004/0077537 A1 | 4/2004 | Schreiner |
| 2004/0234518 A1 | 11/2004 | Crine et al. |
| 2005/0113286 A1 | 5/2005 | Schreiner et al. |
| 2005/0142217 A1 | 6/2005 | Adams et al. |
| 2005/0202442 A1 | 9/2005 | Morris et al. |
| 2005/0244904 A1 | 11/2005 | Ng |
| 2005/0276796 A1 | 12/2005 | Tomatsu et al. |
| 2006/0014687 A1 | 1/2006 | Crine et al. |
| 2006/0019890 A1 | 1/2006 | Kapoun et al. |
| 2006/0074009 A1 | 4/2006 | James et al. |
| 2006/0110359 A1 | 5/2006 | Sanchez-Ramos et al. |
| 2006/0172929 A1 | 8/2006 | Rappold-Hoerbrand et al. |
| 2006/0228710 A1 | 10/2006 | Morris et al. |
| 2007/0041972 A1 | 2/2007 | Rother et al. |
| 2007/0042957 A1 | 2/2007 | Burnett et al. |
| 2007/0081984 A1 | 4/2007 | Tomatsu et al. |
| 2007/0081986 A1 | 4/2007 | Tomatsu et al. |
| 2007/0197434 A1 | 8/2007 | Nakao et al. |
| 2007/0281887 A1 | 12/2007 | Pan |
| 2007/0292966 A1 | 12/2007 | Prickett et al. |
| 2007/0293418 A1 | 12/2007 | Larsen |
| 2008/0032933 A1 | 2/2008 | Burnett et al. |
| 2008/0081768 A1 | 4/2008 | Watt et al. |
| 2008/0085862 A1 | 4/2008 | Kim et al. |
| 2008/0113411 A1 | 5/2008 | Sheffer et al. |
| 2008/0113412 A1 | 5/2008 | Sheffer et al. |
| 2008/0125574 A1 | 5/2008 | Sheffer et al. |
| 2008/0153747 A1 | 6/2008 | Alewood et al. |
| 2008/0161243 A1 | 7/2008 | Rosen et al. |
| 2008/0181903 A1 | 7/2008 | Bhaskar et al. |
| 2008/0182299 A1 | 7/2008 | Colocaru et al. |
| 2008/0194481 A1 | 8/2008 | Rosen et al. |
| 2008/0194682 A1 | 8/2008 | Golembo et al. |
| 2008/0227713 A1 | 9/2008 | Protter |
| 2008/0293632 A1 | 11/2008 | Rappold-Hoerbrand et al. |
| 2008/0312142 A1 | 12/2008 | Nakao et al. |
| 2009/0011997 A1 | 1/2009 | Peri et al. |
| 2009/0023652 A1 | 1/2009 | Bell et al. |
| 2009/0053192 A1 | 2/2009 | Millan et al. |
| 2009/0069243 A1 | 3/2009 | Burnett, Jr. et al. |
| 2009/0092582 A1 | 4/2009 | Bogin et al. |
| 2009/0142347 A1 | 6/2009 | Millan |
| 2009/0170756 A1 | 7/2009 | Burnett, Jr. et al. |
| 2009/0221803 A1 | 9/2009 | Dall'Acqua et al. |
| 2009/0238814 A1 | 9/2009 | Tomatsu et al. |
| 2009/0240031 A1 | 9/2009 | Immer et al. |
| 2009/0247462 A1 | 10/2009 | Bogin et al. |
| 2009/0252729 A1 | 10/2009 | Farrington et al. |
| 2009/0258018 A1 | 10/2009 | Medich et al. |
| 2009/0275506 A1 | 11/2009 | Bakis et al. |
| 2009/0325195 A1 | 12/2009 | Davey et al. |
| 2010/0008979 A1 | 1/2010 | Tomatsu et al. |
| 2010/0055150 A1 | 3/2010 | Golembo et al. |
| 2010/0093678 A1 | 4/2010 | Della-Fera et al. |
| 2010/0160212 A1 | 6/2010 | Sheffer et al. |
| 2010/0168443 A1 | 7/2010 | Geysen |
| 2010/0184680 A1 | 7/2010 | Bevec |
| 2010/0197574 A1 | 8/2010 | Chen et al. |
| 2010/0204094 A1 | 8/2010 | Simari et al. |
| 2010/0204109 A1 | 8/2010 | Bevec |
| 2010/0204446 A1 | 8/2010 | Forssmann |
| 2010/0209958 A1 | 8/2010 | Nakao et al. |
| 2010/0216714 A1 | 8/2010 | James et al. |
| 2010/0221234 A1 | 9/2010 | Crine et al. |
| 2010/0240125 A1 | 9/2010 | Crine et al. |
| 2010/0249017 A1 | 9/2010 | Bevec et al. |
| 2010/0260706 A1 | 10/2010 | Bogin et al. |
| 2010/0261248 A1 | 10/2010 | Kim et al. |
| 2010/0297021 A1 | 11/2010 | Wendt et al. |
| 2010/0297119 A1* | 11/2010 | Crine .................. C12N 9/16 424/134.1 |
| 2010/0305031 A1 | 12/2010 | Wakabayashi et al. |
| 2010/0305051 A1 | 12/2010 | Burnett, Jr. et al. |
| 2010/0310561 A1 | 12/2010 | Canada et al. |
| 2010/0311660 A1 | 12/2010 | Simari et al. |
| 2010/0317600 A1 | 12/2010 | Immer et al. |
| 2010/0331256 A1 | 12/2010 | Wendt et al. |
| 2011/0152194 A1 | 6/2011 | Burnett, Jr. et al. |
| 2011/0250187 A1 | 10/2011 | Tomatsu et al. |
| 2011/0269684 A1 | 11/2011 | Burnett, Jr. et al. |
| 2011/0300143 A1 | 12/2011 | Sly et al. |
| 2012/0088771 A1 | 4/2012 | Millan |
| 2012/0164142 A1 | 6/2012 | Crine et al. |
| 2013/0108635 A1 | 5/2013 | Crine et al. |
| 2013/0323244 A1 | 12/2013 | Crine et al. |
| 2014/0193388 A1 | 7/2014 | Velders et al. |
| 2014/0194484 A1 | 7/2014 | Coats et al. |
| 2015/0353633 A1 | 12/2015 | Kakkis et al. |
| 2016/0052968 A1 | 2/2016 | Crine et al. |
| 2016/0097100 A1 | 4/2016 | Trent et al. |
| 2017/0175094 A1 | 6/2017 | Hatch |
| 2017/0360899 A1 | 12/2017 | Marozsan et al. |
| 2018/0230445 A1 | 8/2018 | Jaluria et al. |

FOREIGN PATENT DOCUMENTS

| | | |
|---|---|---|
| EP | 0771875 B1 | 5/1997 |
| EP | 0466174 B1 | 6/1997 |
| EP | 0475394 B1 | 6/1997 |
| EP | 0466175 B1 | 1/1998 |
| EP | 0477971 B1 | 1/1998 |
| EP | 0475290 B1 | 12/1998 |
| EP | 0475291 B1 | 12/1998 |
| EP | 0497368 B1 | 6/2002 |
| EP | 1492567 | 9/2003 |
| EP | 1502604 A1 | 2/2005 |
| EP | 1623994 A2 | 2/2006 |
| EP | 1759001 | 3/2007 |
| EP | 1759710 A1 | 3/2007 |
| EP | 1985697 A1 | 10/2008 |
| EP | 2158319 B1 | 12/2011 |
| EP | 3250227 A2 | 12/2017 |
| JP | 8070875 | 3/1996 |
| JP | 2000-327583 A | 11/2000 |
| JP | 2002-541776 A2 | 12/2002 |
| JP | 2007-511209 A | 5/2007 |
| JP | 2010-501026 A | 1/2010 |
| JP | 2010-526543 A | 8/2010 |
| JP | 2010-530222 A | 9/2010 |
| JP | 2011-504506 A | 2/2011 |

(56) References Cited

FOREIGN PATENT DOCUMENTS

| WO | WO-92/20371 A1 | 11/1992 |
|---|---|---|
| WO | WO-95/05456 | 8/1994 |
| WO | WO-94/20534 A1 | 9/1994 |
| WO | WO-95/13296 A1 | 5/1995 |
| WO | WO-95/33769 A1 | 12/1995 |
| WO | WO-98/17690 A1 | 4/1998 |
| WO | WO-98/35703 A2 | 8/1998 |
| WO | WO-99/46283 A1 | 9/1999 |
| WO | WO-00/18954 A2 | 4/2000 |
| WO | WO-00/050580 A2 | 8/2000 |
| WO | WO-00/53755 A2 | 9/2000 |
| WO | WO-00/64486 A2 | 11/2000 |
| WO | WO-00/69900 A2 | 11/2000 |
| WO | WO-01/36620 A2 | 5/2001 |
| WO | WO-01/44284 A2 | 6/2001 |
| WO | WO-01/80890 A2 | 11/2001 |
| WO | WO-02/015918 A2 | 2/2002 |
| WO | WO-02/47871 A1 | 6/2002 |
| WO | WO-02/067639 A1 | 8/2002 |
| WO | WO-02/068579 A2 | 9/2002 |
| WO | WO-02/074234 A2 | 9/2002 |
| WO | WO-03/074082 A1 | 9/2003 |
| WO | WO-03/079979 A2 | 10/2003 |
| WO | WO-03/092581 A2 | 11/2003 |
| WO | WO-03/094835 A2 | 11/2003 |
| WO | WO-2004/011498 A2 | 2/2004 |
| WO | WO-2004/022579 A2 | 3/2004 |
| WO | WO-2004/046194 A2 | 6/2004 |
| WO | WO-2004/047871 A2 | 6/2004 |
| WO | WO-2004/062555 A2 | 7/2004 |
| WO | WO-2004/074320 A2 | 9/2004 |
| WO | WO-2004/094460 A2 | 11/2004 |
| WO | WO-2005/000095 A2 | 1/2005 |
| WO | WO-2005/007809 A2 | 1/2005 |
| WO | WO-2005/042034 A1 | 5/2005 |
| WO | WO-2005/047337 A1 | 5/2005 |
| WO | WO-2005/070446 A1 | 8/2005 |
| WO | WO-2005/072055 A2 | 8/2005 |
| WO | WO-2005/094890 A1 | 10/2005 |
| WO | WO-2005/098490 A1 | 10/2005 |
| WO | WO-2005/103263 A1 | 11/2005 |
| WO | WO-2005/110435 A1 | 11/2005 |
| WO | WO-2006/005140 A2 | 1/2006 |
| WO | WO-2006/026663 A1 | 3/2006 |
| WO | WO-2006/039480 A2 | 4/2006 |
| WO | WO-2006/060641 A2 | 6/2006 |
| WO | WO-2006/110743 A1 | 10/2006 |
| WO | WO-2006/116260 A2 | 11/2006 |
| WO | WO-2007/041645 A2 | 4/2007 |
| WO | WO-2007/071295 A1 | 6/2007 |
| WO | WO-2007/097923 A2 | 8/2007 |
| WO | WO-2007/130113 A2 | 11/2007 |
| WO | WO-2008/021872 A1 | 2/2008 |
| WO | WO-2008/030558 A2 | 3/2008 |
| WO | WO-2008/031045 A2 | 3/2008 |
| WO | WO-2008/053362 A2 | 5/2008 |
| WO | WO-2008/058016 A2 | 5/2008 |
| WO | WO-2008/079995 A2 | 7/2008 |
| WO | WO-2008/088422 A2 | 7/2008 |
| WO | WO-2008/109903 A1 | 9/2008 |
| WO | WO-2008/136611 A1 | 11/2008 |
| WO | WO-2008/138131 A1 | 11/2008 |
| WO | WO-2008/154226 A1 | 12/2008 |
| WO | WO-2009/006520 A1 | 1/2009 |
| WO | WO-2009/006732 A9 | 1/2009 |
| WO | WO-2009/015011 A1 | 1/2009 |
| WO | WO-2009/023270 A2 | 2/2009 |
| WO | WO-2009/033680 A2 | 3/2009 |
| WO | WO-2009/033724 A1 | 3/2009 |
| WO | WO-2009/033796 A1 | 3/2009 |
| WO | WO-2009/033807 A2 | 3/2009 |
| WO | WO-2009/034134 A2 | 3/2009 |
| WO | WO-2009/036448 A2 | 3/2009 |
| WO | WO-2009/040030 A1 | 4/2009 |
| WO | WO-2009/040031 A2 | 4/2009 |
| WO | WO-2009/040083 A2 | 4/2009 |
| WO | WO-2009/046861 A1 | 4/2009 |
| WO | WO-2009/058322 A1 | 5/2009 |
| WO | WO-2009/067639 A2 | 5/2009 |
| WO | WO-2009/086126 A2 | 7/2009 |
| WO | WO-2009/090553 A2 | 7/2009 |
| WO | WO-2009/142307 A1 | 11/2009 |
| WO | WO-2009/149161 A9 | 12/2009 |
| WO | WO-2009/156481 A1 | 12/2009 |
| WO | WO-2009/158035 A2 | 12/2009 |
| WO | WO-2010/002583 A2 | 1/2010 |
| WO | WO-2010/011096 A2 | 1/2010 |
| WO | WO-2010/048308 A2 | 4/2010 |
| WO | WO-2010/078325 A2 | 7/2010 |
| WO | WO-2010/082804 A2 | 7/2010 |
| WO | WO-2010/117760 A2 | 10/2010 |
| WO | WO-2010/129655 A2 | 11/2010 |
| WO | WO-2010/135541 A2 | 11/2010 |
| WO | WO-2011/130229 A1 | 10/2011 |
| WO | WO-2011/134084 A1 | 11/2011 |
| WO | WO-2012/088608 A1 | 7/2012 |
| WO | WO-2012/099851 A2 | 7/2012 |
| WO | WO-2013/058833 A1 | 4/2013 |
| WO | WO-2013/059491 A1 | 4/2013 |
| WO | WO-2013/071262 A1 | 5/2013 |
| WO | WO-2015/112015 A1 | 7/2015 |
| WO | WO-2015/112017 A1 | 7/2015 |
| WO | WO-2016/007873 A1 | 1/2016 |
| WO | WO-2016/090251 A1 | 6/2016 |
| WO | WO-2016/123342 A2 | 8/2016 |
| WO | WO-2017/031114 A1 | 2/2017 |
| WO | WO-2017/058822 A1 | 4/2017 |
| WO | WO-2017/074466 A1 | 5/2017 |
| WO | WO-2017/155569 A1 | 9/2017 |
| WO | WO-2017/171871 A1 | 10/2017 |
| WO | WO-2017/173395 A1 | 10/2017 |
| WO | WO-2017/173413 A1 | 10/2017 |
| WO | WO-2017/214130 A1 | 12/2017 |
| WO | WO-2018/004517 A1 | 1/2018 |
| WO | WO-2018/035420 A1 | 2/2018 |

OTHER PUBLICATIONS

Milián et al., "Alkaline phosphatase and hypophosphatasia," Calcif Tissue Int. 98(4):398-416 (2016).
Kishnani et al., "Biochemical and physical function outcomes in adolescents and adults with hypophosphatasia treated with asfotase alfa for up to 4 years: interim results from a phase II study," Endocrine Society's 98th Annual Meeting and Expo, Apr. 1-4, Boston, MA. Abstract OR26-3 (2016) (2 pages).
International Search Report and Written Opinion for International Patent Application No. PCT/US2017/025590, dated Jun. 29, 2017 (18 pages).
Iqbal et al., "Recurrent Metatarsal Fractures in Postmenopausal Woman With Low Serum Alkaline Phosphatase: A Rare Diagnosis Not to Miss," J Investig Med High Impact Case Rep. 5(3):1-3 (2017).
Ahn et al., "Idiopathic calcium pyrophosphate dihydrate (CPPD) crystal deposition disease in a young male patient: a case report," J Korean Med Sci. 18(6):917-20 (2003).
Cahill et al., "Infantile hypophosphatasia: transplantation therapy trial using bone fragments and cultured osteoblasts,"J. Clin Endocrinol Metab. 92(8): 2923-30 (2007).
Glass et al., "The infant skull: a vault of information," Radiographics. 24(2):507-22 (2004).
Herasse et al., "Molecular study of three cases of odontohypophosphatasia resulting from heterozygosity for mutations in the tissue non-specific alkaline phosphatase gene," J Med Genet. 40(8):605-9 (2003).
Ishida et al., "Tissue-nonspecific alkaline phosphatase with an Asp(289)→Val mutation fails to reach the cell surface and undergoes proteasome-mediated degradation," J Biochem. 134(1):63-70 (2003).
Mornet, "Hypophosphatasia," Orphanet J Rare Dis. 2:(40) (2007) (8 pages).

(56) References Cited

OTHER PUBLICATIONS

Spentchian et al., "Severe hypophosphatasia: characterization of fifteen novel mutations in the ALPL gene," Hum Mutat. 22(1) (2003) (5 pages).

Takinami et al.. "The mutant (F310L and V365I) tissue-nonspecific alkaline phosphatase gene from hypophosphatasia," J Med Dent Sci. 51(1):67-74 (2004).

Sawai et al., "Severe perinatal hypophosphatasia due to homozygous deletion of T at nucleotide 1559 in the tissue nonspecific alkaline phosphatase gene,". Prenat Diagn. 23(9):743-6 (2003).

Wickramasinghe et al., "A case of hypophosphatasia," Ceylon Med J. 48(3):94-5 (2003).

Yamamoto et al., "A successful treatment with pyridoxal phosphate for West syndrome in hypophosphatasia," Pediatr Neurol. 30(3):216-8 (2004).

International Preliminary Report on Patentability for International Patent Application No. PCT/US2016/015366, dated Aug. 10, 2017 (10 pages).

International Search Report and Written Opinion for International Patent Application No. PCT/US2017/047527, dated Nov. 6, 2017 (10 pages).

Milián et al., "Hypophosphatasia—pathophysiology and treatment," available in PMC Sep. 22, 2014, published in final edited form as: Actual Osteol. 8(3):164-182 (2012) (21 pages).

Padidela et al., "P1-118: Management of Tracheobronchomalacia During Asfotase Alfa Treatment in Infants with Perinatal-Onset Hypophosphatasia: A Case Series," European Society for Paediatric Endocrinology (ESPE), Paris, France, Sep. 10-12, 2016 (1 page).

Mornet et al., "Structural evidence for a functional role of human tissue nonspecific alkaline phosphatase in bone mineralization," J Biol Chem. 276(33):31171-8 (2001).

Bhattacharyya et al., "Hypophosphatasia and the risk of atypical femur fractures: a case-control study," BMC Muscoloskelet Disord. 17:332 (2016) (4 pages).

Bishop, "Asfotase alfa for hypophosphatasia," Horizon Scanning Centre. National Institute for Health Research. http://www.hsric.nihr.ac.uk/topics/asfotase-alfa-for-hypophosphatasia/download, retrieved Oct. 20, 2013 (9 pages).

Bishop et al., "Transformative therapy in hypophosphatasia," Arch Dis Child. 101(6):514-5 (2016).

Bishop, "Clinical management of hypophosphatasia," Clin Cases Miner Bone Metab. 12(2):170-3 (2015).

Durussel et al., "Bone mineralization-dependent craniosynostosis and craniofacial shape abnormalities in the mouse model of infantile hypophosphatasia," Dev Dyn. 245(2):175-82 (2016).

Braunstein, "Multiple fractures, pain, and severe disability in a patient with adult-onset hypophosphatasia," Bone Rep. 4:1-4 (2015).

Bloch-Zupan, "Hypophosphatasia: diagnosis and clinical signs—a dental surgeon perspective," Int J Paediatr Dent. 26(6):426-438 (2016).

Kishnani et al., "Monitoring guidance for patients with hypophosphatasia treated with asfotase alfa," Mol Genet Metab. 122(1-2):4-17 (2017).

Güzel et al., "Pyridoxine-responsive seizures in infantile hypophosphatasia and a novel homozygous mutation in ALPL gene," J Clin Res Pediatr Endocrinol. 8(3):360-4 (2016).

Gasque et al., "Improvement of the skeletal and dental hypophosphatasia phenotype in Alpl -/- mice by administration of soluble (non-targeted) chimeric alkaline phosphatase," Available in PMC Mar. 1, 2016, published in final edited form as: Bone. 72:137-147 (2015) (25 pages).

Fodor et al., "Differencial diagnosis of the low alkaline phosphatase activities," Orv Hetil. 158(26): 1003-1007 (2017) (Article in Hungarian) (English Abstract included).

McKiernan et al., "Clinical and radiographic findings in adults with persistent hypophosphatasemia," J Bone Miner Res. 29(7):1651-60 (2014).

Martos-Moreno et al., "Hypophosphatasia: clinical manifestations, diagnostic recommendations and therapeutic options," An Pediatr (Barc). S1695-4033(17)30223-0 (2017) (11 pages) (Article in Spanish) (English Abstract included).

Kulikova et al., "Hypophosphatasia: the clinical description of 3 cases of the disease with the molecular-genetic verification of the diagnosis," Problems of Endocrinology. 61(3):37-42 (2015) (Article in Russian) (English Abstract included).

Orimo, "Pathophysiology of hypophosphatasia and the potential role of asfotase alfa," Ther Clin Risk Manag. 12:777-86 (2016).

Morrow, "Expensive new biologic helps children fight hypophosphatasia," Manag Care. 24(12) (2015) (7 pages).

Mornet et al., "Hypophosphatasia," GeneReviews. https://www.ncbi.nlm.nih.gov/books/NBK1150/, retrieved Dec. 6, 2017, initially published Nov. 20, 2007, last updated Feb. 4, 2016 (25 pages).

Mori et al., "Case series: odontohypophosphatasia or missed diagnosis of childhood/adult-onset hypophosphatasia?—Call for a long-term follow-up of premature loss of primary teeth," Bone Rep. 5:228-232 (2016).

Remde et al., "Successful asfotase alfa treatment in an adult dialysis patient with childhood-onset hypophosphatasia," J Endoc Soc. 1(9):1188-93 (2017).

Panesar, "Hypophosphatasia: a rare disorder," US Pharm. 42(5) (2017) (8 pages).

Padidela et al., "Enzyme-replacement therapy in life-threatening perinatal hypophosphatasia in a premature infant," Endocrine Abstracts. 33:P9 (2013) (1 page).

Sotillo et al., "Signs and symptoms of hypophosphatasia," Dimensions of Dental Hygiene. 15(4):44-47 (2017).

Simm et al., "Successful use of enzyme replacement therapy in infantile hypophosphatasia," J Paediatr Child Health. 53(9):925-926 (2017).

Sheikh et al., "A newborn with no bones: neonatal hypophosphatasia with respiratory distress," J Pediatr. 188:306 (2017).

Saglam et al., "Clinical and genetic findings of Turkish hypophosphatasia cases," J Clin Res Pediatr Endocrinol. 9(3):229-236 (2017).

Whyte et al., "Asfotase alfa treatment improves survival for perinatal and infantile hypophosphatasia," J Clin Endocrinol Metab. 101(1):334-42 (2016) (17 pages).

Wang et al., "Current concepts in odontohypophosphatasia form of hypophosphatasia and report of two cases," BMC Oral Health. 16(1):70 (2016) (8 pages).

Taketani et al., "Ex vivo expanded allogeneic mesenchymal stem cells with bone marrow transplantation improved osteogenesis in infants with severe hypophosphatasia," Cell Transplant. 24(10):1931-43 (2015).

Belachew et al., "Infantile hypophosphatasia secondary to a novel compound heterozygous mutation presenting with pyridoxine-responsive seizures," JIMD Rep. 11:17-24 (2013).

Whyte et al., "Asfotase alfa therapy for children with hypophosphatasia," JCI Insight. 1(9):e85971 (2016) (11 pages).

Whyte, "Hypophosphatasia: enzyme replacement therapy brings new opportunities and new challenges," J Bone Miner Res. 32(4):667-675 (2017).

Alexion Third Quarter 2017 Earnings Call, "http://files.shareholder.com/downloads/ALXN/5636824573x0x961197/3B361D6E-80E2-463E-BOE5-3EAD7FC5B9D0/Alexion_Q3_2017_Earnings_Slides.pdf" (43 pages).

Urlaub et al., "Isolation of Chinese hamster cell mutants deficient in dihydrofolate reductase activity," Proc Natl Acad Sci U S A. 77(7):4216-20 (1980).

Graham et al., "Characteristics of a human cell line transformed by DNA from human adenovirus type 5," J Gen Virol. 36(1):59-74 (1977).

Mather, "Establishment and characterization of two distinct mouse testicular epithelial cell lines," Biol Reprod. 23(1):243-52 (1980).

Le Du et al., "Crystal structure of alkaline phosphatase from human placenta at 1.8 A resolution. Implication for a substrate specificity," J Biol Chem. 276(12):9158-65 (2001) (9 pages).

Stec et al., "A revised mechanism for the alkaline phosphatase reaction involving three metal ions," J Mol Biol. 299(5):1303-11 (2000).

Alexion, "Highlights of Prescribing Information" for Strensiq®, 2018 (8 pages).

European Collection of Authenticated Cell Cultures (ECACC) Accession No. 85110503. Retrieved May 2, 2018 (3 pages).

(56) References Cited

OTHER PUBLICATIONS

UniProtKB Accession No. P05186. Retrieved May 2, 2018 (19 pages).
UniProtKB Accession No. P01857. Retrieved May 2, 2018 (13 pages).
Belkhouribchia et al., "Case Report: Osteomalacia with low alkaline phosphatase: a not so rare condition with important consequences," BMJ Case Rep. doi: 10.1136/bcr-2015-212827 (2016) (4 pages).
Berkseth et al., "Clinical spectrum of hypophosphatasia diagnosed in adults," Bone. 54(1):21-7 (2013).
Bianchi, "Hypophosphatasia: an overview of the disease and its treatment," Osteoporos Int. 26(12):2743-57; DOI 10.1007/s00198-015-3272-1 (2015) (15 pages).
Bobryshev et al., "Role of bone-type tissue-nonspecific alkaline phosphatase and PHOSPO1 in vascular calcification," Curr Pharm Des. 20(37):5821-8 (2014).
Bowden et al., "Asfotase alfa treatment for 1 year in a 16 year-old male with severe childhood hypophosphatasia," Osteoporos Int. 29(2):511-5; DOI: 10.1007/s00198-017-4267-x (2018) (5 pages).
Briot et al., "Adult hypophosphatasia," Curr Opin Rheumatol. 28(4):448-51 (2016).
Buchet et al., "Multisystemic functions of alkaline phosphatases," Methods Mol Biol. 1053:27-51 (2013).
Deeb et al., "Could alerting physicians for low alkaline phosphatase levels be helpful in early diagnosis of hypophosphatasia?," J Clin Res Pediatr Endocrinol. 10(1):19-24 (2018).
Hofmann et al., "Recombinant enzyme replacement therapy in hypophosphatasia," Subcell Biochem. 76:323-41 (2015).
Hofmann et al., "Asfotase alfa: enzyme replacement for the treatment of bone disease in hypophosphatasia," Drugs Today (Barc). 52(5):271-85 (2016).
Kitaoka et al., "Safety and efficacy of treatment with asfotase alfa in patients with hypophosphatasia: results from a Japanese clinical trial," Clin Endocrinol (Oxf). 87(1):10-19 (epub pp. 1-10) (2017).
Linglart et al., "Hypophosphatasia," Curr Osteoporos Rep. 14(3):95-105; DOI 10.1007/s11914-016-0309-0 (2016) (11 pages).
Mornet, "Hypophosphatasia," Metabolism. 82:142-155; DOI: 10.1016/j.metabol.2017.08.013 (2018) (30 pages).
Mornet, "Molecular genetics of hypophosphatasia and phenotype-genotype correlations," Subcell Biochem. 76:25-43 (2015).
Okazaki et al., "Lethal hypophosphatasia successfully treated with enzyme replacement from day 1 after birth," Eur J Pediatr. 175(3):433-7; DOI 10.1007/s00431-015-2641-2 (2016) (5 pages).
Park et al., "First Korean case of infantile hypophosphatasia with novel mutation in ALPL and literature review," Ann Clin Lab Sci. 46(3):302-7 (2016).
Phillips et al., "Physical therapy management of infants and children with hypophosphatasia," Mol Genet Metab. 119(1-2):14-9 (2016).
Rockman-Greenberg, "Hypophosphatasia," Pediatr Endocrinol Rev. 10 Suppl 2:380-8 (2013) (Abstract only).
Rodriguez et al., "Respiratory mechanics in an infant with perinatal lethal hypophosphatasia treated with human recombinant enzyme replacement therapy," Pediatr Pulmonol. 47(9):917-22 (2012).
Saraff et al., "A diagnostic algorithm for children with low alkaline phosphatase activities: lessons learned from laboratory screening for hypophosphatasia," J Pediatr. 172:181-6 (2016) (7 pages).
Sather, "008-case study: 3 year old female with hypophosphatasia, treated with asfotase alfa replacement," Journal of Pediatric Nursing. 34:104 (2017).
Schmidt et al., "Hypophosphatasia: What is currently available for treatment?" Internist (Berl). 57(12):1145-1154 (2016) (Article in German) (English abstract).
Schmidt et al., "Clinical radiographic and biochemical characteristics of adult hypophosphatasia," Osteoporos Int. 28(9):2653-2662 (2017).
Scott, "Asfotase alfa in perinatal/infantile-onset and juvenile-onset hypophosphatasia: a guide to its use in the USA," BioDrugs. 30(1):41-8 (2016).
Scott, "Asfotase alfa: a review in paediatric-onset hypophosphatasia," Drugs. 76(2):255-62 (2016).
Shapiro et al., "Hypophosphatasia in adults: clinical assessment and treatment considerations," J Bone Miner Res. 32(10):1977-1980 (2017).
Siller et al., "Alkaline phosphatase: discovery and naming of our favorite enzyme," J Bone Miner Res. 33(2):362-4 (2018).
Takahashi et al., "Parental serum alkaline phosphatase activity as an auxiliary tool for prenatal diagnosis of hypophosphatasia," Prenat Diagn. 37(5):491-6 (2017).
Tenorio et al., "Molecular and clinical analysis of ALPL in a cohort of patients with suspicion of hypophosphatasia," Am J Med Genet A. 173(3):601-10 (2017).
Tsiantouli et al., "Hypophosphatasia," Rev Med Suisse. 13(559):855-8 (2017) (Article in French).
Weber et al., "Burden of disease in adult patients with hypophosphatasia: Results from two patient-reported surveys," Metabolism. 65(10):1522-30 (2016).
Whyte, "Hypophosphatasia—aetiology, nosology, pathogenesis, diagnosis and treatment," Nat Rev Endocrinol. 12(4):233-46 (2016).
Whyte, "Hypophosphatasia: an overview for 2017," Bone. 102:15-25 (2017).
Whyte et al., "Hypophosphatasia: natural history study of 101 affected children investigated at one research center," Bone. 93:125-138 (2016).
Whyte et al., "Hypophosphatasia: validation and expansion of the clinical nosology for children from 25 years experience with 173 pediatric patients," Bone. 75:229-39 (2015).
International Search Report and Written Opinion for International Patent Application No. PCT/US2016/054013, dated Dec. 13, 2016 (19 pages).
Seefried et al., "Pharmacodynamic results from a phase 2a, randomized, multicenter, open-label, dose-ranging study of asfotase alfa in adults with pediatric hypophosphatasia," 100th Annual Meeting and Expo of the Endocrine Society, Mar. 17-20, 2018, Chicago, IL. (1 page).
International Search Report and Written Opinion for International Patent Application No. PCT/US2018/020859, dated Jun. 19, 2018 (14 pages).
López-Delgado et al., "Abnormal bone turnover in individuals with low serum alkaline phosphatase," Osteoporosis Int. 29(9):2147-2150; doi: 10.1007/s00198-018-4571-0 (Supplementary information included) (2018) (6 pages).
Matsumoto et al., "Rescue of severe infantile hypophosphatasia mice by AAV-mediated sustained expression of soluble alkaline phosphatase," Hum Gene Ther. 22(11):1355-64 (2011).
Hofmann et al., "Clinical aspects of hypophosphatasia: an update," Clinic Rev Bone Miner Metab. 11(2):60-70 (2013).
Taketani et al., "Clinical and genetic aspects of hypophosphatasia in Japanese patients," Arch Dis Child. 99(3):211-5 (2014) (6 pages).
Whyte, "Physiological role of alkaline phosphatase explored in hypophosphatasia," Ann N Y Acad Sci. 1192:190-200 (2010).
Hofmann et al., "Compound heterozygosity of two functional null mutations in the ALPL gene associated with deleterious neurological outcome in an infant with hypophosphatasia," Bone. 55:150-7 (2013).
De Roo et al., "Infantile hypophosphatasia without bone deformities presenting with severe pyridoxine-resistant seizures," Molecular Genetics and Metabolism 111(3):404-7 (2014).
International Search Report and Written Opinion for International Patent Application No. PCT/US2015/064003, dated Mar. 31, 2016 (13 pages).
Lazdunski et al., "Structure-function relationships for some metalloalkaline phosphatases of *E. coli*," Eur J Biochem. 8(4):510-7 (1969).
Bobyr et al., "High-resolution analysis of Zn(2+) coordination in the alkaline phosphatase superfamily by EXAFS and x-ray crystallography," J Mol Biol. 415(1):102-17 (2012).
International Search Report and Written Opinion for International Patent Application No. PCT/US2017/036133, dated Aug. 24, 2017 (10 pages).

(56) References Cited

OTHER PUBLICATIONS

International Search Report and Written Opinion for International Patent Application No. PCT/US2018/025206, dated Jul. 3, 2018 (25 pages).
Kishnani et al., "OR26-3 Biochemical and Physical Function Outcomes in Adolescents and Adults with Hypophosphatasia Treated with Asfotase Alfa for up to 4 Years: Interim Results from a Phase II Study," ENDO 2016, Boston, MA, Apr. 3, 2016 (22 pages).
International Search Report and Written Opinion for International Patent Application No. PCT/US2017/025618, dated Jul. 11, 2017 (22 pages).
Li et al., "Standard reference for the six-minute-walk test in healthy children aged 7 to 16 years," Am J Respir Crit Care Med. 176(2):174-80 (2007).
Park et al., "Ex vivo assessment of contractility, fatigability and alternans in isolated skeletal muscles," J Vis Exp. 69:e4198 (2012) (8 pages).
Phillips et al., "FRI-224: Improved activities of daily living and physical function, with decreased pain, in children with hypophosphatasia treated for three years with asfotase alfa: results from the childhood health assessment questionnaire and the pediatric outcomes data collection instrument," The Endocrine Society's 97th Annual Meeting & Expo, San Diego, California, Mar. 5-8, 2015 (1 page).
Whyte et al., "Hypophosphatasia: Enzyme replacement therapy (asfotase alfa) decreases TNSALP substrate accumulation and improves functional outcomes in affected adolescents and adults," Bull Group Int Rech Sci Stomatol Odontol. 51(1):35 (2012).
Sugano et al., "Successful gene therapy in utero for lethal murine hypophosphatasia," Hum Gene Ther. 23(4):399-406 (2012).
International Search Report and Written Opinion for International Patent Application No. PCT/US2015/039973, dated Oct. 5, 2015 (12 pages).
Johnson et al., "Motor proficiency in children with neurofibromatosis type 1," Pediatr Phys Ther. 22(4):344-8 (2010).
Gates et al., "Effects of age, sex, and comorbidities on the pediatric outcomes data collection instrument (PODCI) in the general population," J Pediatr Orthop. 35(2):203-9 (2015).
International Search Report and Written Opinion for International Patent Application No. PCT/US2016/049983, dated Nov. 29, 2016 (12 pages).
International Search Report and Written Opinion for International Patent Application No. PCT/US2016/015366, dated Aug. 9, 2016 (14 pages).
Extended European Search Report for European Application No. 18173111.8, dated Aug. 21, 2018 (9 pages).
Achord et al., "Human beta-glucuronidase: in vivo clearance and in vitro uptake by a glycoprotein recognition system on reticuloendothelial cells," Cell 15(1):269-278 (1978).
Addison et al., "Pyrophosphate inhibits mineralization of osteoblast cultures by binding to mineral, up-regulating osteopontin, and inhibiting alkaline phosphate activity," J Biol Chem. 282(21):15872-15883 (2007).
Advisory Action for U.S. Appl. No. 11/484,870, dated Dec. 20, 2007 (4 pages).
Ali et al., "Isolation and characterization of calcifying matrix vesicles from epiphyseal cartilage," Proc Natl Acad Sci USA. 67(3):1513-1520 (1970).
Altarescu et al., "The efficacy of enzyme replacement therapy in patients with chronic neuronopathic Gaucher's disease," J Pediatr. 138(4):539-547 (2001).
Anderson et al., "Impaired calcification around matrix vesicles of growth plate and bone in alkaline phosphatase-deficient mice," *Am J Pathol.* 164:841-847 (2004).
Anderson et al., "Matrix vesicles in osteomalacic hypophosphatasia bone contain apatite-like mineral crystals," Am J Pathol. 151(6):1555-61 (1997).
Anderson et al., "Pyrophosphate stimulation of calcium uptake into cultured embryonic bones. Fine structure of matrix vesicles and their role in calcification," Dev Biol. 34:211-227 (1973).

Anderson et al., "Sustained osteomalacia of long bones despite major improvement in other hypophosphatasia-related mineral deficits in tissue nonspecific alkaline phosphatase/nucleotide pyrophosphatase phosphodiesterase 1 double-deficient mice," Am J Pathol. 166(6):1711-1720 (2005).
Anderson et al., "The role of matrix vesicles in growth plate development and biomineralization," Front Biosci. 10:822-837 (2005).
Attwood, "The Babel of Bioinformatics," Genomics. 290(5491):471-3 (2000).
Barranger et al., "Lessons learned from the development of enzyme therapy for Gaucher disease," J Inherit Metab Dis. 24(Supp 2):89-96 (2001).
Barton et al., "Replacement therapy for inherited enzyme deficiency—macrophage-targeted glucocerebrosidase for Gaucher's disease," N Engl J Med. 324(21):1464-70 (1991) (abstract only).
Beertsen et al., "Root development in mice lacking functional tissue non-specific alkaline phosphatase gene: Inhibition of acellular cementum formation," J Dent Res. 78(6):1221-1229 (1999).
Bernardi, "Chromatography of proteins on hydroxyapatite," Methods Enzymol. 27:471-9 (1973).
Bennett et al., "Extracellular domain-IgG fusion proteins for three human natriuretic peptide receptors," J Biol Chem. 266(34):23060-23067 (1991).
Bernard, "Ultrastructural localization of alkaline phosphatase in initial intramembranous osteogenesis," Clin Orthop Relat Res. 135:218-225 (1978).
Bobé et al., "Fas-mediated liver damage in MRL hemopoietic chimeras undergoing lpr-mediated graft-versus-host disease," J Immunol. 159:4197-4204 (1997).
Bocciardi et al., "Overexpression of the C-type natriuretic peptide (CNP) is associated with overgrowth and bone anomalies in an individual with balanced t(2;7) translocation," Hum Mutat. 28(7):724-731 (2007).
Bonilla, "Pharmacokinetics of immunoglobulin administered via intravenous or subcutaneous routes," Immunol Allergy Clin N Am. 28:803-819 (2008).
Boskey, "Amorphous calcium phosphate: The contention of bone," J Dent Res. 76:1433-1436 (1997).
Boskey et al., "Matrix vesicles promote mineralization in a gelatin gel," Calcif Tissue Int 60(3):309-15 (1997).
Brenner et al., "Diverse biological actions of atrial natriuretic peptide," Physiol Rev. 70(3):665-699 (1990).
Byers et al., "Effect of enzyme replacement therapy on bone formation in a feline model of mucopolysaccharidosis type VI," Bone. 21(5):425-431 (1997).
Cameron et al., "Minireview: Natriuretic peptides during development of the fetal heart and circulation," Endocrinology. 144(6):2191-2194 (2003).
Campbell et al., "Insulin-like growth factor (IGF)-binding protein-5-(201-218) region regulates hydroxyapatite and IGF-I binding," Am J Physiol. 273:E1005-1013 (1997).
Chen et al., "Gly369Cys mutation in mouse FGFR3 causes achondroplasia by affecting both chondrogenesis and osteogenesis," J Clin Invest. 104(11):1517-1525 (1999).
Choe et al., "Substrate profiling of cysteine proteases using a combinatorial peptide library identifies functionally unique specificities," J Biol Chem. 281(18):12824-12832 (2006).
Chusho et al., "Dwarfism and early death in mice lacking C-type natriuretic peptide," Proc Natl Acad Sci USA. 98(7):4016-4021 (2001).
Ciancaglini et al., "Contribution of matrix vesicles and alkaline phosphatase to ectopic bone formation," Braz. J Med Biol Res. 39(5):603-10 (2006).
Cleland et al., "Emerging protein delivery methods," Curr Opin Biotechnol. 12:212-219 (2001).
Clemens et al., "Pharmacokinetics and biological actions of subcutaneously administered human brain natriuretic peptide," J Pharmacol Exp Ther. 287(1):67-71 (1998).
Communication from Examining Division for European Application No. EP 05 739 065.0, dated Jun. 18, 2009 (11 pages).
Communication from Examining Division for European Application No. EP 05 739 065.0, dated Jun. 11, 2010 (5 pages).

(56) References Cited

OTHER PUBLICATIONS

Communication from Examining Division for European Application No. EP 08 757 088, dated Apr. 20, 2011 (4 pages).
Crawley et al., "Enzyme replacement therapy in a feline model of Maroteaux-Lamy Syndrome," J Clin Invest. 97(8):1864-73 (1996).
Daggubati et al., "Adrenomedullin, endothelin, neuropeptide Y, atrial, brain, and C-natriuretic prohormone peptides compared as early heart failure indicators," Cardiovasc Res. 36:246-255 (1997).
Data Sheet for pFUSE-SEAP-hFC "Plasmid designed for the expression of a SEAP-Fc Fusion protein," Invivogen, San Diego, CA (4 pages) (1989).
De la Croix Ndong et al., "Asfotase-alpha improves bone growth, mineralization and strength in mouse models of neurofibromatosis type-1," Nat Med. 20(8):904-10 (2014) (10 pages).
De Plater et al., "The natriuretic peptide (OVCNP-39) from platypus (*Ornithorhynchus anatinus*) venom relaxes the isolated rat uterus and promotes oedema and mast cell histamine release," Toxicon. 36(3):847-857 (1998).
Declaration of Dr. Philippe Crine for EP 08757088.3, executed Jan. 14, 2011 (6 pages).
Di Mauro et al., "Kinetic characterization of hypophosphatasia mutations with physiological substrates," J Bone Miner Res. 17(8):1383-91 (2002).
Dumont et al., "Monomeric Fc fusions: impact on pharmacokinetic and biological activity of protein therapeutics," BioDrugs. 20(3):151-60 (2006).
EBI Blast for Accession No. ATD17216. Entered Oct. 16, 2008 (1 page).
Eng et al., "Safety and efficacy of recombinant human alpha-galactosidase A—replacement therapy in Fabry's disease," N Engl J Med. 345(1):9-16 (2001).
Engel et al., "Characterization of the hormone binding site of natriuretic peptide receptor-C," FEBS Lett. 360:169-172 (1995).
Epps et al., "Application No. 125513Orig1s000 Medical Review(s)," Center for Drug Evaluation and Research, <http://www.accessdata.fda.gov/drugsatfda_docs/nda/2015/125513Orig1s000MedR.pdf>, Oct. 20, 2015 (254 pages).
European Search Report for European Application No. EP08757088, dated Jun. 21, 2010 (6 pages).
European Search Report for European Patent Application No. 12842640.0, dated Mar. 13, 2015 (7 pages).
Extended European Search Report for European Application No. EP 11 00 0196.3, dated Jun. 22, 2011 (6 pages).
Extended European Search Report for European Application No. EP 11 00 4496.3, dated Aug. 26, 2011 (7 pages).
Extended European Search Report for European Application No. 11774253.6, dated Oct. 14, 2013 (8 pages).
Farley et al., "Effects of tunicamycin, mannosamine, and other inhibitors of glycoprotein processing on skeletal alkaline phosphatase in human osteoblast-like cells," Calcif Tissue Int. 76:63-74 (2005).
Farnum et al., "In vivo delivery of fluoresceinated dextrans to the murine growth plate: imaging of three vascular routes by multiphoton microscopy," available in PMC Oct. 28, 2008, publiched in final edited form as: Anat Rec A Discov Mol Cell Evol Biol. 288(1):91-103 (2006) (22 pages).
Fedde et al., "Alkaline phosphatase knock-out mice recapitulate the metabolic and skeletal defects of infantile hypophosphatasia," available in PMC Mar. 7, 2011, published in final edited form as: J Bone Miner Res. 14(12):2015-2026 (1999) (19 pages).
Fujisaki et al., "Osteotropic Drug Delivery System (ODDS) based on bisphosphonic prodrug. IV effects of osteotropic estradiol on bone mineral density and uterine weight in ovariectomized rats," J Drug Target. 5(2):129-138 (1997).
Fujisawa et al., "Acidic amino acid-rich sequences as binding sites of osteonectin to hydroxyapatite crystals," Biochim Biophys Acta. 1292:53-60 (1996).
Furbish et al., "Uptake and distribution of placental glucocerebrosidase in rat hepatic cells and effects of sequential deglycosylation," Biochim Biophys Acta. 673:425-434 (1981).

Furuya et al., "Structural requirements of C-type natriuretic peptide for elevation of cyclic GMP in cultured vascular smooth muscle cells," Biochem Biophys Res Commun. 183(3):964-969 (1992).
Garg, Investigation of the role of FcRn in the absorption, distribution, and elimination of monoclonal antibodies. Dissertation: State University of New York at Buffalo, 2007 (Abstract only) (2 pages).
Gilbert et al., "Chimeric peptides of statherin and osteopontin that bind hydroxyapatite and mediate cell adhesion," J Biol Chem. 275(21):16213-8 (2000).
Greenberg et al., "A homoallelic Gly$^{317}$→ Asp mutation in ALPL causes the perinatal (lethal) form of hypophosphatasia in Canadian mennonites," Genomics. 17:215-217 (1993).
Guo et al., "Protein tolerance to random amino acid change," Proc Natl Acad Sci USA. 101(25):9205-9210 (2004).
Hagiwara et al., "Autocrine regulation of rat chondrocyte proliferation by natriuretic peptide C and its receptor, natriuretic peptide receptor-B," J Biol Chem. 269(14):10729-10733 (1994).
Hagiwara et al., "cGMP produced in response to ANP and CNP regulates proliferation and differentiation of osteoblastic cells," Am J Physiol. 270:C1311-C1318 (1996).
Hailing Linder et al., "Glycosylation differences contribute to distinct catalytic properties among bone alkaline phosphotase isoforms," available in PMC Nov. 1, 2010, published in final edited form as: Bone. 45(5):987-993 (2009) (17 pages).
Hardy et al., "Dissection of a carboxy-terminal region of the yeast regulatory protein RAP1 with effects on both transcriptional activation and silencing," Mol Cell Biol. 12(3):1209-1217 (1992).
Harmey et al., "Concerted regulation of inorganic pyrophosphate and osteopontin by Akp2, Enpp1, and Ank," Am J Pathol. 164(4):1199-1209 (2004).
Harmey et al., "Elevated skeletal osteopontin levels contribute to the hypophosphatasia phenotype in Akp2$^{-/-}$ mice," J Bone Miner Res. 21(9):1377-1386 (2006).
Harris, "The human alkaline phosphatases: what we know and what we don't know," Clin Chim Acta. 186:133-50 (1989).
Hawrylak et al., "The solubilization of tetrameric alkaline phosphatase from human liver and its conversion into various forms by phosphatidylinositol phospholipase C or proteolysis," J Biol Chem. 263(28):14368-14373 (1988).
Henthorn et al., "Different missense mutations at the tissue-nonspecific alkaline phosphatase gene locus in autosomal recessively inherited forms of mild and severe hypophosphatasia," Proc Natl Acad Sci USA. 89:9924-9928 (1992).
Henthorn et al., "Missense mutations of the tissue-nonspecific alkaline phosphatase gene in hypophosphatasia," Clin Chem. 38(12):2501-5 (1992).
Hessle et al., "Tissue-nonspecific alkaline phosphatase and plasma cell membrane glucoprotein-1 are central antagonistic regulators of bone mineralization," Proc Natl Acad Sci USA. 99(14): 9445-9449 (2002).
Highlights of Prescribing Information for Strensiq™, Alexion Pharmaceuticals, Inc., available <http://www.alexion.com/Documents/strensiq_pi-10-2015.aspx>, 2015 (19 pages).
Hofmann et al., "Clinical aspects of hypophosphatasia: an update," Clinic Rev Bone Miner Metab. 11:60-70 (2013).
Hofmann et al., "Improvement in bone manifestations and respiratory status in infants and young children with HPP treated with asfotase alfa: an update on the ENB-010-10 trial," Bone Abstracts (2015) (3 pages).
Horton et al., "Achondroplasia," Lancet. 370:162-172, 2007.
Hosain et al., "Targeted delivery of antineoplastic agent to bone: biodistribution studies of technetium-99m-labeled gem-bisphosphonate conjugate of methotrexate," J Nucl Med. 37(1):105-7 (1996).
Hult et al., "Engineered enzymes for improved organic synthesis," Curr Opin Biotechnol. 14:395-400 (2003).
Hunter et al., "Modulation of crystal formation by bone phosphoproteins: structural specificity of the osteopontin-mediated inhibition of hydroxyapatite formation," Biochem J. 300:723-728 (1994).
Husain et al., "Fc site-specific labeling of immunoglobulins with calf intestinal alkaline phosphatase," Bioconjug Chem. 5(5):482-90 (1994).

(56) References Cited

OTHER PUBLICATIONS

Ikezawa, "Glycosylphosphatidylinositol (GPI)-anchored proteins," *Biol Pharm Bull.* 25(4):409-417 (2002).
Inoue et al., "Four functionally distinct C-type natriuretic peptides found in fish reveal evolutionary history of the natriuretic peptide system," Proc Natl Acad Sci USA. 100(17):10079-10084 (2003).
International Preliminary Report on Patentability and Written Opinion for International Application No. PCT/CA2011/050258, dated Nov. 15, 2012 (9 pages).
International Search Report and Written Opinion for International Application No. PCT/CA2011/050258, dated Jul. 29, 2011 (14 pages).
International Search Report and Written Opinion for International Application No. PCT/US12/39004, dated Nov. 2, 2012 (22 pages).
International Search Report and Written Opinion for International Application No. PCT/CA2005/000615, dated Aug. 18, 2005 (14 pages).
International Search Report and Written Opinion for International Application No. PCT/CA2008/000923, dated Sep. 12, 2008 (11 pages).
International Search Report and Written Opinion for International Application No. PCT/US2015/058498, dated Jan. 22, 2016 (12 pages).
International Search Report and Written Opinion for International Application No. PCT/US16/25721, dated Aug. 17, 2016 (18 pages).
International Search Report and Written Opinion for International Application No. PCT/US2016/039595, dated Feb. 21, 2017 (16 pages).
International Search Report and Written Opinion for International Application No. PCT/US2016/047166, dated Nov. 7, 2016 (15 pages).
International Search Report for International Application No. PCT/CA2011/050807, dated Apr. 13, 2012 (8 pages).
International Search Report for International Patent Application No. PCT/US2012/060869, dated Mar. 25, 2013 (5 pages).
Invitation to Pay Additional Fees for International Application No. PCT/US12/39004, dated Aug. 29, 2012 (2 pages).
Invitation to Pay Additional Fees for International Application No. PCT/US2016/015366, dated Jun. 1, 2016 (7 pages).
Invitation to Pay Additional Fees for International Application No. PCT/CA2011/050807, dated Feb. 13, 2012 (2 pages).
Jansonius, "Structure, evolution and action of vitamin $B_6$-dependent enzymes," Curr Opin Struct Biol. 8:759-769 (1998).
Jin et al., "Novel analog of atrial natriuretic peptide selective for receptor-A produces increased diuresis and natriuresis in rats," J Clin Invest. 98(4):969-976 (1996).
Johnson et al., "Matrix vesicle plasma cell membrane glycoprotein-1 regulates mineralization by murine osteoblastic MC3T3 cells," J Bone Miner Res. 14(6):883-892 (1999).
Kakkis et al., "Enzyme-replacement therapy in mucopolysaccharidosis I," N Engl J Med. 344(3):182-8 (2001).
Kalra et al., "The role of C-type natriuretic peptide in cardiovascular medicine," Eur Heart J. 22:997-1007 (2001).
Kasugai et al., "Selective drug delivery system to bone: small peptide $(Asp)_6$ conjugation," J Bone Miner Res. 15(5):936-943 (2000).
Kaufmann et al., "Influence of low temperature on productivity, proteome and protein phosphorylation of CHO cells," Biotechnol Bioeng. 63(5):573-82 (1999).
Kochendoerfer, "Protein & peptide drug delivery—third international conference: Minimally invasive delivery methods," IDrugs. 6(11):1043-1045 (2003).
Kosnik-Infinger et al., "Enzyme replacement therapy for congenital hypophosphatasia allows for surgical treatment of related complex craniosynostosis: a case series," Neurosurg Focus. 38(5):E10 (2015) (8 pages).
Kostenuik et al., "Infrequent delivery of a long-acting PTH-Fc fusion protein has potent anabolic effects on cortical and cancellous bone," J Bone Miner Res. 22(10):1534-1547 (2007).

Lee et al., "Disturbed osteoblastic differentiation of fibrous hamartoma cell from congenital pseudarthrosis of the tibia associated with neurofibromatosis type I," Clin Orthop Surg. 3(3):230-7 (2011).
Leone et al., "Allosteric modulation of pyrophosphatase activity of rat osseous plate alkaline phosphatase by magnesium ions," Int J Biochem Cell Biol. 30:89-97 (1998).
Liu et al.,"Tissue-nonspecific alkaline phosphatase deficiency causes abnormal craniofacial bone development in the Alpl(-/-) mouse model of infantile hypophosphatasia," available in PMC Oct. 1, 2015, published in final edited form as: Bone. 67:81-94 (2014) (30 pages).
Lo et al., "High level expression and secretion of Fc-X fusion proteins in mammalian cells," Protein Eng. 11(6):495-500, 1998.
Madson et al., "Asfotase alfa: sustained efficacy and tolerability in children with hypophosphatasia treated for 5 years," ESPE Abstracts. 84:FC2.4 (2015) (2 pages).
Mahmood et al., "Selection of the first-time dose in humans: comparison of different approaches based on interspecies scaling of clearance," J Clin Pharmacol. 43:692-697 (2003).
Mayer, "Microbiology and immunology on-line: Immunoglobulins: structure and function" <http://pathmicro.med.sc.edu/mayer/IgStruct2000.htm>, University of South Carolina School of Medicine, 12 pages (2009).
Mericq et al., "Regulation of fetal rat bone growth by C-type natriuretic peptide and cGMP," Pediatr Res. 47:189-193 (2000) (9 pages).
Meyer, "Can biological calcification occur in the presence of pyrophosphate?" Arch Biochem Biophys. 231:1-8 (1984).
Michigami et al., "Common mutations F310L and T1559del in the tissue-nonspecific alkaline phosphatase gene are related to distinct phenotypes in Japanese patients with hypophosphatasia," Eur J Pediatr. 164:277-282 (2005).
Milián et al., "Enzyme replacement therapy for murine hypophosphatasia," J Bone Miner Res. 23(6): 777-87 (2008).
Milián, "Mammalian Alkaline Phosphatases," in Biology to Applications in Medicine and Biotechnology, pp. 107-185, 2006 (Wiley-VCH Verlag).
Millan, "Mammalian Alkaline Phosphatases," Wiley-WCH Verlag GmbH & Co., Weinheim, Germany, 1-322 (2006).
Miyazawa et al., "Cyclic GMP-dependent protein kinase II plays a critical role in C-type natriuretic peptide-mediated endochondral ossification," Endocrinology. 143(9):3604-3610 (2002).
Mornet et al., "Identification of fifteen novel mutations in the tissue-nonspecific alkaline phosphatase (TNSALP) gene in European patients with severe hypophosphatasia," Eur J Hum Genet. 6(4):308-14 (1998).
Morris et al., "Immunolocalization of alkaline phosphatase in osteoblasts and matrix vesicles of human fetal bone," Bone Miner. 19:287-298 (1992).
Moss et al., "Association of inorganic-pyrophosphatase activity with human alkaline-phosphatase preparations," Biochem J. 102:53-57 (1967).
Murray, "Lectin-specific targeting of lysosomal enzymes to reticuloendothelial cells," Methods Enzymol. 149:25-42 (1987).
Murshed et al., "Unique coexpression in osteoblasts of broadly expressed genes accounts for the spatial restriction of ECM mineralization to bone," Genes Dev. 19:1093-1104 (2005).
Nahabet et al., "Postnatal Pancraniosynostosis in a Patient With Infantile Hypophosphatasia," Cleft Palate Craniofac J. 53(6):741-4 (2016).
Nakao et al., "The pharmacokinetics of alpha-human atrial natriuretic polypeptide in healthy subjects," Eur J Clin Pharmacol. 31:101-103 (1986).
Narisawa et al., "Abnormal vitamin B6 metabolism in alkaline phosphatase knock-out mice causes multiple abnormalities, but not the impaired bone mineralization,"J Pathol. 193:125-133 (2001).
Narisawa et al., "Inactivation of two mouse alkaline phosphatase genes and establishment of a model of infantile hypophosphatasia," Dev Dyn. 208:432-446 (1997).
Nasu et al., "Aberrant interchain disulfide bridge of tissue-nonspecific alkaline phosphatase with an Arg433 → Cys substitution associated with severe hypophosphatasia," FEBS Journal. 273:5612-5624 (2006).

(56) References Cited

OTHER PUBLICATIONS

NCBI Protein Database Accession No. AAC33858. Retrieved on Apr. 16, 2013 (1 page).
NCBI Protein Database Accession No. AAF64516. Retrieved on Apr. 16, 2013 (2 pages).
NCBI Protein Database Accession No. AAH21289. Retrieved on Apr. 16, 2013 (2 pages).
NCBI Protein Database Accession No. AAH66116. Retrieved on Apr. 16, 2013 (2 pages).
NCBI Protein Database Accession No. AAH90861. Retrieved on Apr. 16, 2013 (2 pages).
NCBI Protein Database Accession No. AAI10910. Retrieved on Apr. 16, 2013 (2 pages).
NCBI Protein Database Accession No. AAI18209. Retrieved on Apr. 17, 2013 (2 pages).
NCBI Protein Database Accession No. AAI26166. Retrieved on Apr. 16, 2013 (2 pages).
NCBI Protein Database Accession No. AAN64273. Retrieved on Apr. 16, 2013 (1 page).
NCBI Protein Database Accession No. NP_000469. Retrieved on Apr. 16, 2013 (2 pages).
NCBI Protein Database Accession No. NP_001623. Retrieved on Apr. 16, 2013 (3 pages).
NCBI Protein Database Accession No. NP_001036028. Retrieved on Apr. 16, 2013 (2 pages).
NCBI Protein Database Accession No. NP_001253798.1, downloaded on Apr. 17, 2013. (2 pages).
NCBI Protein Database Accession No. NP_001622. Retrieved on Apr. 16, 2013 (3 pages).
NCBI Protein Database Accession No. NP_031457. Retrieved on Apr. 16, 2013 (3 pages).
NCBI Protein Database Accession No. NP_037191. Retrieved on Apr. 16, 2013 (3 pages).
NCBI Protein Database Accession No. NP_112603. Retrieved on Apr. 16, 2013 (3 pages).
NCBI Protein Database Accession No. NP_776412. Retrieved on Apr. 17, 2013 (2 pages).
NCBI Protein Database Accession No. NP_789828. Retrieved on Apr. 16, 2013 (3 pages).
NCBI Protein Database Accession No. P01857. Retrieved on Apr. 18, 2013 (7 pages).
NCBI Protein Database Accession No. P05186. Retrieved on Apr. 16, 2013 (19 pages).
NCBI Protein Database Accession No. P05187. Retrieved on Apr. 16, 2013 (10 pages).
NCBI Protein Database Accession No. P08289. Retrieved on Apr. 16, 2013 (5 pages).
NCBI Protein Database Accession No. P09487. Retrieved on Apr. 16, 2013 (4 pages).
NCBI Protein Database Accession No. P09242. Retrieved on Apr. 16, 2013 (6 pages).
NCBI Protein Database Accession No. P09923. Retrieved on Apr. 16, 2013 (6 pages).
NCBI Protein Database Accession No. P10696. Retrieved on Apr. 16, 2013 (7 pages).
NCBI Protein Database Accession No. Q29486. Retrieved on Apr. 16, 2013 (3 pages).
NCBI Protein Database Accession No. Q6PYX1. Retrieved on Oct. 15, 2013 (2 pages).
NCBI Protein Database Accession No. Q9N0V0. Retrieved on Apr. 16, 2013 (1 page).
NCBI Protein Database Accession No. XP_001109717. Retrieved on Apr. 17 2013 (1 page).
Ngo et al., Computational complexity, protein structure prediction, and the levinthal paradox. *The Protein Folding Problem and Tertiary Structure Prediction.* Merz et al. (ed.), 433, 492-495 (1994).
Nishioka et al., "Enhancement of drug delivery to bone: characterization of human tissue-nonspecific alkaline phosphatase tagged with an acidic oligopeptide," Mol Genet Metab. 88:244-255 (2006).

Nosjean et al., "Human tissue non-specific alkaline phosphatases: sugar-moiety-induced enzymic and antigenic modulations and genetic aspects," Biochem J. 321:297-303 (1997).
Oda et al., "A general method for rapid purification of soluble versions of glycosylphosphatidylinositol-anchored proteins expressed in insect cells: an application for human tissue-nonspecific alkaline phosphatase," J Biochem. 126(4):694-9 (1999).
Oikawa et al., "Enzyme replacement therapy on hypophosphatasia mouse model," J Inherit Metab Dis. 9 pages (2013).
Orimo, "The mechanism of mineralization and the role of alkaline phosphatase in health and disease," J Nippon Med Sch. 77(1):4-12 (2010).
Patti et al., "Critical residues in the ligand-binding site of the *Staphylococcus aureus* collagen-binding adhesin (MSCRAMM)," J Biol Chem. 270(20):12005-12011 (1995).
Pedersen et al., "Removal of N-terminal polyhistidine tags from recombinant proteins using engineered aminopeptidases," Protein Expr Purif. 15(3):389-400 (1999).
Pfeifer et al., "Intestinal secretory defects and dwarfism in mice lacking cGMP-dependent protein kinase II," Science. 274:2082-2086 (1996).
Phillips et al., "A modified performance-oriented mobility assessment tool for assessing clinically relevant gait impairments and change in children with hypophosphatasia: development and validation," Bone Abstracts 4 P136 (2015).
Phillips et al., "Gait assessment in children with childhood hypophosphatasia: impairments in muscle strength and physical function," The Endocrine Society's 97th Annual Meeting & Expo, Mar. 5-8, 2015, San Diego, California (2 pages).
Potter et al., "Natriuretic peptides, their receptors, and cyclic guanosine monophosphate-dependent signaling functions," Endocr Rev. 27(1):47-72 (2006).
Ramachandran et al., "Treatment of an anabolic bone deficiency in neurofibromatosis with bone morphogenetic proteins and its potential application for congenital pseudarthrosis of the tibia," J Bone Joint Surg Br. 91-B (Suppl. 1), Abstract 137 (2009).
Ratner, "Alexion pays big for Synageva's rare disease drug candidate," Nat Biotechnol. 33(7):679 (2015).
Rezende et al., "Inorganic pyrophosphate-phosphohydrolytic activity associated with rat osseous plate alkaline phosphatase," Cell Mol Biol. 44(2):293-302 (1998).
Rowe et al., "MEPE, a new gene expressed in bone marrow and tumors causing osteomalacia," Genomics. 67:54-68 (2000).
Russell et al., "Inorganic pyrophosphate in plasma in normal persons and in patients with hypophosphatasia, osteogenesis imperfecta, and other disorders of bone," J Clin Invest. 50:961-969 (1971).
Salih et al., "Identification of the phosphorylated sites of metabolically 32P-labeled osteopontin from cultured chicken osteoblasts," J Biol Chem. 272(21):13966-73 (1997).
Sands et al., "Enzyme replacement therapy for murine mucopolysaccharidosis type VII," J Clin Invest. 93(6):2324-31 (1994).
Schindeler et al., "Modeling bone morphogenetic protein and bisphosphonate combination therapy in wild-type and Nf1 haploinsufficient mice," J Orthop Res. 26(1):65-74 (2008).
Sekido et al., "Novel drug delivery system to bone using acidic oligopeptide: pharmacokinetic characteristics and pharmacological potential," J Drug Target. 9(2):111-21 (2001).
Sharom et al., "Glycosylphosphatidylinositol-anchored proteins: structure, function, and cleavage by phosphatidylinositol-specific phospholipase C," Biochem Cell Biol. 80:535-549 (2002).
Shukla et al., "RNA interference and inhibition of MEK-ERK signaling prevent abnormal skeletal phenotypes in a mouse model of craniosynostosis," Nat Genet. 39(9):1145-1150 (2007).
Shull et al., "Enzyme replacement in a canine model of hurler syndrome," Proc Natl Acad Sci USA. 91:12937-12941 (1994).
Siris et al., "Paget's disease of bone," Trends Endocrinol Metab. 2(6):207-12 (1991).
Skolnick et al., "From genes to protein structure and function: novel applications of computational approaches in the genomic era," Trends Biotechnol. 18(1):34-9 (2000).
Spears et al., "Deoxyuridylate effects on thymidylate synthase-5-fluorodeoxyuridylate-folate ternary complex formation," Biochem Pharmacol. 38:2985-2993 (1989).

(56) References Cited

OTHER PUBLICATIONS

Srinivas, et al., "Assessment of dose proportionality, absolute bioavailability, and immunogenicity response of CTLA4lg (BMS-188667), a novel immunosuppressive agent, following subcutaneous and intravenous administration to rats," Pharmaceutical Res. 14(7): 911-916 (1997).
Stahl et al., "Evidence for receptor-mediated binding of glycoproteins, glycoconjugates, and lysosomal glycosidases by alveolar macrophages," Proc Natl Acad Sci USA. 75(3):1399-1403 (1978).
Alexion Pharma Interlational, "Strensiq Product Monograph," <http://alexionpharma.ca/documents/Strensiq-PM-asfotase-alfa-14Aug2015.aspx>, Prepared Aug. 14, 2015 (32 pages).
Sturtz et al., "A study of the delivery-targeting concept applied to antineoplasic drugs active on human osteosarcoma. I. Synthesis and biological activity in nude mice carrying human osteosarcoma xenografts of gem-bisphosphonic methotrexate analogues," Eur J Med Chemistry. 27:825-33 (1992).
Suda et al., "C-type natriuretic peptide as an autocrine/paracrine regulator of osteoblast: evidence for possible presence of bone natriuretic peptide system," Biochem Biophys Res Commun. 223:1-6 (1996).
Symersky et al., "Structure of the collagen-binding domain from a *Staphylococcus aureus* adhesin," Nat Struct Biol. 4(10):833-838 (1997).
Takano et al., "Molecular evolution of shark C-type natriuretic peptides," Zoolog Sci. 11:451-454 (1994).
Tamura et al., "Critical roles of the guanylyl cyclase B receptor in endochondral ossification and development of female reproductive organs," Proc Natl Acad Sci USA. 101(49):17300-17305 (2004).
Teixeira et al., "Nitric oxide, C-type natriuretic peptide and cGMP as regulators of endochondral ossification," Dev Biol. 319:171-178 (2008).
Tomatsu, Declaration Under 37 C.F.R. § 1.132 for U.S. Appl. No. 11/484,870, dated Jun. 1, 2009 (3 pages).
Tomatsu, Declaration Under 37 C.F.R. § 1.132 for U.S. Appl. No. 11/484,870, dated Nov. 27, 2007 (2 pages).
Tsuji et al., "A loss-of-function mutation in natriuretic peptide receptor 2 (Npr2) gene is responsible for disproportionate dwarfism in cn/cn mouse," J Biol Chem. 280(14):14288-14292 (2005).
Tye et al., "Delineation of the hydroxyapatite-nucleating domains of bone sialoprotein," J Biol Chem. 278(10):7949-7955 (2003).
Uludag et al., "Bone affinity of a bisphosphonate-conjugated protein in vivo," Biotechnol Prog. 16(6):1115-8 (2000).
Urlaub et al., "Deletion of the diploid dihydrofolate reductase locus from cultured mammalian cells," Cell. 33:405-412 (1983).
"View of NCT02235493 on Nov. 19, 2015," ClinicalTrials.gov archive, Nov. 19, 2015 (4 pages).
Wang et al., "A mouse model for achondroplasia produced by targeting fibroblast growth factor receptor 3," Proc Natl Acad Sci USA. 96:4455-4460 (1999).
Wang et al., "Mice lacking Nf1 in osteochondroprogenitor cells display skeletal dysplasia similar to patients with neurofibromatosis type 1," Hum Mol Genet. 20(20):3910-3924 (2011).
Wang et al., "Structure-based chemical modification strategy for enzyme replacement treatment of phenylketonuria," Mol Genet Metab. 86:134-140 (2005).
Waymire et al., "Mice lacking tissue non-specific alkaline phosphatase die from seizures due to defective metabolism of vitamin B-6," Nat Genet. 11(1):45-51 (1995).
Weinberg, "An overview of infliximab, etanercept, efalizumab, and alefacept as biologic therapy for psoriasis," Clin Ther. 25(10):2487-505 (2003).
Weiss et al., "A missense mutation in the human liver/bone/kidney alkaline phosphatase gene causing a lethal form of hypophosphatasia," Proc Natl Acad Sci USA. 85:7666-7669 (1988).
Weiss et al., "Isolation and characterization of a cDNA encoding a human liver/bone/kidney-type alkaline phosphatase," Proc Natl Acad Sci USA. 83(19):7182-6 (1986).
Weiss et al., "Structure of the human liver/bone/kidney alkaline phosphatase gene," J Biol Chem. 263(24):12002-10 (1988).
Weninger et al., "Biochemical and morphological effects of human hepatic alkaline phosphatase in a neonate with hypophosphatasia," Acta Paediatr Scand. Suppl. 360:154-160 (1989).
Whyte et al., "Alkaline phosphatase: placental and tissue-nonspecific isoenzymes hydrolyze phosphoethanolamine, inorganic pyrophosphate, and pyridoxal 5'-phosphate. Substrate accumulation in carriers of hypophosphatasia corrects during pregnancy," J Clin Invest. 95(4):1440-5 (1995).
Whyte et al., "Enzyme replacement therapy for infantile hypophosphatasia attempted by intravenous infusions of alkaline phosphatase-rich Paget plasma: results in three additional patients," J Pediatr. 105(6):926-33 (1984).
Whyte et al., "Enzyme-replacement therapy in life-threatening hypophosphatasia," N Engl J Med. 366(10):904-13 (2012).
Whyte et al., "Heritable Forms of Rickets and Osteomalacia," in Connective Tissues and Its Heritable Disorders, pp. 765-787, 2002 (eds. R.M. Royce and B. Steinmann, Wiley-Liss, Inc. Hoboken).
Whyte et al., "Hypophosphatasia," in The Metabolic and Molecular Bases of Inherited Disease (8th ed.), pp. 5313-5329, 2001 (McGraw-Hill Book Company) (epub pp. 1-41).
Whyte, "Hypophosphatasia and the role of alkaline phosphatase in skeletal mineralization," Endocr Rev. 15(4):439-461 (1994).
Whyte, Hypophosphatasia: Nature's window on alkaline phosphatase function in man, *Principles of Bone Biology, 2nd ed.*, Bilezikian, Raisz, and Rodan. 2:1229-1248 (2002).
Whyte et al., "Infantile hypophosphatasia: normalization of circulating bone alkaline phosphatase activity followed by skeletal remineralization. Evidence for an intact structural gene for tissue nonspecific alkaline phosphatase," J Pediatr. 108(1):82-8 (1986).
Whyte et al., "Infantile hypophosphatasia: enzyme replacement therapy by intravenous infusion of alkaline phosphatase-rich plasma from patients with Paget bone disease," J Pediatr. 101(3):379-86 (1982).
Whyte et al., "Markedly increased circulating pyridoxal-5'-phosphate levels in hypophosphatasia," J Clin Invest. 76:752-756 (1985).
Whyte et al., "Marrow cell transplantation for infantile hypophosphatasia," J Bone Miner Res. 18(4):624-36 (2003).
Williams et al., "Solute transport in growth plate cartilage: In vitro and in vivo," Biophys J. 93(3):1039-1050 (2007).
Wroblewski et al., "Pharmacokinetics, metabolic stability, and subcutaneous bioavailability of a genetically engineered analog of DcR3, flint [DcR3(R218Q)], in cynomolgus monkeys and mice," Drug Metab Dispos. 31(4):502-507 (2003).
Yadav et al., "Dose response of bone-targeted enzyme replacement for murine hypophosphatasia," available in PMC Aug. 1, 2012, published in final edited form as: Bone. 49(2):250-6 (2011) (20 pages).
Yamamoto et al., "Long term phenotypic correction of severe infantile hypophosphatasia in a mouse model by neonatal injection of lentiviral vector," Mol Ther. 17:S67-S68, Abstract 171 (2009).
Yamamoto et al., "Prolonged survival and phenotypic correction of Akp2(-/-) hypophosphatasia mice by lentiviral gene therapy," J Bone Miner Res. 26(1):135-42 (2011).
Yasoda et al., "Natriuretic peptide regulation of endochondral ossification. Evidence for possible roles of the C-type natriuretic peptide/guanylyl cyclase-B pathway," J Biol Chem. 273(19):11695-11700 (1998).
Yasoda et al., "Overexpression of CNP in chondrocytes rescues achondroplasia through a MAPK-dependent pathway," Nat Med. 10(1):80-86, 2004.
Yasoda et al., "Systemic administration of C-type natriuretic peptide as a novel therapeutic strategy for skeletal dysplasias," Endocrinology. 150(7):3138-3144 (2009).
Yoder et al., "Reduced ability of C-type natriuretic peptide (CNP) to activate natriuretic peptide receptor B (NPR-B) causes dwarfism in Ibab -/- mice," Peptides. 29:1575-1581 (2008).
Yokogawa et al., "Selective delivery of estradiol to bone by aspartic acid oligopeptide and its effects on ovariectomized mice," Endocrinology. 142(3):1228-1233 (2001).
Young et al., "Structure, expression, and regulation of the major noncollagenous matrix proteins of bone," Clin Orthop Relat Res. 281:275-294 (1992).

(56) References Cited

OTHER PUBLICATIONS

Zierhut et al., "Population PK-PD model for Fc-osteoprotegerin in healthy postmenopausal women," J Pharmacokinet Pharmacodyn. 35:379-399 (2008).
Zurutuza et al., "Correlations of genotype and phenotype in hypophosphatasia," Hum Mol Genet. 8(6):1039-1046 (1999).
Office Action for U.S. Appl. No. 11/484,870, dated Jan. 25, 2007 (15 pages).
Office Action for U.S. Appl. No. 11/484,870, dated Jul. 5, 2007 (13 pages).
Office Action for U.S. Appl. No. 11/484,870, dated Oct. 1, 2007 (12 pages).
Office Action for U.S. Appl. No. 11/111,664, dated Oct. 4, 2007 (11 pages).
Office Action for U.S. Appl. No. 11/111,664, dated May 14, 2008 (8 pages).
Office Action for U.S. Appl. No. 11/484,870, dated Jun. 25, 2008 (16 pages).
Office Action for U.S. Appl. No. 11/111,664, dated Dec. 4, 2008 (7 pages).
Office Action for U.S. Appl. No. 11/484,870, dated Feb. 2, 2009 (16 pages).
Office Action for U.S. Appl. No. 11/484,870, dated Aug. 11, 2009 (15 pages).
Office Action for U.S. Appl. No. 12/405,920, dated Dec. 17, 2009 (14 pages).
Office Action for U.S. Appl. No. 12/405,920, dated Aug. 9, 2010 (7 pages).
Office Action for U.S. Appl. No. 12/793,517, dated Aug. 16, 2010 (16 pages).
Office Action for U.S. Appl. No. 13/071,445, dated Feb. 6, 2012 (22 pages).
Office Action for U.S. Appl. No. 13/071,445, dated May 25, 2012 (14 pages).
Official Notification and Search Report for Eurasian Patent Application No. 201291138, dated May 17, 2013 (3 pages).
Reply to Final Office Action for U.S. Appl. No. 13/071,445, dated Oct. 25, 2012 (14 pages).
Reply to Office Action for U.S. Appl. No. 11/111,664, dated Sep. 10, 2008 (32 pages).
Restriction Requirement for U.S. Appl. No. 12/599,679, dated Jun. 12, 2012 (5 pages).
Supplementary European Search Report for European Application No. EP 05739065, date of completion Nov. 7, 2008 (2 pages).
Supplementary European Search Report for European Application No. EP 08757088, date of completion Jun. 7, 2010 (5 pages).
Supplementary European Search Report for European Patent Application No. 08757088.3, dated Jun. 21, 2010 (7 pages).
Supplementary European Search Report for European Patent Application No. 11853820.6, dated Mar. 25, 2014 (3 pages).
International Preliminary Report on Patentability for International Patent Application No. PCT/US2012/060869, dated Apr. 22, 2014 (7 pages).
International Preliminary Report on Patentability for International Patent Application No. PCT/US2012/039004, dated Apr. 22, 2014 (8 pages).
International Search Report and Writen Opinion for International Applicaiton No. PCT/CA2011/050807, dated Apr. 13, 2012 (18 pages).
Barcia et al., "Infantile hypophosphatasia: treatment options to control hypercalcemia, hypercalciuria, and chronic bone demineralization," J Pediatr. 130(5):825-8 (1997).
Barvencik et al., "Skeletal mineralization defects in adult hypophosphatasia—a clinical and histological analysis," Osteoporosis Int. 22(10):2667-75 (2011).
Baumgartner-Sigl et al., "Pyridoxine-responsive seizures as the first symptom of infantile hypophosphatasia caused by two novel missense mutations (c.677T>C, p. M226T; c.1112C>T, p. T371I) of the tissue-nonspecific alkaline phosphatase gene," Bone. 40(6):1655-61 (2007).

Beck et al., "Whole-body MRI in the childhood form of hypophosphatasia," Rheumatol Int. 31(10):1315-20 (2011).
Beederman et al., "Molecular basis of cranial suture biology and disease: osteoblastic and osteoclastic perspectives," Genes Dis. 1(1):120-5 (2014).
Boulet et al., "A population-based study of craniosynostosis in metropolitan Atlanta, 1989-2003," Am J Med Genet A. 146A(8):984-91 (2008).
Chan et al., "Endoscope-assisted versus open repair of craniosynostosis: a comparison of perioperative cost and risk," J Craniofac Surg. 24(1):170-4 (2013).
Choi et al., "Craniosynostosis in growing children: pathophysiological changes and neurosurgical problems," J Korean Neurosurg Soc. 59(3):197-203 (2016).
Chong et al., "Minimally invasive suturectomy and postoperative helmet therapy: advantages and limitations," J Korean Neurosurg Soc. 59(3):227-32 (2016).
Clarke, "Normal bone anatomy and physiology," Clin J Am Soc Nephrol. 3(Suppl 3):S131-9 (2008).
Colantonio et al., "Closing the gaps in pediatric laboratory reference intervals: a CALIPER database of 40 biochemical markers in a healthy and multiethnic population of children," Clin Chem. 58(5):854-68 (2012).
Collmann et al., "Neurosurgical aspects of childhood hypophosphatasia," Childs Nerv Syst. 25(2):217-23 (2009).
Czerwinski et al., "Major morbidity and mortality rates in craniofacial surgery: an analysis of 8101 major procedures," Plast Reconstr Surg. 126(1):181-6 (2010).
Eade et al., "Pyrophosphate arthropathy in hypophosphatasia," Ann Rheum Dis. 40(2):164-70 (1981).
Esparza et al., "Complications in the surgical treatment of craniosynostosis and craniofacial syndromes: apropos of 306 transcranial procedures," Childs Nerv Syst. 24(12):1421-30 (2008).
Esparza et al., "Surgical treatment of isolated and syndromic craniosynostosis. Results and complications in 283 consecutive cases," Neurocirugía. 19(6):509-29 (2008).
Fraser, "Hypophosphatasia," Am J Med. 22(5):730-46 (1957).
Garber et al., "Comparing outcomes and cost of 3 surgical treatments for sagittal synostosis: a retrospective study including procedure-related cost analysis," Neurosurgery. 81(4):680-7 (2017).
Ginelliová et al., "Sudden death associated with syndromic craniosynostosis," Forensic Sci Med Pathol. 12(4):506-9 (2016).
Greenwood et al., "Familial incidence and associated symptoms in a population of individuals with nonsyndromic craniosynostosis," Genet Med. 16(4):302-10 (2014).
Guañabens et al., "Calcific periarthritis as the only clinical manifestation of hypophosphatasia in middle-aged sisters," J Bone Miner Res. 29(4):929-34 (2014).
Herring, "Mechanical influences on suture development and patency," Front Oral Biol. 12:41-56 (2008).
Hollis et al., "Current concepts in hypophosphatasia: case report and literature review," Int J Paediatr Dent. 23(3):153-9 (2013).
Hwang et al., "Update of diagnostic evaluation of craniosynostosis with a focus on pediatric systematic evaluation and genetic studies," J Korean Neurosurg Soc. 59(3):214-8 (2016).
Johnson et al., "Craniosynostosis," Eur J Hum Genet. 19(4):369-76 (2011).
Kabbani et al., "Craniosynostosis," Am Fam Physician. 69(12):2863-70 (2004).
Katsianou et al., "Signaling mechanisms implicated in cranial sutures pathophysiology: Craniosynostosis," BBA Clin. 6:165-76 (2016).
Khanna et al., "Pictorial essay: the many faces of craniosynostosis," Indian J Radiol J. 21(1):49-56 (2011).
Kim et al., "Craniosynostosis: Updates in radiologic diagnosis," J Korean Neurosurg Soc. 59(3):219-26 (2016).
Kozlowski et al., "Hypophosphatasia. Review of 24 Cases," Pediatr Radiol. 5(2):103-17 (1976) (15 pages).
Krakow et al., "Clinical and radiographic delineation of bent bone dysplasia-FGFR2 type or bent bone dysplasia with distinctive clavicles and angel-shaped phalanges," Am J Med Genet A. 170(10):2652-61 (2016).

(56) References Cited

OTHER PUBLICATIONS

Mathijssen, "Guideline for care of patients with the diagnoses of craniosynostosis: working group on craniosynostosis," J Craniofac Surg. 26(6):1735-807 (2015).
Merrill et al., "Bent bone dysplasia-FGFR2 type, a distinct skeletal disorder, has deficient canonical FGF signaling," Am J Hum Genet. 90(3):550-7 (2012).
Milián, "The role of phosphatases in the initiation of skeletal mineralization," Calcif Tissue Int. 93(4):299-306 (2013).
Miller et al., "Ultrasound diagnosis of craniosynostosis," Cleft Palate Craniofac J. 39(1):73-80 (2002).
Millichap, "Cognitive Development of Children with Craniosynostosis," Pediatr Neurol Briefs. 29(6):47 (2015).
Mohn et al., "Hypophosphatasia in a child with widened anterior fontanelle: lessons learned from late diagnosis and incorrect treatment," Acta Paediatr. 100(7):e43-6 (2011).
Mornet et al., "A molecular-based estimation of the prevalence of hypophosphatasia in the European population," Ann Hum Genet. 75(3):439-45 (2011).
Nakamura-Utsunomiya et al., "Clinical characteristics of perinatal lethal hypophosphatasia: a report of 6 cases," Clin Pediatr Endocrinol. 19(1):7-13 (2010).
Oginni et al., "Radiological and biochemical resolution of nutritional rickets with calcium," Arch Dis Child. 88(9):812-17 (2003).
Opperman, "Cranial sutures as intramembranous bone growth sites," Dev Dyn. 219(4):472-85 (2000).
Reginato et al., "Musculoskeletal manifestations of osteomalacia and rickets," Best Pract Res Clin Rheumatol. 17(6):1063-80 (2003).
Rodgers et al., "Spring-assisted cranioplasty for the correction of non-syndromic scaphocephaly: a quantitative analysis of 100 consecutive cases," Plast Reconstr Surg. 140(1):125-34 (2017).
Rottgers et al., "Outcomes of endoscopic suturectomy with postoperative helmet therapy in bilateral coronal craniosynostosis," J Neurosurg Pediatr. 18(3):281-6 (2016).
Rozovsky et al., "Cranial ultrasound as a first-line imaging examination for craniosynostosis," Pediatrics. 137(2):e20152230 (2016) (9 pages).
Sabbagh et al., "Hypophosphatemia leads to rickets by impairing caspase-mediated apoptosis of hypertrophic chondrocytes," Proc Natl Acad Sci U S A. 102(27):9637-42 (2005).
Sakamoto et al., "Physiological changes and clinical implications of syndromic craniosynostosis," J Korean Neurosurg Soc. 59(3):204-13 (2016).
Salva et al., "Signaling networks in joint development," Dev Dyn. 246(4):262-74 (2017).
Seshia et al., "Myopathy with hypophosphatasia," Arch Dis Child. 65(1):130-1 (1990).
Shah et al., "Sudden infant death in a patient with FGFR3 P250R mutation," Am J Med Genet A. 140A(24):2794-6 (2006).
Sharma et al., "Bilateral femoral neck fractures in a young patient suffering from hypophosphatasia, due to a first time epileptic seizure," J Orthop Case Rep. 5(3):66-8 (2015).
Sharma, "Craniosynostosis," Indian J Plast Surg. 46(1):18-27 (2013).
Silver et al., "Pulmonary hypoplasia in neonatal hypophosphatasia," Pediatr Pathol. 8(5):483-93 (1988) (12 pages).
Thacher et al., "Radiographic scoring method for the assessment of the severity of nutritional rickets," J Trop Pediatr. 46(3):132-9 (2000).
Thurner et al., "Osteopontin deficiency increases bone fragility but preserves bone mass," Bone. 46(6):1564-73 (2010).
Tokumaru et al., "Skull base and calvarial deformities: association with intracranial changes in craniofacial syndromes," Am J Neuroradiol. 17(4):619-30 (1996).
Watanabe et al., "Prevalence of c.1559delT in ALPL, a common mutation resulting in the perinatal (lethal) form of hypophosphatasia in Japanese and effects of the mutation on heterozygous carriers," J Hum Genet. 56(2):166-8 (2011).
Whyte et al., "Adult hypophosphatasia with chondrocalcinosis and arthropathy: variable penetrance of hypophosphatasemia in a large Oklahoma kindred," Am J Med. 72(4):631-41 (1982).

Whyte et al., "Adult hypophosphatasia treated with teriparatide," J Clin Endocrinol Metab. 92(4):1203-8 (2007).
Whyte et al., "Rickets and osteomalacia," Medicine. 37(9):483-8 (2009).
Zaleckas et al., "Diagnosis and treatment of craniosynostosis: Vilnius team experience," Acta Med Litu. 22(2):111-21 (2015).
Anderson, "Mechanism of Mineral Formation in Bone," *Pathology Reviews*. Emanuel Rubin and Ivan Damjanov (eds.), 13-23 (1990).
Whyte, Chapter 73: Hypophosphatasia: Nature's Window on Alkaline Phosphatase Function in Humans, *Principles of Bone Biology*, vol. 1, Third Edition. John P. Bilezikian, Lawrence G. Raisz and T. John Martin (eds.), 1573-98 (2008).
Whyte, Chapter 22: Hypophosphatasia, *Genetics of Bone Biology and Skeletal Disease*. Rajesh V. Thakker, Michael P. Whyte, John A. Eisman and Takashi Igarashi (eds.), 337-360 (2013).
Del Angel et al., "Birth prevalence estimation of severe Hypophosphatasia in European populations using large-scale protein-coding genetic variation databases," American Society of Human Genetics 66th Annual Meeting, Oct. 18-22, Vancouver, Canada. Poster abstract 1670T (2016) (2 pages).
Rockman-Greenberg et al., "Hypophosphatasia: Enzyme Replacement with ENB-0040, a Bone-Targeted Human Recombinant Tissue Nonspecific Alkaline Phosphatase (TNSALP) Fusion Protein," American College of Medical Genetics, 16th Annual Clinical Genetics Meeting, Mar. 25-29, Tampa, Florida (2009) (1 page).
Simmons, "Best Practices In: Recognizing and Diagnosing Hypophosphatasia," Clinical Endocrinology News. <https://www.mdedge.com/sites/default/files/issues/articles/Alexion_10_11_Final_Web.pdf>, published Sep. 30, 2013, retrieved on Mar. 27, 2019 (8 pages).
Weber et al., "Burden of disease in children with hypophosphatasia: results from patient-reported surveys," 7th International Conference on Children's Bone Health, Jun. 27-30, Salzburg, Austria. *Bone Abstracts*. 4: P119 (2015) (3 pages).
Whyte et al., "Asfotase alfa: Sustained Efficacy and Tolerability in Infants and Young Children with Life-Threatening Hypophosphatasia," 2014 Pediatric Academic Societies and Asian Society for Pediatric Research Joint Meeting, May 3-6, Vancouver, BC, Canada. Poster 69 (2014) (1 page).
Whyte et al., "Hypophosphatasia: A Retrospective Natural History Study of the Severe Perinatal and Infantile Forms," 2014 European Calcified Tissue Society Congress, May 17-20, Prague, Czech Republic. Poster P364 (2014) (1 page).
Whyte et al., "A retrospective, multi-national, non-interventional, natural history study of the childhood form of hypophosphatasia," ENDO 2015: The Endocrine Society Annual Meeting, Mar. 5-8, San Diego, California. Abstract LB-OR01-4 (2015) (2 pages).
Stoll et al., "Severe hypophosphatasia due to mutations in the tissue-nonspecific alkaline phosphatase (TNSALP) gene," Genet Couns. 13(3):289-95 (2002).
Mornet, "Hypophosphatasia," Best Pract Res Clin Rheumatol. 22(1):113-27 (2008).
Kajdic et al., "Craniosynostosis—Recognition, clinical characteristics, and treatment," Bosn J Basic Med Sci. 18(2):110-6 (2018).
Dortschy et al., "Bevölkerungsbezogene verteilungswerte ausgewählter laborparameter aus der studie zur gesundheit von kindern und jugendlichen in Deutschland (KiGGS)," Gesundheitsberichterstattung des Bundes, Robert Koch Institute (2009) (136 pages).
Communication pursuant to Rule 164(2)(b) and Article 94(3) EPC for European Application No. 16707571.2, dated Feb. 26, 2019 (12 pages).
Fong et al., "Hypocalcemia: Updates in diagnosis and management for primary care," Can Fam Physician. 58(2):158-62 (2012).
Makras et al., "Medical treatment of Hypercalcaemia," Hormones. 8(2):83-95 (2009).
Extended European Search Report for European Application No. 15907550.6, dated Jun. 4, 2019 (7 pages).
Carden et al., "Tracheomalacia and tracheobronchomalacia in children and adults: an in-depth review," Chest. 127(3):984-1005 (2005) (22 pages).
Hancarova et al., "Hypophosphatasia due to uniparental disomy," Bone. 81:765-766 (2015) (2 pages).

(56) References Cited

OTHER PUBLICATIONS

International Search Report and Written Opinion for International Application No. PCT/US2019/045963, dated Jan. 30, 2020 (26 pages).

Leung et al., "Outcome of perinatal hypophosphatasia in Manitoba Mennonites: a retrospective cohort analysis," JIMD Rep. 11:73-78 (2013) (6 pages).

Li et al., "Timing of the initiation of bisphosphonates after surgery for fracture healing: a systematic review and meta-analysis of randomized controlled trials," Osteoporos Int. 26(2):431-41 (2015) (11 pages).

Mornet, "The tissue nonspecific alkaline phosphatase gene mutations database," <www.sesep.uvsq.fr/03_hypo_mutations.php>, last updated Nov. 28, 2019 (14 pages).

Morrison et al., "Mitigation of tracheobronchomalacia with 3D-printed personalized medical devices in pediatric patients," available in PMC Apr. 29, 2016, published in final edited form as: Sci Transl Med. 7(285):285ra264 (2015) (23 pages).

Murgu et al., "Tracheobronchomalacia and excessive dynamic airway collapse," Respirology. 11(4):388-406 (2006) (19 pages).

Official Action and Translation for Japanese Application No. 2017-539393, dated Sep. 17, 2019 (14 pages).

Park et al., "The effect of alendronate loaded biphasic calcium phosphate scaffolds on bone regeneration in a rat tibial defect model," Int J Mol Sci. 16(11):26738-53 (2015) (17 pages).

Rodionova et al., "Hypophosphatasia in adults: clinical cases and literature review," Osteoporosis and Bone Diseases. 18(2):25-7 (2015) (4 pages).

Search Report and Translation for Russian Application No. 2018109368, dated Feb. 5, 2020 (4 pages).

Taketani et al., Chapter 9: Hypophosphatasia. *Human Pathobiochemistry*. T. Oohashi et al. (eds.), 91-100 (2019) (10 pages).

Wang et al., "The effects of tissue-non-specific alkaline phosphatase gene therapy on craniosynostosis and craniofacial morphology in the FGFR2$^{C342Y/+}$ mouse model of Crouzon craniosynostosis," Orthod. Craniofac Res. 18:196-206 (2015) (11 pages).

Whyte et al., "Asfotase alfa for infants and young children with hypophosphatasia: 7 year outcomes of a single-arm, open-label, phase 2 extension trial," Lancet Diabetes Endocrinol. 7(2):93-105 (2019) (52 pages).

Whyte et al., "Hypophosphatasia (HPP) in children: enzyme replacement therapy (EzRT) using bone-targeted, tissue-nonspecific alkaline phosphatase (TNSALP)," Ann Neurol. 68(Suppl 14):S70 Abstract WIP-28 (2010) (1 page).

Whyte et al., "Natural history of perinatal and infantile hypophosphatasia: a retrospective study," J Pediatr. 209:116-124.e4 (2019) (13 pages).

\* cited by examiner

FIG. 12

SEQ ID NO: 1 (TNALP nucleic acid sequence)

| | |
|---|---|
| ggatccacca tgatttcacc attcttagta ctggccattg gcacctgcct tactaactcc | 60 |
| ttagtgccag agaaagagaa agaccccaag tactggcgag accaagcgca agagacactg | 120 |
| aaatatgccc tggagcttca gaagctcaac accaacgtgg ctaagaatgt catcatgttc | 180 |
| ctgggagatg ggatgggtgt ctccacagtg acggctgccc gcatcctcaa gggtcagctc | 240 |
| caccacaacc ctggggagga gaccaggctg gagatggaca agttccccctt cgtggccctc | 300 |
| tccaagacgt acaacaccaa tgcccaggtc cctgacagcg ccggcaccgc caccgcctac | 360 |
| ctgtgtgggg tgaaggccaa tgagggcacc gtggggggtaa gcgcagccac tgagcgttcc | 420 |
| cggtgcaaca ccacccaggg gaacgaggtc acctccatcc tgcgctgggc caaggacgct | 480 |
| gggaaatctg tgggcattgt gaccaccacg agagtgaacc atgccacccc cagcgccgcc | 540 |
| tacgcccact cggctgaccg ggactggtac tcagacaacg agatgccccc tgaggccttg | 600 |
| agccagggct gtaaggacat cgcctaccag ctcatgcata acatcaggga cattgacgtg | 660 |
| atcatggggg gtggccggaa atacatgtac cccaagaata aaactgatgt ggagtatgag | 720 |
| agtgacgaga agccaggggg cacgaggctg gacggcctgg acctcgttga cacctggaag | 780 |
| agcttcaaac cgagatacaa gcactcccac ttcatctgga accgcacgga actcctgacc | 840 |
| cttgaccccc acaatgtgga ctacctattg ggtctcttcg agccagggga catgcagtac | 900 |
| gagctgaaca ggaacaacgt gacggacccg tcactctccg agatggtggt ggtggccatc | 960 |
| cagatcctgc ggaagaaccc caaaggcttc ttcttgctgg tggaaggagg cagaattgac | 1020 |
| cacgggcacc atgaaggaaa agccaagcag gccctgcatg aggcggtgga gatggaccgg | 1080 |
| gccatcgggc aggcaggcag cttgacctcc tcggaagaca ctctgaccgt ggtcactgcg | 1140 |
| gaccattccc acgtcttcac atttggtgga tacaccccccc gtggcaactc tatctttggt | 1200 |
| ctggccccca tgctgagtga cacagacaag aagccccttca ctgccatcct gtatggcaat | 1260 |
| gggcctggct acaaggtggt gggcggtgaa cgagagaatg tctccatggt ggactatgct | 1320 |
| cacaacaact accaggcgca gtctgctgtg ccctgcgcc acgagaccca cggcggggag | 1380 |

FIG. 12 (CONT'D)

gacgtggccg tcttctccaa gggccccatg gcgcacctgc tgcacggcgt ccacgagcag 1440
aactacgtcc cccacgtgat ggcgtatgca gcctgcatcg gggccaacct cggccactgt 1500
gctcctgcca gctcgtagtc taga

SEQ ID NO: 2: (TNALP amino acid sequence)
Met Ile Ser Pro Phe Leu Val Leu Ala Ile Gly Thr Cys Leu Thr Asn
Ser Leu Val Pro Glu Lys Glu Lys Asp Pro Lys Tyr Trp Arg Asp Gln
Ala Gln Glu Thr Leu Lys Tyr Ala Leu Glu Leu Gln Lys Leu Asn Thr
Asn Val Ala Lys Asn Val Ile Met Phe Leu Gly Asp Gly Met Gly Val
Ser Thr Val Thr Ala Ala Arg Ile Leu Lys Gly Gln Leu His His Asn
Pro Gly Glu Glu Thr Arg Leu Glu Met Asp Lys Phe Pro Phe Val Ala
Leu Ser Lys Thr Tyr Asn Thr Asn Ala Gln Val Pro Asp Ser Ala Gly
Thr Ala Thr Ala Tyr Leu Cys Gly Val Lys Ala Asn Glu Gly Thr Val
Gly Val Ser Ala Ala Thr Glu Arg Ser Arg Cys Asn Thr Thr Gln Gly
Asn Glu Val Thr Ser Ile Leu Arg Trp Ala Lys Asp Ala Gly Lys Ser
Val Gly Ile Val Thr Thr Thr Arg Val Asn His Ala Thr Pro Ser Ala
Ala Tyr Ala His Ser Ala Asp Arg Asp Trp Tyr Ser Asp Asn Glu Met
Pro Pro Glu Ala Leu Ser Gln Gly Cys Lys Asp Ile Ala Tyr Gln Leu
Met His Asn Ile Arg Asp Ile Asp Val Ile Met Gly Gly Gly Arg Lys
Tyr Met Tyr Pro Lys Asn Lys Thr Asp Val Glu Tyr Glu Ser Asp Glu
Lys Ala Arg Gly Thr Arg Leu Asp Gly Leu Asp Leu Val Asp Thr Trp
Lys Ser Phe Lys Pro Arg Tyr Lys His Ser His Phe Ile Trp Asn Arg
Thr Glu Leu Leu Thr Leu Asp Pro His Asn Val Asp Tyr Leu Leu Gly
Leu Phe Glu Pro Gly Asp Met Gln Tyr Glu Leu Asn Arg Asn Asn Val
Thr Asp Pro Ser Leu Ser Glu Met Val Val Val Ala Ile Gln Ile Leu
Arg Lys Asn Pro Lys Gly Phe Phe Leu Leu Val Glu Gly Gly Arg Ile
Asp His Gly His His Glu Gly Lys Ala Lys Gln Ala Leu His Glu Ala
Val Glu Met Asp Arg Ala Ile Gly Gln Ala Gly Ser Leu Thr Ser Ser
Glu Asp Thr Leu Thr Val Val Thr Ala Asp His Ser His Val Phe Thr
Phe Gly Gly Tyr Thr Pro Arg Gly Asn Ser Ile Phe Gly Leu Ala Pro

FIG. 12 (CONT'D)

Met Leu Ser Asp Thr Asp Lys Lys Pro Phe Thr Ala Ile Leu Tyr Gly
Asn Gly Pro Gly Tyr Lys Val Val Gly Gly Glu Arg Glu Asn Val Ser
Met Val Asp Tyr Ala His Asn Asn Tyr Gln Ala Gln Ser Ala Val Pro
Leu Arg His Glu Thr His Gly Gly Glu Asp Val Ala Val Phe Ser Lys
Gly Pro Met Ala His Leu Leu His Gly Val His Glu Gln Asn Tyr Val
Pro His Val Met Ala Tyr Ala Ala Cys Ile Gly Ala Asn Leu Gly His
Cys Ala Pro Ala Ser Ser

SEQ ID NO: 3 (sALP-D10 nucleic acid sequence)

ggatccacca tgatttcacc attcttagta ctggccattg cacctgcct tactaactcc    60 ttagtgccag agaaagagaa agaccccaag tactggcgag accaagcgca agagacactg   120
aaatatgccc tggagcttca gaagctcaac accaacgtgg ctaagaatgt catcatgttc   180
ctgggagatg ggatgggtgt ctccacagtg acggctgccc gcatcctcaa gggtcagctc   240
caccacaacc ctggggagga gaccaggctg gagatggaca agttccccctt cgtggccctc   300 tccaagacgt acaacaccaa tgcccaggtc cctgacagcg ccggcaccgc caccgcctac   360
ctgtgtgggg tgaaggccaa tgagggcacc gtgggggtaa gcgcagccac tgagcgttcc   420
cggtgcaaca ccacccaggg gaacgaggtc acctccatcc tgcgctgggc caaggacgct   480
gggaaatctg tgggcattgt gaccaccacg agagtgaacc atgccacccc cagcgccgcc   540
tacgcccact cggctgaccg ggactggtac tcagacaacg agatgccccc tgaggccttg   600
agccagggct gtaaggacat cgcctaccag ctcatgcata acatcaggga cattgacgtg   660
atcatggggg gtggccggaa atacatgtac cccaagaata aaactgatgt ggagtatgag   720

FIG. 12 (CONT'D)

agtgacgaga aagccagggg cacgaggctg gacggcctgg acctcgttga cacctggaag 780
agcttcaaac cgagatacaa gcactcccac ttcatctgga accgcacgga actcctgacc 840
cttgaccccc acaatgtgga ctacctattg ggtctcttcg agccagggga catgcagtac 900
gagctgaaca ggaacaacgt gacggacccg tcactctccg agatggtggt ggtggccatc 960
cagatcctgc ggaagaaccc caaaggcttc ttcttgctgg tggaaggagg cagaattgac 1020
cacgggcacc atgaaggaaa agccaagcag gccctgcatg aggcggtgga gatggaccgg 1080
gccatcgggc aggcaggcag cttgacctcc tcggaagaca ctctgaccgt ggtcactgcg 1140
gaccattccc acgtcttcac atttggtgga tacccccccc gtggcaactc tatctttggt 1200
ctggccccca tgctgagtga cacagacaag aagcccttca ctgccatcct gtatggcaat 1260
gggcctggct acaaggtggt gggcggtgaa cgagagaatg tctccatggt ggactatgct 1320
cacaacaact accaggcgca gtctgctgtg cccctgcgcc acgagaccca cggcggggag 1380
gacgtggccg tcttctccaa gggccccatg gcgcacctgc tgcacggcgt ccacgagcag 1440
aactacgtcc cccacgtgat ggcgtatgca gcctgcatcg gggccaacct cggccactgt 1500

FIG. 12 (CONT'D)

gctcctgcca gctcggatga cgacgatgat gacgatgatg acgactagtc taga     1554

SEQ ID NO: 4 (sALP-D10 amino acid sequence)

Met Ile Ser Pro Phe Leu Val Leu Ala Ile Gly Thr Cys Leu Thr Asn
Ser Leu Val Pro Glu Lys Glu Lys Asp Pro Lys Tyr Trp Arg Asp Gln
Ala Gln Glu Thr Leu Lys Tyr Ala Leu Glu Leu Gln Lys Leu Asn Thr
Asn Val Ala Lys Asn Val Ile Met Phe Leu Gly Asp Gly Met Gly Val
Ser Thr Val Thr Ala Ala Arg Ile Leu Lys Gly Gln Leu His His Asn
Pro Gly Glu Glu Thr Arg Leu Glu Met Asp Lys Phe Pro Phe Val Ala
Leu Ser Lys Thr Tyr Asn Thr Asn Ala Gln Val Pro Asp Ser Ala Gly
Thr Ala Thr Ala Tyr Leu Cys Gly Val Lys Ala Asn Glu Gly Thr Val
Gly Val Ser Ala Ala Thr Glu Arg Ser Arg Cys Asn Thr Thr Gln Gly
Asn Glu Val Thr Ser Ile Leu Arg Trp Ala Lys Asp Ala Gly Lys Ser
Val Gly Ile Val Thr Thr Thr Arg Val Asn His Ala Thr Pro Ser Ala
Ala Tyr Ala His Ser Ala Asp Arg Asp Trp Tyr Ser Asp Asn Glu Met
Pro Pro Glu Ala Leu Ser Gln Gly Cys Lys Asp Ile Ala Tyr Gln Leu
Met His Asn Ile Arg Asp Ile Asp Val Ile Met Gly Gly Gly Arg Lys
Tyr Met Tyr Pro Lys Asn Lys Thr Asp Val Glu Tyr Glu Ser Asp Glu
Lys Ala Arg Gly Thr Arg Leu Asp Gly Leu Asp Leu Val Asp Thr Trp
Lys Ser Phe Lys Pro Arg Tyr Lys His Ser His Phe Ile Trp Asn Arg
Thr Glu Leu Leu Thr Leu Asp Pro His Asn Val Asp Tyr Leu Leu Gly
Leu Phe Glu Pro Gly Asp Met Gln Tyr Glu Leu Asn Arg Asn Asn Val
Thr Asp Pro Ser Leu Ser Glu Met Val Val Val Ala Ile Gln Ile Leu
Arg Lys Asn Pro Lys Gly Phe Phe Leu Leu Val Glu Gly Gly Arg Ile
Asp His Gly His His Glu Gly Lys Ala Lys Gln Ala Leu His Glu Ala
Val Glu Met Asp Arg Ala Ile Gly Gln Ala Gly Ser Leu Thr Ser Ser
Glu Asp Thr Leu Thr Val Val Thr Ala Asp His Ser His Val Phe Thr
Phe Gly Gly Tyr Thr Pro Arg Gly Asn Ser Ile Phe Gly Leu Ala Pro

FIG. 12 (CONT'D)

Met Leu Ser Asp Thr Asp Lys Lys Pro Phe Thr Ala Ile Leu Tyr Gly
Asn Gly Pro Gly Tyr Lys Val Val Gly Gly Glu Arg Glu Asn Val Ser
Met Val Asp Tyr Ala His Asn Asn Tyr Gln Ala Gln Ser Ala Val Pro
Leu Arg His Glu Thr His Gly Gly Glu Asp Val Ala Val Phe Ser Lys
Gly Pro Met Ala His Leu Leu His Gly Val His Glu Gln Asn Tyr Val
Pro His Val Met Ala Tyr Ala Ala Cys Ile Gly Ala Asn Leu Gly His
Cys Ala Pro Ala Ser Ser Asp Asp Asp Asp Asp Asp Asp Asp Asp Asp

SEQ ID NO: 5 (IgG1-Fc)
Asp Lys Thr His Thr Cys Pro Pro Cys Pro Ala Pro Glu Leu Leu Gly
Gly Pro Ser Val Phe Leu Phe Pro Pro Lys Pro Lys Asp Thr Leu Met
Ile Ser Arg Thr Pro Glu Val Thr Cys Val Val Val Asp Val Ser His
Glu Asp Pro Glu Val Lys Phe Asn Trp Tyr Val Asp Gly Val Glu Val
His Asn Ala Lys Thr Lys Pro Arg Glu Glu Gln Tyr Asn Ser Thr Tyr
Arg Val Val Ser Val Leu Thr Val Leu His Gln Asp Trp Leu Asn Gly
Lys Glu Tyr Lys Cys Lys Val Ser Asn Lys Ala Leu Pro Ala Pro Ile
Glu Lys Thr Ile Ser Lys Ala Lys Gly Gln Pro Arg Glu Pro Gln Val
Tyr Thr Leu Pro Pro Ser Arg Glu Glu Met Thr Lys Asn Gln Val Ser
Leu Thr Cys Leu Val Lys Gly Phe Tyr Pro Ser Asp Ile Ala Val Glu
Trp Glu Ser Asn Gly Gln Pro Glu Asn Asn Tyr Lys Thr Thr Pro Pro
Val Leu Asp Ser Asp Gly Ser Phe Phe Leu Tyr Ser Lys Leu Thr Val
Asp Lys Ser Arg Trp Gln Gln Gly Asn Val Phe Ser Cys Ser Val Met
His Glu Ala Leu His Asn His Tyr Thr Gln Lys Ser Leu Ser Leu Ser
Pro Gly Lys

SEQ ID NO: 6 (hTNALP-Fc-D10)
Met Ile Ser Pro Phe Leu Val Leu Ala Ile Gly Thr Cys Leu Thr Asn
Ser Leu Val Pro Glu Lys Glu Lys Asp Pro Lys Tyr Trp Arg Asp Gln

FIG. 12 (CONT'D)

Ala Gln Glu Thr Leu Lys Tyr Ala Leu Glu Leu Gln Lys Leu Asn Thr
Asn Val Ala Lys Asn Val Ile Met Phe Leu Gly Asp Gly Met Gly Val
Ser Thr Val Thr Ala Ala Arg Ile Leu Lys Gly Gln Leu His His Asn
Pro Gly Glu Glu Thr Arg Leu Glu Met Asp Lys Phe Pro Phe Val Ala
Leu Ser Lys Thr Tyr Asn Thr Asn Ala Gln Val Pro Asp Ser Ala Gly
Thr Ala Thr Ala Tyr Leu Cys Gly Val Lys Ala Asn Glu Gly Thr Val
Gly Val Ser Ala Ala Thr Glu Arg Ser Arg Cys Asn Thr Thr Gln Gly
Asn Glu Val Thr Ser Ile Leu Arg Trp Ala Lys Asp Ala Gly Lys Ser
Val Gly Ile Val Thr Thr Thr Arg Val Asn His Ala Thr Pro Ser Ala
Ala Tyr Ala His Ser Ala Asp Arg Asp Trp Tyr Ser Asp Asn Glu Met
Pro Pro Glu Ala Leu Ser Gln Gly Cys Lys Asp Ile Ala Tyr Gln Leu
Met His Asn Ile Arg Asp Ile Asp Val Ile Met Gly Gly Gly Arg Lys
Tyr Met Tyr Pro Lys Asn Lys Thr Asp Val Glu Tyr Glu Ser Asp Glu
Lys Ala Arg Gly Thr Arg Leu Asp Gly Leu Asp Leu Val Asp Thr Trp
Lys Ser Phe Lys Pro Arg Tyr Lys His Ser His Phe Ile Trp Asn Arg
Thr Glu Leu Leu Thr Leu Asp Pro His Asn Val Asp Tyr Leu Leu Gly
Leu Phe Glu Pro Gly Asp Met Gln Tyr Glu Leu Asn Arg Asn Asn Val
Thr Asp Pro Ser Leu Ser Glu Met Val Val Val Ala Ile Gln Ile Leu
Arg Lys Asn Pro Lys Gly Phe Phe Leu Leu Val Glu Gly Gly Arg Ile
Asp His Gly His His Glu Gly Lys Ala Lys Gln Ala Leu His Glu Ala
Val Glu Met Asp Arg Ala Ile Gly Gln Ala Gly Ser Leu Thr Ser Ser
Glu Asp Thr Leu Thr Val Val Thr Ala Asp His Ser His Val Phe Thr
Phe Gly Gly Tyr Thr Pro Arg Gly Asn Ser Ile Phe Gly Leu Ala Pro
Met Leu Ser Asp Thr Asp Lys Lys Pro Phe Thr Ala Ile Leu Tyr Gly
Asn Gly Pro Gly Tyr Lys Val Val Gly Gly Glu Arg Glu Asn Val Ser
Met Val Asp Tyr Ala His Asn Asn Tyr Gln Ala Gln Ser Ala Val Pro
Leu Arg His Glu Thr His Gly Gly Glu Asp Val Ala Val Phe Ser Lys
Gly Pro Met Ala His Leu Leu His Gly Val His Glu Gln Asn Tyr Val

FIG. 12 (CONT'D)

Pro His Val Met Ala Tyr Ala Ala Cys Ile Gly Ala Asn Leu Gly His
Cys Ala Pro Ala Ser Ser Leu Lys Asp Lys Thr His Thr Cys Pro Pro
Cys Pro Ala Pro Glu Leu Leu Gly Gly Pro Ser Val Phe Leu Phe Pro
Pro Lys Pro Lys Asp Thr Leu Met Ile Ser Arg Thr Pro Glu Val Thr
Cys Val Val Val Asp Val Ser His Glu Asp Pro Glu Val Lys Phe Asn
Trp Tyr Val Asp Gly Val Glu Val His Asn Ala Lys Thr Lys Pro Arg
Glu Glu Gln Tyr Asn Ser Thr Tyr Arg Val Val Ser Val Leu Thr Val
Leu His Gln Asp Trp Leu Asn Gly Lys Glu Tyr Lys Cys Lys Val Ser
Asn Lys Ala Leu Pro Ala Pro Ile Glu Lys Thr Ile Ser Lys Ala Lys
Gly Gln Pro Arg Glu Pro Gln Val Tyr Thr Leu Pro Pro Ser Arg Glu
Glu Met Thr Lys Asn Gln Val Ser Leu Thr Cys Leu Val Lys Gly Phe
Tyr Pro Ser Asp Ile Ala Val Glu Trp Glu Ser Asn Gly Gln Pro Glu
Asn Asn Tyr Lys Thr Thr Pro Pro Val Leu Asp Ser Asp Gly Ser Phe
Phe Leu Tyr Ser Lys Leu Thr Val Asp Lys Ser Arg Trp Gln Gln Gly
Asn Val Phe Ser Cys Ser Val Met His Glu Ala Leu His Asn His Tyr
Thr Gln Lys Ser Leu Ser Leu Ser Pro Gly Lys Asp Ile Asp Asp Asp
Asp Asp Asp Asp Asp Asp Asp

SEQ ID NO: 7 (hTNALP-Fc-D10 without signal peptide)
Leu Val Pro Glu Lys Glu Lys Asp Pro Lys Tyr Trp Arg Asp Gln Ala
Gln Glu Thr Leu Lys Tyr Ala Leu Glu Leu Gln Lys Leu Asn Thr Asn
Val Ala Lys Asn Val Ile Met Phe Leu Gly Asp Gly Met Gly Val Ser
Thr Val Thr Ala Ala Arg Ile Leu Lys Gly Gln Leu His His Asn Pro
Gly Glu Glu Thr Arg Leu Glu Met Asp Lys Phe Pro Phe Val Ala Leu
Ser Lys Thr Tyr Asn Thr Asn Ala Gln Val Pro Asp Ser Ala Gly Thr
Ala Thr Ala Tyr Leu Cys Gly Val Lys Ala Asn Glu Gly Thr Val Gly
Val Ser Ala Ala Thr Glu Arg Ser Arg Cys Asn Thr Thr Gln Gly Asn
Glu Val Thr Ser Ile Leu Arg Trp Ala Lys Asp Ala Gly Lys Ser Val

FIG. 12 (CONT'D)

Gly Ile Val Thr Thr Thr Arg Val Asn His Ala Thr Pro Ser Ala Ala
Tyr Ala His Ser Ala Asp Arg Asp Trp Tyr Ser Asp Asn Glu Met Pro
Pro Glu Ala Leu Ser Gln Gly Cys Lys Asp Ile Ala Tyr Gln Leu Met
His Asn Ile Arg Asp Ile Asp Val Ile Met Gly Gly Gly Arg Lys Tyr
Met Tyr Pro Lys Asn Lys Thr Asp Val Glu Tyr Glu Ser Asp Glu Lys
Ala Arg Gly Thr Arg Leu Asp Gly Leu Asp Leu Val Asp Thr Trp Lys
Ser Phe Lys Pro Arg Tyr Lys His Ser His Phe Ile Trp Asn Arg Thr
Glu Leu Leu Thr Leu Asp Pro His Asn Val Asp Tyr Leu Leu Gly Leu
Phe Glu Pro Gly Asp Met Gln Tyr Glu Leu Asn Arg Asn Asn Val Thr
Asp Pro Ser Leu Ser Glu Met Val Val Val Ala Ile Gln Ile Leu Arg
Lys Asn Pro Lys Gly Phe Phe Leu Leu Val Glu Gly Gly Arg Ile Asp
His Gly His His Glu Gly Lys Ala Lys Gln Ala Leu His Glu Ala Val
Glu Met Asp Arg Ala Ile Gly Gln Ala Gly Ser Leu Thr Ser Ser Glu
Asp Thr Leu Thr Val Val Thr Ala Asp His Ser His Val Phe Thr Phe
Gly Gly Tyr Thr Pro Arg Gly Asn Ser Ile Phe Gly Leu Ala Pro Met
Leu Ser Asp Thr Asp Lys Lys Pro Phe Thr Ala Ile Leu Tyr Gly Asn
Gly Pro Gly Tyr Lys Val Val Gly Gly Glu Arg Glu Asn Val Ser Met
Val Asp Tyr Ala His Asn Asn Tyr Gln Ala Gln Ser Ala Val Pro Leu
Arg His Glu Thr His Gly Gly Glu Asp Val Ala Val Phe Ser Lys Gly
Pro Met Ala His Leu Leu His Gly Val His Glu Gln Asn Tyr Val Pro
His Val Met Ala Tyr Ala Ala Cys Ile Gly Ala Asn Leu Gly His Cys
Ala Pro Ala Ser Ser Leu Lys Asp Lys Thr His Thr Cys Pro Pro Cys
Pro Ala Pro Glu Leu Leu Gly Gly Pro Ser Val Phe Leu Phe Pro Pro
Lys Pro Lys Asp Thr Leu Met Ile Ser Arg Thr Pro Glu Val Thr Cys
Val Val Val Asp Val Ser His Glu Asp Pro Glu Val Lys Phe Asn Trp
Tyr Val Asp Gly Val Glu Val His Asn Ala Lys Thr Lys Pro Arg Glu
Glu Gln Tyr Asn Ser Thr Tyr Arg Val Val Ser Val Leu Thr Val Leu
His Gln Asp Trp Leu Asn Gly Lys Glu Tyr Lys Cys Lys Val Ser Asn
Lys Ala Leu Pro Ala Pro Ile Glu Lys Thr Ile Ser Lys Ala Lys Gly

FIG. 12 (CONT'D)

Gln Pro Arg Glu Pro Gln Val Tyr Thr Leu Pro Pro Ser Arg Glu Glu
Met Thr Lys Asn Gln Val Ser Leu Thr Cys Leu Val Lys Gly Phe Tyr
Pro Ser Asp Ile Ala Val Glu Trp Glu Ser Asn Gly Gln Pro Glu Asn
Asn Tyr Lys Thr Thr Pro Pro Val Leu Asp Ser Asp Gly Ser Phe Phe
Leu Tyr Ser Lys Leu Thr Val Asp Lys Ser Arg Trp Gln Gln Gly Asn
Val Phe Ser Cys Ser Val Met His Glu Ala Leu His Asn His Tyr Thr
Gln Lys Ser Leu Ser Leu Ser Pro Gly Lys Asp Ile Asp Asp Asp Asp
Asp Asp Asp Asp Asp Asp

SEQUENCE LISTING

<160> NUMBER OF SEQ ID NOS: 9

<210> SEQ ID NO 1
<211> LENGTH: 1500
<212> TYPE: DNA
<213> ORGANISM: Homo sapiens

<400> SEQUENCE: 1

```
ggatccacca tgatttcacc attcttagta ctggccattg gcacctgcct tactaactcc      60
ttagtgccag agaaagagaa agaccccaag tactggcgag accaagcgca agagacactg     120
aaatatgccc tggagcttca gaagctcaac accaacgtgg ctaagaatgt catcatgttc     180
ctgggagatg gatgggtgt ctccacagtg acggctgccc gcatcctcaa gggtcagctc     240
caccacaacc ctggggagga gaccaggctg gagatggaca gttcccctt cgtgccctc      300
tccaagacgt acaacaccaa tgcccaggtc cctgacagcg ccggcaccgc caccgcctac     360
ctgtgtgggg tgaaggccaa tgagggcacc gtggggtaa gcgcagccac tgagcgttcc      420
cggtgcaaca ccacccaggg gaacgaggtc acctccatcc tgcgctgggc caaggacgct     480
gggaaatctg tgggcattgt gaccaccacg agagtgaacc atgccacccc cagcgccgcc     540
tacgcccact cggctgaccg ggactggtac tcagacaacg agatgccccc tgaggccttg     600
agccagggct gtaaggacat cgcctaccag ctcatgcata acatcaggga cattgacgtg     660
atcatggggg gtggccggaa atacatgtac cccaagaata aaactgatgt ggagtatgag     720
agtgacgaga agccagggg cacgaggctg gacggcctgg acctcgttga cacctggaag     780
agcttcaaac cgagatacaa gcactccac ttcatctgga accgcacgga actcctgacc     840
cttgaccccc acaatgtgga ctacctattg ggtctcttcg agccagggga catgcagtac     900
gagctgaaca ggaacaacgt gacggacccg tcactctccg agatggtggt ggtggccatc     960
cagatcctgc ggaagaaccc caaaggcttc ttcttgctgg tggaaggagg cagaattgac    1020
cacgggcacc atgaaggaaa agccaagcag gccctgcatg aggcggtgga gatggaccgg    1080
gccatcgggc aggcaggcag cttgacctcc tcggaagaca ctctgaccgt ggtcactgcg    1140
gaccattccc acgtcttcac atttggtgga tacaccccccc gtggcaactc tatctttggt    1200
ctggccccca tgctgagtga cacagacaag aagcccttca ctgccatcct gtatggcaat    1260
gggcctggct acaaggtggt gggcggtgaa cgagagaatg tctccatggt ggactatgct    1320
cacaacaact accaggcgca gtctgctgtg ccctgcgcc acgagaccca cggcggggag    1380
gacgtggccg tcttctccaa gggccccatg gcgcacctgc tgcacggcgt ccacgagcag    1440
aactacgtcc cccacgtgat ggcgtatgca gcctgcatcg gggccaacct cggccactgt    1500
```

<210> SEQ ID NO 2
<211> LENGTH: 502
<212> TYPE: PRT
<213> ORGANISM: Homo sapiens

<400> SEQUENCE: 2

```
Met Ile Ser Pro Phe Leu Val Leu Ala Ile Gly Thr Cys Leu Thr Asn
1               5                   10                  15

Ser Leu Val Pro Glu Lys Glu Lys Asp Pro Lys Tyr Trp Arg Asp Gln
                20                  25                  30

Ala Gln Glu Thr Leu Lys Tyr Ala Leu Glu Leu Gln Lys Leu Asn Thr
            35                  40                  45

Asn Val Ala Lys Asn Val Ile Met Phe Leu Gly Asp Gly Met Gly Val
        50                  55                  60

Ser Thr Val Thr Ala Ala Arg Ile Leu Lys Gly Gln Leu His His Asn
65                  70                  75                  80

Pro Gly Glu Glu Thr Arg Leu Glu Met Asp Lys Phe Pro Phe Val Ala
                85                  90                  95

Leu Ser Lys Thr Tyr Asn Thr Asn Ala Gln Val Pro Asp Ser Ala Gly
```

Thr Ala Thr Ala Tyr Leu Cys Gly Val Lys Ala Asn Glu Gly Thr Val
            100                 105                 110
        115                 120                 125

Gly Val Ser Ala Ala Thr Glu Arg Ser Arg Cys Asn Thr Thr Gln Gly
        130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
                165                 170                 175

Ala Tyr Ala His Ser Ala Asp Arg Asp Trp Tyr Ser Asp Asn Glu Met
                180                 185                 190

Pro Pro Glu Ala Leu Ser Gln Gly Cys Lys Asp Ile Ala Tyr Gln Leu
            195                 200                 205

Met His Asn Ile Arg Asp Ile Asp Val Ile Met Gly Gly Gly Arg Lys
        210                 215                 220

Tyr Met Tyr Pro Lys Asn Lys Thr Asp Val Glu Tyr Glu Ser Asp Glu
225                 230                 235                 240

Lys Ala Arg Gly Thr Arg Leu Asp Gly Leu Asp Leu Val Asp Thr Trp
                245                 250                 255

Lys Ser Phe Lys Pro Arg Tyr Lys His Ser His Phe Ile Trp Asn Arg
                260                 265                 270

Thr Glu Leu Leu Thr Leu Asp Pro His Asn Val Asp Tyr Leu Leu Gly
            275                 280                 285

Leu Phe Glu Pro Gly Asp Met Gln Tyr Glu Leu Asn Arg Asn Asn Val
        290                 295                 300

Thr Asp Pro Ser Leu Ser Glu Met Val Val Ala Ile Gln Ile Leu
305                 310                 315                 320

Arg Lys Asn Pro Lys Gly Phe Phe Leu Leu Val Glu Gly Gly Arg Ile
                325                 330                 335

Asp His Gly His His Glu Gly Lys Ala Lys Gln Ala Leu His Glu Ala
                340                 345                 350

Val Glu Met Asp Arg Ala Ile Gly Gln Ala Gly Ser Leu Thr Ser Ser
            355                 360                 365

Glu Asp Thr Leu Thr Val Val Thr Ala Asp His Ser His Val Phe Thr
        370                 375                 380

Phe Gly Gly Tyr Thr Pro Arg Gly Asn Ser Ile Phe Gly Leu Ala Pro
385                 390                 395                 400

Met Leu Ser Asp Thr Asp Lys Lys Pro Phe Thr Ala Ile Leu Tyr Gly
                405                 410                 415

Asn Gly Pro Gly Tyr Lys Val Val Gly Gly Glu Arg Glu Asn Val Ser
                420                 425                 430

Met Val Asp Tyr Ala His Asn Asn Tyr Gln Ala Gln Ser Ala Val Pro
            435                 440                 445

Leu Arg His Glu Thr His Gly Gly Glu Asp Val Ala Val Phe Ser Lys
        450                 455                 460

Gly Pro Met Ala His Leu Leu His Gly Val His Glu Gln Asn Tyr Val
465                 470                 475                 480

Pro His Val Met Ala Tyr Ala Ala Cys Ile Gly Ala Asn Leu Gly His
                485                 490                 495

Cys Ala Pro Ala Ser Ser
            500

<210> SEQ ID NO 3

<211> LENGTH: 1500
<212> TYPE: DNA
<213> ORGANISM: Homo sapiens

<400> SEQUENCE: 3

```
ggatccacca tgatttcacc attcttagta ctggccattg gcacctgcct tactaactcc      60
ttagtgccag agaaagagaa agaccccaag tactggcgag accaagcgca agagacactg     120
aaatatgccc tggagcttca gaagctcaac accaacgtgg ctaagaatgt catcatgttc     180
ctgggagatg ggatgggtgt ctccacagtg acggctgccc gcatcctcaa gggtcagctc     240
caccacaacc ctggggagga gaccaggctg gagatggaca gttccccctt cgtggccctc     300
tccaagacgt acaacaccaa tgcccaggtc cctgacagcg ccggcaccgc caccgcctac     360
ctgtgtgggg tgaaggccaa tgagggcacc gtggggggtaa gcgcagccac tgagcgttcc     420
cggtgcaaca ccacccaggg gaacgaggtc acctccatcc tgcgctgggc caaggacgct     480
gggaaatctg tgggcattgt gaccaccacg agagtgaacc atgccacccc cagcgccgcc     540
tacgcccact cggctgaccg ggactggtac tcagacaacg agatgccccc tgaggccttg     600
agccagggct gtaaggacat cgcctaccag ctcatgcata acatcaggga cattgacgtg     660
atcatggggg gtgccggaa atacatgtac cccaagaata aaactgatgt ggagtatgag     720
agtgacgaga agccaggggg cacgaggctg gacggcctgg acctcgttga cacctggaag     780
agcttcaaac cgagatacaa gcactccac ttcatctgga accgcactgga actcctgacc     840
cttgaccccc acaatgtgga ctacctattg ggtctcttcg agccagggga catgcagtac     900
gagctgaaca ggaacaacgt gacggacccg tcactctccg agatggtggt ggtggccatc     960
cagatcctgc ggaagaaccc caaaggcttc ttcttgctgg tggaaggagg cagaattgac    1020
cacgggcacc atgaaggaaa agccaagcag gccctgcatg aggcggtgga gatggaccgg    1080
gccatcgggc aggcaggcag cttgacctcc tcggaagaca ctctgaccgt ggtcactgcg    1140
gaccattccc acgtcttcac atttggtgga tacaccccccc gtggcaactc tatctttggt    1200
ctggccccca tgctgagtga cacagacaag aagcccttca ctgccatcct gtatggcaat    1260
gggcctggct acaaggtggt gggcggtgaa cgagagaatg tctccatggt ggactatgct    1320
cacaacaact accaggcgca gtctgctgtg ccctgcgcc acgagaccca cggcggggag    1380
gacgtggccg tcttctccaa gggccccatg gcgcacctgc tgcacggcgt ccacgagcag    1440
aactacgtcc cccacgtgat ggcgtatgca gcctgcatcg gggccaacct cggccactgt    1500
```

<210> SEQ ID NO 4
<211> LENGTH: 512
<212> TYPE: PRT
<213> ORGANISM: Homo sapiens

<400> SEQUENCE: 4

```
Met Ile Ser Pro Phe Leu Val Leu Ala Ile Gly Thr Cys Leu Thr Asn
1               5                   10                  15

Ser Leu Val Pro Glu Lys Glu Lys Asp Pro Lys Tyr Trp Arg Asp Gln
            20                  25                  30

Ala Gln Glu Thr Leu Lys Tyr Ala Leu Glu Leu Gln Lys Leu Asn Thr
        35                  40                  45

Asn Val Ala Lys Asn Val Ile Met Phe Leu Gly Asp Gly Met Gly Val
    50                  55                  60

Ser Thr Val Thr Ala Ala Arg Ile Leu Lys Gly Gln Leu His His Asn
65                  70                  75                  80
```

```
Pro Gly Glu Glu Thr Arg Leu Glu Met Asp Lys Phe Pro Phe Val Ala
                85                  90                  95

Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
        115                 120                 125

Gly Val Ser Ala Ala Thr Glu Arg Ser Arg Cys Asn Thr Thr Gln Gly
    130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
                165                 170                 175

Ala Tyr Ala His Ser Ala Asp Arg Asp Trp Tyr Ser Asp Asn Glu Met
            180                 185                 190

Pro Pro Glu Ala Leu Ser Gln Gly Cys Lys Asp Ile Ala Tyr Gln Leu
        195                 200                 205

Met His Asn Ile Arg Asp Ile Asp Val Ile Met Gly Gly Gly Arg Lys
    210                 215                 220

Tyr Met Tyr Pro Lys Asn Lys Thr Asp Val Glu Tyr Glu Ser Asp Glu
225                 230                 235                 240

Lys Ala Arg Gly Thr Arg Leu Asp Gly Leu Asp Leu Val Asp Thr Trp
                245                 250                 255

Lys Ser Phe Lys Pro Arg Tyr Lys His Ser His Phe Ile Trp Asn Arg
            260                 265                 270

Thr Glu Leu Leu Thr Leu Asp Pro His Asn Val Asp Tyr Leu Leu Gly
        275                 280                 285

Leu Phe Glu Pro Gly Asp Met Gln Tyr Glu Leu Asn Arg Asn Asn Val
    290                 295                 300

Thr Asp Pro Ser Leu Ser Glu Met Val Val Ala Ile Gln Ile Leu
305                 310                 315                 320

Arg Lys Asn Pro Lys Gly Phe Phe Leu Leu Val Glu Gly Gly Arg Ile
                325                 330                 335

Asp His Gly His His Glu Gly Lys Ala Lys Gln Ala Leu His Glu Ala
            340                 345                 350

Val Glu Met Asp Arg Ala Ile Gly Gln Ala Gly Ser Leu Thr Ser Ser
        355                 360                 365

Glu Asp Thr Leu Thr Val Val Thr Ala Asp His Ser His Val Phe Thr
    370                 375                 380

Phe Gly Gly Tyr Thr Pro Arg Gly Asn Ser Ile Phe Gly Leu Ala Pro
385                 390                 395                 400

Met Leu Ser Asp Thr Asp Lys Lys Pro Phe Thr Ala Ile Leu Tyr Gly
                405                 410                 415

Asn Gly Pro Gly Tyr Lys Val Val Gly Gly Glu Arg Glu Asn Val Ser
            420                 425                 430

Met Val Asp Tyr Ala His Asn Asn Tyr Gln Ala Gln Ser Ala Val Pro
        435                 440                 445

Leu Arg His Glu Thr His Gly Gly Glu Asp Val Ala Val Phe Ser Lys
    450                 455                 460

Gly Pro Met Ala His Leu Leu His Gly Val His Glu Gln Asn Tyr Val
465                 470                 475                 480

Pro His Val Met Ala Tyr Ala Ala Cys Ile Gly Ala Asn Leu Gly His
                485                 490                 495

Cys Ala Pro Ala Ser Ser Asp Asp Asp Asp Asp Asp Asp Asp Asp Asp
```

-continued

```
                500                 505                 510
```

<210> SEQ ID NO 5
<211> LENGTH: 227
<212> TYPE: PRT
<213> ORGANISM: Homo sapiens

<400> SEQUENCE: 5

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225
```

<210> SEQ ID NO 6
<211> LENGTH: 743
<212> TYPE: PRT
<213> ORGANISM: Homo sapiens

<400> SEQUENCE: 6

```
Met Ile Ser Pro Phe Leu Val Leu Ala Ile Gly Thr Cys Leu Thr Asn
1               5                   10                  15

Ser Leu Val Pro Glu Lys Glu Lys Asp Pro Lys Tyr Trp Arg Asp Gln
            20                  25                  30

Ala Gln Glu Thr Leu Lys Tyr Ala Leu Glu Leu Gln Lys Leu Asn Thr
        35                  40                  45

Asn Val Ala Lys Asn Val Ile Met Phe Leu Gly Asp Gly Met Gly Val
    50                  55                  60

Ser Thr Val Thr Ala Ala Arg Ile Leu Lys Gly Gln Leu His His Asn
65                  70                  75                  80

Pro Gly Glu Glu Thr Arg Leu Glu Met Asp Lys Phe Pro Phe Val Ala
```

```
                        85                  90                  95
Leu Ser Lys Thr Tyr Asn Thr Asn Ala Gln Val Pro Asp Ser Ala Gly
                100                 105                 110
Thr Ala Thr Ala Tyr Leu Cys Gly Val Lys Ala Asn Glu Gly Thr Val
                115                 120                 125
Gly Val Ser Ala Ala Thr Glu Arg Ser Arg Cys Asn Thr Thr Gln Gly
130                 135                 140
Asn Glu Val Thr Ser Ile Leu Arg Trp Ala Lys Asp Ala Gly Lys Ser
145                 150                 155                 160
Val Gly Ile Val Thr Thr Thr Arg Val Asn His Ala Thr Pro Ser Ala
                165                 170                 175
Ala Tyr Ala His Ser Ala Asp Arg Asp Trp Tyr Ser Asp Asn Glu Met
                180                 185                 190
Pro Pro Glu Ala Leu Ser Gln Gly Cys Lys Asp Ile Ala Tyr Gln Leu
                195                 200                 205
Met His Asn Ile Arg Asp Ile Asp Val Ile Met Gly Gly Gly Arg Lys
                210                 215                 220
Tyr Met Tyr Pro Lys Asn Lys Thr Asp Val Glu Tyr Glu Ser Asp Glu
225                 230                 235                 240
Lys Ala Arg Gly Thr Arg Leu Asp Gly Leu Asp Leu Val Asp Thr Trp
                245                 250                 255
Lys Ser Phe Lys Pro Arg Tyr Lys His Ser His Phe Ile Trp Asn Arg
                260                 265                 270
Thr Glu Leu Leu Thr Leu Asp Pro His Asn Val Asp Tyr Leu Leu Gly
                275                 280                 285
Leu Phe Glu Pro Gly Asp Met Gln Tyr Glu Leu Asn Arg Asn Asn Val
                290                 295                 300
Thr Asp Pro Ser Leu Ser Glu Met Val Val Ala Ile Gln Ile Leu
305                 310                 315                 320
Arg Lys Asn Pro Lys Gly Phe Phe Leu Leu Val Glu Gly Gly Arg Ile
                325                 330                 335
Asp His Gly His His Glu Gly Lys Ala Lys Gln Ala Leu His Glu Ala
                340                 345                 350
Val Glu Met Asp Arg Ala Ile Gly Gln Ala Gly Ser Leu Thr Ser Ser
                355                 360                 365
Glu Asp Thr Leu Thr Val Val Thr Ala Asp His Ser His Val Phe Thr
                370                 375                 380
Phe Gly Gly Tyr Thr Pro Arg Gly Asn Ser Ile Phe Gly Leu Ala Pro
385                 390                 395                 400
Met Leu Ser Asp Thr Asp Lys Lys Pro Phe Thr Ala Ile Leu Tyr Gly
                405                 410                 415
Asn Gly Pro Gly Tyr Lys Val Val Gly Gly Glu Arg Glu Asn Val Ser
                420                 425                 430
Met Val Asp Tyr Ala His Asn Asn Tyr Gln Ala Gln Ser Ala Val Pro
                435                 440                 445
Leu Arg His Glu Thr His Gly Gly Glu Asp Val Ala Val Phe Ser Lys
                450                 455                 460
Gly Pro Met Ala His Leu Leu His Gly Val His Glu Gln Asn Tyr Val
465                 470                 475                 480
Pro His Val Met Ala Tyr Ala Ala Cys Ile Gly Ala Asn Leu Gly His
                485                 490                 495
Cys Ala Pro Ala Ser Ser Leu Lys Asp Lys Thr His Thr Cys Pro Pro
                500                 505                 510
```

```
Cys Pro Ala Pro Glu Leu Leu Gly Gly Pro Ser Val Phe Leu Phe Pro
            515                 520                 525
Pro Lys Pro Lys Asp Thr Leu Met Ile Ser Arg Thr Pro Glu Val Thr
        530                 535                 540
Cys Val Val Val Asp Val Ser His Glu Asp Pro Glu Val Lys Phe Asn
545                 550                 555                 560
Trp Tyr Val Asp Gly Val Glu Val His Asn Ala Lys Thr Lys Pro Arg
                565                 570                 575
Glu Glu Gln Tyr Asn Ser Thr Tyr Arg Val Val Ser Val Leu Thr Val
            580                 585                 590
Leu His Gln Asp Trp Leu Asn Gly Lys Glu Tyr Lys Cys Lys Val Ser
        595                 600                 605
Asn Lys Ala Leu Pro Ala Pro Ile Glu Lys Thr Ile Ser Lys Ala Lys
    610                 615                 620
Gly Gln Pro Arg Glu Pro Gln Val Tyr Thr Leu Pro Pro Ser Arg Glu
625                 630                 635                 640
Glu Met Thr Lys Asn Gln Val Ser Leu Thr Cys Leu Val Lys Gly Phe
                645                 650                 655
Tyr Pro Ser Asp Ile Ala Val Glu Trp Glu Ser Asn Gly Gln Pro Glu
            660                 665                 670
Asn Asn Tyr Lys Thr Thr Pro Pro Val Leu Asp Ser Asp Gly Ser Phe
        675                 680                 685
Phe Leu Tyr Ser Lys Leu Thr Val Asp Lys Ser Arg Trp Gln Gln Gly
    690                 695                 700
Asn Val Phe Ser Cys Ser Val Met His Glu Ala Leu His Asn His Tyr
705                 710                 715                 720
Thr Gln Lys Ser Leu Ser Leu Ser Pro Gly Lys Asp Ile Asp Asp Asp
                725                 730                 735
Asp Asp Asp Asp Asp Asp Asp
            740

<210> SEQ ID NO 7
<211> LENGTH: 726
<212> TYPE: PRT
<213> ORGANISM: Homo sapiens

<400> SEQUENCE: 7

Leu Val Pro Glu Lys Glu Lys Asp Pro Lys Tyr Trp Arg Asp Gln Ala
1               5                   10                  15
Gln Glu Thr Leu Lys Tyr Ala Leu Glu Leu Gln Lys Leu Asn Thr Asn
            20                  25                  30
Val Ala Lys Asn Val Ile Met Phe Leu Gly Asp Gly Met Gly Val Ser
        35                  40                  45
Thr Val Thr Ala Ala Arg Ile Leu Lys Gly Gln Leu His His Asn Pro
    50                  55                  60
Gly Glu Glu Thr Arg Leu Glu Met Asp Lys Phe Pro Phe Val Ala Leu
65                  70                  75                  80
Ser Lys Thr Tyr Asn Thr Asn Ala Gln Val Pro Asp Ser Ala Gly Thr
                85                  90                  95
Ala Thr Ala Tyr Leu Cys Gly Val Lys Ala Asn Glu Gly Thr Val Gly
            100                 105                 110
Val Ser Ala Ala Thr Glu Arg Ser Arg Cys Asn Thr Thr Gln Gly Asn
        115                 120                 125
Glu Val Thr Ser Ile Leu Arg Trp Ala Lys Asp Ala Gly Lys Ser Val
```

-continued

```
              130                 135                 140
Gly Ile Val Thr Thr Thr Arg Val Asn His Ala Thr Pro Ser Ala Ala
145                 150                 155                 160

Tyr Ala His Ser Ala Asp Arg Asp Trp Tyr Ser Asp Asn Glu Met Pro
                165                 170                 175

Pro Glu Ala Leu Ser Gln Gly Cys Lys Asp Ile Ala Tyr Gln Leu Met
                180                 185                 190

His Asn Ile Arg Asp Ile Asp Val Ile Met Gly Gly Arg Lys Tyr
                195                 200                 205

Met Tyr Pro Lys Asn Lys Thr Asp Val Glu Tyr Glu Ser Asp Glu Lys
        210                 215                 220

Ala Arg Gly Thr Arg Leu Asp Gly Leu Asp Leu Val Asp Thr Trp Lys
225                 230                 235                 240

Ser Phe Lys Pro Arg Tyr Lys His Ser His Phe Ile Trp Asn Arg Thr
                245                 250                 255

Glu Leu Leu Thr Leu Asp Pro His Asn Val Asp Tyr Leu Leu Gly Leu
                260                 265                 270

Phe Glu Pro Gly Asp Met Gln Tyr Glu Leu Asn Arg Asn Asn Val Thr
                275                 280                 285

Asp Pro Ser Leu Ser Glu Met Val Val Ala Ile Gln Ile Leu Arg
        290                 295                 300

Lys Asn Pro Lys Gly Phe Phe Leu Leu Val Glu Gly Gly Arg Ile Asp
305                 310                 315                 320

His Gly His His Glu Gly Lys Ala Lys Gln Ala Leu His Glu Ala Val
                325                 330                 335

Glu Met Asp Arg Ala Ile Gly Gln Ala Gly Ser Leu Thr Ser Ser Glu
        340                 345                 350

Asp Thr Leu Thr Val Val Thr Ala Asp His Ser His Val Phe Thr Phe
        355                 360                 365

Gly Gly Tyr Thr Pro Arg Gly Asn Ser Ile Phe Gly Leu Ala Pro Met
        370                 375                 380

Leu Ser Asp Thr Asp Lys Lys Pro Phe Thr Ala Ile Leu Tyr Gly Asn
385                 390                 395                 400

Gly Pro Gly Tyr Lys Val Val Gly Gly Glu Arg Glu Asn Val Ser Met
                405                 410                 415

Val Asp Tyr Ala His Asn Asn Tyr Gln Ala Gln Ser Ala Val Pro Leu
        420                 425                 430

Arg His Glu Thr His Gly Gly Glu Asp Val Ala Val Phe Ser Lys Gly
                435                 440                 445

Pro Met Ala His Leu Leu His Gly Val His Glu Gln Asn Tyr Val Pro
        450                 455                 460

His Val Met Ala Tyr Ala Ala Cys Ile Gly Ala Asn Leu Gly His Cys
465                 470                 475                 480

Ala Pro Ala Ser Ser Leu Lys Asp Lys Thr His Thr Cys Pro Pro Cys
                485                 490                 495

Pro Ala Pro Glu Leu Leu Gly Gly Pro Ser Val Phe Leu Phe Pro Pro
                500                 505                 510

Lys Pro Lys Asp Thr Leu Met Ile Ser Arg Thr Pro Glu Val Thr Cys
                515                 520                 525

Val Val Val Asp Val Ser His Glu Asp Pro Glu Val Lys Phe Asn Trp
        530                 535                 540

Tyr Val Asp Gly Val Glu Val His Asn Ala Lys Thr Lys Pro Arg Glu
545                 550                 555                 560
```

```
Glu Gln Tyr Asn Ser Thr Tyr Arg Val Val Ser Val Leu Thr Val Leu
                565             570             575

His Gln Asp Trp Leu Asn Gly Lys Glu Tyr Lys Cys Lys Val Ser Asn
            580             585             590

Lys Ala Leu Pro Ala Pro Ile Glu Lys Thr Ile Ser Lys Ala Lys Gly
        595             600             605

Gln Pro Arg Glu Pro Gln Val Tyr Thr Leu Pro Pro Ser Arg Glu Glu
    610             615             620

Met Thr Lys Asn Gln Val Ser Leu Thr Cys Leu Val Lys Gly Phe Tyr
625             630             635             640

Pro Ser Asp Ile Ala Val Glu Trp Glu Ser Asn Gly Gln Pro Glu Asn
            645             650             655

Asn Tyr Lys Thr Thr Pro Pro Val Leu Asp Ser Asp Gly Ser Phe Phe
            660             665             670

Leu Tyr Ser Lys Leu Thr Val Asp Lys Ser Arg Trp Gln Gln Gly Asn
        675             680             685

Val Phe Ser Cys Ser Val Met His Glu Ala Leu His Asn His Tyr Thr
    690             695             700

Gln Lys Ser Leu Ser Leu Ser Pro Gly Lys Asp Ile Asp Asp Asp Asp
705             710             715             720

Asp Asp Asp Asp Asp Asp
                725

<210> SEQ ID NO 8
<211> LENGTH: 22
<212> TYPE: DNA
<213> ORGANISM: Artificial sequence
<220> FEATURE:
<223> OTHER INFORMATION: Synthetic

<400> SEQUENCE: 8
gagtaccatg ctgactgcat gc                                          22

<210> SEQ ID NO 9
<211> LENGTH: 25
<212> TYPE: DNA
<213> ORGANISM: Artificial sequence
<220> FEATURE:
<223> OTHER INFORMATION: Synthetic

<400> SEQUENCE: 9
ggagaggcat ctctgtttca agacc                                       25
```

COMPOSITIONS AND METHODS FOR TREATING CRANIOSYNOSTOSIS

This application claims priority to U.S. provisional patent application 62/023,620 filed Jul. 11, 2014, and U.S. provisional patent application 62/158,964, filed May 8, 2015, each of which are incorporated herein by reference in their entireties.

FIELD OF THE INVENTION

Provided herein are compositions and methods for treating craniosynostosis. In particular, provided herein are methods of treating and preventing craniosynostosis.

BACKGROUND OF THE INVENTION

Craniosynostosis is a debilitating condition in which adjacent calvarial (skull cap) bones fuse. Craniosynostosis can lead to high intracranial pressure, abnormal skull and facial shapes, airway impairments, obstructive sleep apnea, brain abnormalities, blindness, deafness, seizures and death (Rasmussen et al., Am J Med Genet A 2008; 146A(2):149-58; Renier et al., Childs Nerv Syst 2000; 16(10-11):645-58; Seruya et al., J Neurosurg Pediatr 2011; 8(1):40-8; Morriss-Kay et al., J Anat 2005; 207(5):637-53; Kreiborg et al., Scand J Plast Reconstr Surg 1981; 15(3):187-97; Addo et al., J Neurosurg Pediatr 2013; 11(3):296-301; Driessen et al., Arch Dis Child 2013; 98(7):538-43; Cohen and Kreiborg, Am J Med Gene 1992; 44(1):90-3; Okajima et al., Am J Med Genet 1999; 85(2):160-70; Shah et al., Am J Med Genet A 2006; 140(24):2794-6). The prevalence of craniosynostosis is high, at approximately 1 in 2500 live births.

Because the biochemical etiology of craniosynostosis is unknown, the only current treatment option for craniosynostosis is surgery combined with genetic counseling, dental, medical and social support (Rasmussen et al., supra). Notably, even with an early and accurate diagnosis, craniosynostosis has a high morbidity. For example, some patients require multiple surgeries throughout infancy and childhood to relieve high intracranial pressure, treat recurring craniosynostosis, and normalize skull and facial shapes (Cunningham et al., Orthod Craniofac Res. 2007; 10(2):67-81; Flapper et al., J Craniofac Surg 2009; 20(4):1252-5; Baird et al., Childs Nerv Syst 2011; 28(3):411-8).

Additional methods of treating and preventing craniosynostosis are needed.

SUMMARY OF THE INVENTION

Provided herein are compositions and methods for treating craniosynostosis. In particular, provided herein are methods of treating and preventing craniosynostosis.

Provided herein is a method of treating or preventing craniosynostosis, comprising: increasing the activity and/or the expression levels of alkaline phosphatase in a subject. In some embodiment, the expression levels of alkaline phosphatase are increased by providing an exogenous source of alkaline phosphatase. In some embodiments, the expression levels of alkaline phosphatase are increased by providing an mRNA encoding alkaline phosphatase (See e.g., PCT Publication Nos: WO2013151664, WO2010135322, WO2009083738 and WO199219752, the content of which are incorporated herein to their entirety). In still another embodiment, the expression levels of alkaline phosphatase are increased by providing an isolated or recombinant alkaline phosphatase. In another embodiment, the expression levels of alkaline phosphatase are increased by providing a nucleic acid capable of expressing alkaline phosphatase in said subject.

The alkaline phosphatase in this disclosure includes any full-length alkaline phosphatase or any functional fragment thereof. Exemplary alkaline phosphatases include, for example, at least tissue non-specific alkaline phosphatase (referred to herein as TNAP or TNALP), placental alkaline phosphatase (PALP), germ cell alkaline phosphatase (GCALP), and intestinal alkaline phosphatase (IALP). They may be used alone or in combination in the present invention. In some embodiments, the alkaline phosphatase comprises a soluble alkaline phosphatase (sALP). In some embodiments, the alkaline phosphatase comprises a targeting moiety to specific tissues. Such targeting moiety may target the alkaline phosphatase to any tissue or organ, such as bone, liver, kidney, lung, etc. In one embodiment, the alkaline phosphatase comprises a bone-targeting moiety.

In some embodiments, the alkaline phosphatase comprises a polypeptide having the structure selected from, for example, Z-sALP-Y-$W_n$-X and X-$W_n$-Y-sALP-Z, wherein V is absent or is an amino acid sequence of at least one amino acid; X is absent or is an amino acid sequence of at least one amino acid; Y is absent or is an amino acid sequence of at least one amino acid; Z is absent or is an amino acid sequence of at least one amino acid; and $W_n$ is a polyaspartate or a polyglutamate. In one embodiment, the alkaline phosphatase disclosed herein comprises a polypeptide having the structure: sALP-D10. In one embodiment, such sALP-D10 construct comprises an amino acid sequence as set forth in SEQ ID NO: 4. In another embodiment, such sALP-D10 construct comprises an amino acid sequence encoded by a nucleic acid sequence as set forth in SEQ ID NO: 3.

In some embodiments, the alkaline phosphatase disclosed herein comprises a polypeptide having the structure selected from the group consisting of: Z-sALP-Y-spacer-X-$W_n$-V and Z-$W_n$-X-sALP-Y-spacer-V, wherein V is absent or is an amino acid sequence of at least one amino acid; X is absent or is an amino acid sequence of at least one amino acid; Y is absent or is an amino acid sequence of at least one amino acid; Z is absent or is an amino acid sequence of at least one amino acid; and $W_n$ is a polyaspartate or a polyglutamate.

In some embodiments, the alkaline phosphatase disclosed herein comprises a polypeptide having the structure: Z-sALP-Y-spacer-X-$W_n$-V.

In some embodiments, n=6. In other embodiments, n=1-20 (e.g., 10-16). In some embodiments, the spacer disclosed herein comprises a fragment crystallizable region (Fc). Such Fc may comprise, for example, a $CH_2$ domain, a $CH_3$ domain and a hinge region. Such Fc may be, for example, a constant domain of an immunoglobulin selected from the group consisting of IgG-1, IgG-2, IgG-3 and IgG-4. In one preferred embodiment, such Fc is a constant domain of an immunoglobulin IgG-1. Such Fc may have normal, reduced, or none of effector functions. An exemplary Fc amino acid sequence is set forth in SEQ ID NO: 5.

In some embodiments, the sALP disclosed herein comprises the tissue non-specific alkaline phosphatase (TNALP) or any functional fragment thereof. In one embodiment, the TNALP has the alanine of the hydrophobic C-terminus replaced by a stop codon. In one preferred embodiment, the TNALP comprises an amino acid sequence as set forth in SEQ ID NO: 2. In another preferred embodiment, TNALP comprises an amino acid sequence encoded by a nucleic acid sequence as set forth in SEQ ID NO: 1. In some embodiments, the TNALP is asfotase alfa.

In some embodiments, provided herein are methods of treating or preventing craniosynostosis, comprising: increasing the level of alkaline phosphatase (e.g., TNAP) in a subject by providing an exogenous source of alkaline phosphatase (e.g., a nucleic acid that expresses an exogenous alkaline phosphatase polypeptide or an isolated alkaline phosphatase polypeptide) to a subject at risk of or diagnosed with craniosynostosis, wherein the alkaline phosphatase polypeptide treats or prevents craniosynostosis. In some embodiments, the subject is a neonatal subject. In some embodiments, treatment is initiated within 1 hour, 8 hours, 12 hours, 1 day, 2 days, 3 days, 4 days, 5 days, 6 days, 1 week, 2, weeks, 3 weeks, or one month of birth. In some embodiments, treatment is initiated prior to birth (e.g. in utero). In some embodiments, treatment is initiated at the embryo stage (e.g., during an in vitro fertilization procedure). In some embodiments, treatment is provided to a female during gestation of a subject having or suspected of having craniosynostosis. In some embodiments, the subject has hypophosphatasia (HPP) and treatment prevents craniosynostosis associated with HPP. In some embodiments, the subject is diagnosed with craniosynostosis prior to initiating treatment.

In some embodiments, treatment is repeated at least once. Once treatment is initiated, it may be continued at least once daily, weekly, monthly, or yearly (e.g., one or more times per day, week, month, or year). In some embodiments, the nucleic acid is in a cell, vector, or gene delivery vehicle. In some embodiments, the cell is from the subject and has been genetically modified to express the TNAP. In some embodiments, the vector is a viral vector (e.g., a retroviral vector, such as a lentiviral vector or adeno-associated viral vector, an adenoviral vector, or an alphaviral vector). In some embodiments, the nucleic acids molecule is naked DNA. In some embodiments, the subject is a human or non-human subject. In some embodiments, the subject has a mutation in a fibroblast growth factor receptor an (FGFR) gene (e.g., FGFR1, FGFR2, or FGFR3) gene. In some embodiments, the subject is tested for the mutation prior to or after providing the exogenous TNAP nucleic acid. In other embodiments, the subject is treated with an exogenous source of TNAP after the subject is identified as having a mutation in an FGFR gene. In yet other embodiments, treatment results in reversal of craniosynostosis or a reduction in the extent or severity of one or more symptoms of craniosynostosis (e.g., intracranial pressure, abnormal cranial bone mineralization, abnormal physical examination, or abnormal radiographic results).

Additional embodiments provide a method of treating or preventing craniosynostosis in a subject with HPP, comprising: increasing the activity and/or the expression levels of alkaline phosphatase in a subject diagnosed with or at risk of developing HPP.

Further embodiments provide use of an exogenous source of alkaline phosphatase (e.g., a nucleic acid molecule that encodes an exogenous alkaline phosphatase polypeptide or an isolated alkaline phosphatase polypeptide) in the treatment or prevention of craniosynostosis.

Additional embodiments provide a pharmaceutical composition comprising a nucleic acid molecule that encodes an exogenous alkaline phosphatase polypeptide (e.g., a vector). Additional embodiments are described herein.

DESCRIPTION OF THE DRAWINGS

FIG. 12 shows exemplary TNALP nucleic acid and amino acid sequences (SEQ ID NOs: 1-7).

DEFINITIONS

Figure 1:
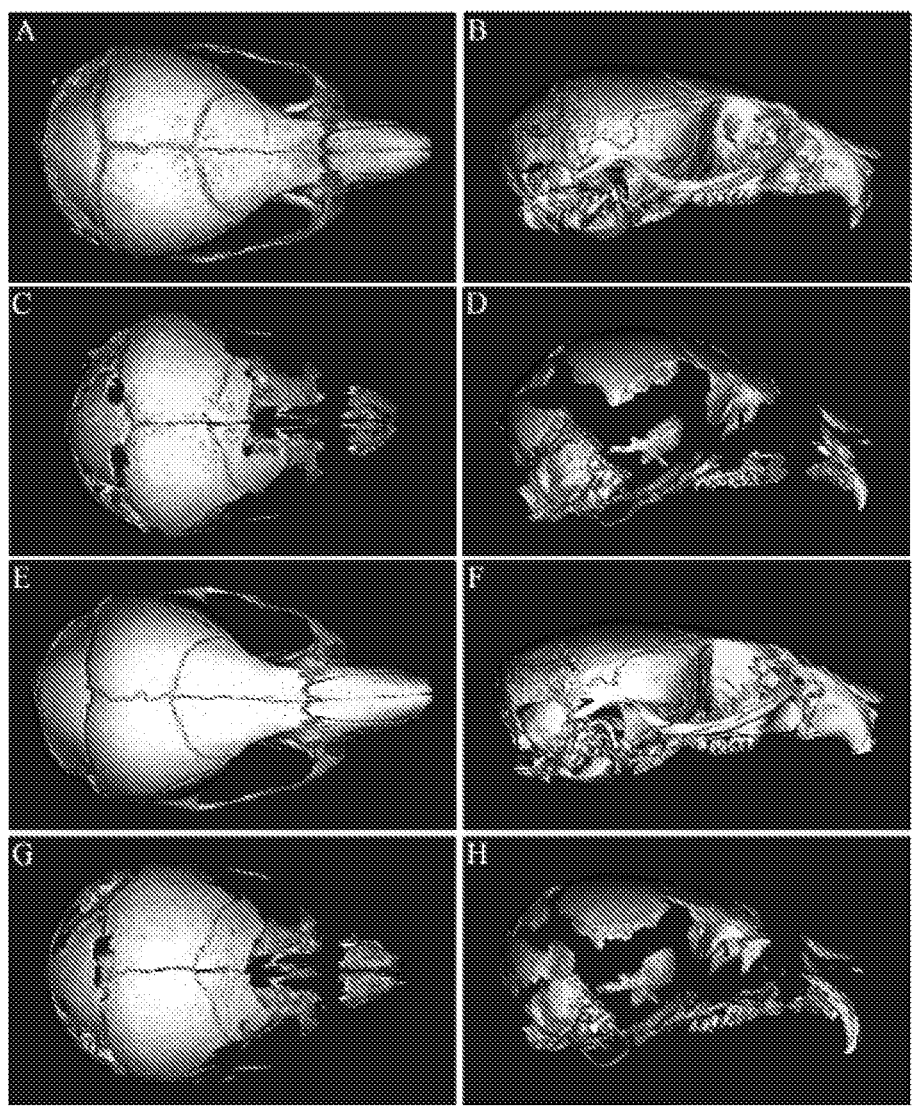
FIGS. 1A-1H are micro CT images showing that Alpl−/− mice exhibit craniofacial shape and mineralization abnormalities. Micro CT isosurface images of P15 Alpl+/+ (A,B), P15 Alpl−/− (C,D), and P20 Alpl+/+ (E,F) and P20 Alpl−/− (G,H) mouse skulls are shown.

As used herein, the term "subject" refers to any animal (e.g., a mammal), including, but not limited to, humans, non-human primates, rodents (e.g., mice, rats, etc.), flies, ovines, bovines, ruminants, lagomorphs, porcines, caprines, equines, canines, felines, ayes, and the like (e.g., which is to be the recipient of a particular treatment (e.g., treatment with an alkaline phosphates)). Typically, the terms "subject" and "patient" are used interchangeably, unless indicated otherwise herein.

As used herein, the term "animal" refers to any animal (e.g., a mammal), including, but not limited to, humans, non-human primates, rodents (e.g., mice, rats, etc.), flies, and the like.

As used herein, the term "non-human animals" refers to all non-human animals including, but are not limited to, vertebrates such as rodents, non-human primates, ovines, bovines, ruminants, lagomorphs, porcines, caprines, equines, canines, felines, ayes, etc.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length coding sequence or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, "gene replacement therapy" refers to administration to the recipient of exogenous genetic material encoding a therapeutic agent (e.g., an alkaline phosphatase) and subsequent expression of the administered genetic material in situ. Thus, the phrase "condition amenable to gene replacement therapy" embraces conditions such as genetic diseases (e.g., a disease condition that is attributable to one or more gene defects, such as craniosynostosis), and acquired pathologies (e.g., a pathological condition which is not attributable to an inborn defect).

As used herein, the term "therapeutic agent" refers to any agent or material, which has a beneficial effect on the recipient. Thus, "therapeutic agent" embraces both therapeutic and prophylactic molecules having, for example, a nucleic acid or protein component (e.g., a nucleic acid molecule encoding an alkaline phosphatase or an alkaline phosphatase polypeptide).

As used herein, the term "effective amount" refers to the amount of a composition or treatment sufficient to effect beneficial or desired results. An effective amount can be administered in one or more administrations, applications or dosages and is not intended to be limited to a particular formulation or administration route.

As used herein, the term "administration" refers to the act of giving a drug, prodrug, or other agent, or therapeutic treatment to a subject. Exemplary routes of administration to the human body can be through the eyes (ophthalmic), mouth (oral), skin (transdermal), nose (nasal), lungs (inhalant), oral mucosa (buccal), ear, by injection (e.g., intravenously, subcutaneously, intratumorally, intraperitoneally, etc.) and the like.

"Co-administration" refers to administration of more than one chemical agent or therapeutic treatment to a physiological system (e.g., a subject or in vivo, in vitro, or ex vivo cells, tissues, and organs). "Co-administration" of the respective agents (e.g., genetic therapies) and therapeutic treatments (e.g., surgery) may be concurrent, or in any temporal order or physical combination.

As used herein, "transfection of cells" refers to the acquisition by a cell of new genetic material by incorporation of an added nucleic acid molecule (e.g., DNA). Thus, transfection refers to the insertion of nucleic acid into a cell using physical or chemical methods. Several transfection techniques are known to those of ordinary skill in the art including: calcium phosphate DNA co-precipitation; DEAE-dextran; electroporation; cationic liposome-mediated transfection; and tungsten particle-faciliated microparticle bombardment. Strontium phosphate DNA co-precipitation is another possible transfection method.

"Gene delivery," "gene transfer," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art and described herein.

As used herein, "transduction of cells" refers to the process of transferring nucleic acid into a cell using a DNA or RNA virus. A RNA virus (e.g., a retrovirus) for transferring a nucleic acid into a cell is referred to herein as a transducing chimeric retrovirus. Exogenous genetic material contained within the retrovirus is incorporated into the genome of the transduced cell. A cell that has been transduced with a chimeric DNA virus (e.g., an adenovirus carrying a cDNA encoding a therapeutic agent), will not necessarily have the exogenous genetic material incorporated into its genome but will be capable of expressing the exogenous genetic material that is retained extrachromosomally within the cell.

A "gene delivery vehicle" is defined as any molecule that can carry inserted polynucleotides into a host cell. Examples of gene delivery vehicles include, but are not limited to, liposomes, biocompatible polymers, including natural polymers and synthetic polymers; lipoproteins; polypeptides; polysaccharides; lipopolysaccharides; artificial viral envelopes; metal particles; and bacteria, or viruses, such as baculovirus, adenovirus and retrovirus, bacteriophage, cosmid, plasmid, fungal vectors and other recombination vehicles typically used in the art which have been described for expression in a variety of eukaryotic and prokaryotic hosts, and may be used for gene therapy as well as for simple protein expression.

A "viral vector" is defined as a recombinantly produced virus or viral particle that comprises a polynucleotide to be delivered into a host cell, either in vivo, ex vivo, or in vitro. Examples of viral vectors include, but are not limited to, retroviral vectors, adenovirus vectors, adeno-associated virus vectors such as those described in W006002203A2, alphavirus vectors and the like. Alphavirus vectors, such as Semliki Forest virus-based vectors and Sindbis virus-based vectors, have also been developed for use in gene therapy and immunotherapy.

DETAILED DESCRIPTION OF THE INVENTION

Provided herein are compositions and methods for treating craniosynostosis. In particular, provided herein are methods of treating and preventing craniosynostosis. In some embodiments, administration of the compositions and methods results in reversal of craniosynostosis or a reduction in the extent or severity of one or more symptoms of craniosynostosis (e.g., intracranial pressure, abnormal cranial bone mineralization, abnormal physical examination, or abnormal radiographic results.

Experiments conducted during the course of development of embodiments of the present disclosure demonstrated that (1) FGF receptor activity inhibits tissue-nonspecific alkaline phosphatase (TNAP) expression; (2) TNAP regulates bone mineralization and growth; and (3) craniosynostosis also occurs at high rates in children with inactivating mutations in the gene for TNAP. The technology described herein is not limited to a particular mechanism. Indeed, an understanding of the mechanism is not necessary to practice the present invention. Nonetheless, it is contemplated that activating mutations in FGF receptors inhibit TNAP expression, leading to abnormal cranial bone mineralization and craniosynostosis.

Hypophosphatasia (HPP) is a rare metabolic disorder that features osteomalacia due to loss-of function mutations in the gene (Alpl) encoding tissue-nonspecific alkaline phosphatase (TNAP). Recent reports demonstrated that injection of a mineral-targeted form of TNAP in infants and children with debilitating HPP dramatically improves skeletal mineralization, yet a high incidence of craniosynostosis (the premature fusion of cranial bones) remains in these patients.

Further experiments conducted during the course of development of embodiments of the present disclosure demonstrated that injection with a lentivirus expressing a bone-targeted recombinant form of TNAP diminished the severity of craniosynostosis in mice that carry the most common human craniosynostosis-associated mutation in FGFR2 (the FGFR2-C342R mouse model of Crouzon craniosynostosis). Micro-CT, histologic and digital caliper based analyses showed that the skulls of treated P15 Alpl−/− mice (n=44) are significantly different than those of untreated Alpl−/− mice, but not significantly different than those of wild type mice (n=45). These findings demonstrate that post-natal TNAP enzyme replacement therapy is efficacious for preventing HPP-associated craniofacial skeletal abnormalities when initiated shortly after birth. Results also indicated that the influence of TNAP on craniofacial skeletal development extends beyond that of promoting hydroxyapatite crystal growth, and includes both osteoblastic and chondrocytic routes.

TNAP enzyme replacement rescued the cranial bone hypomineralization seen in Alpl−/− mice. Multiple facial bones of untreated Alpl−/− mice, for example, are so hypomineralized that they do not appear on micro CT scans constrained to a bone tissue threshold. This is not the case in treated Alpl−/− mice. TNAP enzyme replacement also rescued a localized and transient cranial bone hypermineralization phenotype in Alpl−/− mice. Increased bone volume, density and mineral content is seen in frontal bones of two week-old untreated Alpl−/− mice. This cranial bone specific hypermineralization phenotype is not seen in treated Alpl−/− mice. These results indicate that a transient hypermineralization phenotype occurs in Alpl−/− frontal bones and that TNAP enzyme replacement diminishes this phenotype.

Further results presented here (See e.g., Example 3) demonstrate that daily subcutaneous injections of mineral-targeted TNAP initiated shortly after birth can prevent craniosynostosis in murine infantile HPP. Approximately one third of untreated Alpl−/− mice develop craniosynostosis in the form of bony coronal suture fusion by three weeks after birth (Liu et al, Bone. 2014; 67:81-94). No Alpl−/− mice treated with daily with injections of 2.0 or 8.2 mg/kg/day of mineral-targeted TNAP showed any evidence of craniosynostosis as assessed by microscopic visualization of dissected skulls, micro CT or histology. This data indicates that TNAP enzyme replacement is efficacious for preventing HPP-associated craniosynostosis when the onset is postnatal. Craniosynostosis cannot be reversed after it has occurred therefore any preventive treatment should be initiated prior to the onset of craniosynostosis. Clinical manifestations of HPP can first appear after birth in some infants (Seuya et al., J Craniofac Surg. 2013; 24(1):96-8), indicating that the onset of craniosynostosis and therefore a therapeutic window for prevention may be postnatal in some patients.

Treatment with mineral-targeted TNAP also diminished craniofacial skeletal shape abnormalities in murine HPP. Untreated Alpl−/− mice exhibit an acrocephalic and brachycephalic skull shape (tall, wide and shorter in anterior-poster length), similar to that seen in some infants affected with HPP (Liu et al, Bone. 2014; 67:81-94; Fraser D. Hypophosphatasia. Am J Med. 1957; 22(5):730-46). Treated Alpl−/− mice have skulls that are more similar to those of wild type mice. Skulls of treated Alpl−/− mice are less tall, less wide and longer in anterior-posterior length than those of untreated Alpl−/− mice, as assessed using digital calipers or landmark coordinate data from micro CT scans. This difference in shape is consistent with the rescue of coronal suture fusion seen in the treated mice, as this location of craniosynostosis is associated limited anterior-posterior skull growth with compensating vertical and transverse growth (DP Rice, Developmental Anatomy of Craniofacial Sutures, in: D P Rice (Ed.), Craniofacial Sutures Development, Disease and Treatment; Karger, Switzerland 2008; Cohen M M Jr. Am J Med Genet. 1993; 47:581-616; Morriss-Kay G M, et al., J Anat. 2005; 207(5):637-53).

Accordingly, embodiments of the present disclosure provide compositions, systems, and methods for treating and preventing craniosynostosis or the extent or severity of one or more symptoms of craniosynostosis. In some embodiments, craniosynostosis is treated or prevented by replacing alkaline phosphatase is individuals diagnosed with or at risk of developing craniosynostosis. In some embodiments, genetic therapies are utilized.

I. Alkaline Phosphatase Replacement

Embodiments of the present disclosure provide compositions and methods for alkaline phosphatase replacement therapy. In some embodiments, replacement therapy is genetic therapy (e.g. introducing nucleic acids expressing alkaline phosphatase into a subject in need thereof) or alkaline phosphatase enzyme replacement therapy.

The present disclosure is not limited to a particular alkaline phosphatase polypeptide or nucleic acid sequence encoding the polypeptide. For example, any protein or polypeptide containing alkaline phosphatase (ALP) activity or the nucleic acid encoding such protein or polypeptide may be used for treating craniosynostosis. Exemplary ALPs include tissue non-specific alkaline phosphatase (TNAP or TNALP), placental alkaline phosphatase (PALP) (e.g., as described in NCBI Reference Sequences [NP_112603] and [NP_001623]), germ cell alkaline phosphatase (GCALP) (e.g., as described in UniProtKB Reference Sequence [P10696]), and intestinal alkaline phosphatase (IALP) (e.g., as described in NCBI Reference Sequence [NP_001622]). These enzymes possess very similar three-dimensional structure. Each of their catalytic sites contains four metal binding domains for metal ions necessary for enzymatic activity including two Zn and one Mg. These enzymes catalyze the hydrolysis of monoesters of phosphoric acid and also catalyze a transphosphorylation reaction in the presence of high concentrations of phosphate acceptors. It has been shown in particular that PALP is physiologically active toward phosphoethanolamine (PEA), inorganic pyrophosphate (PPi) and pyridoxal 5'-phosphate (PLP), all three being known natural substrate for TNALP (Whyte, 1995). Besides the four exemplary ALPs discussed above, this disclosure also provides any other protein or polypeptide comprising the identical or similar catalytic site structure and/or enzymatic activity for treating craniosynostosis. For a complete discussion of ALP constructs, especially TNALP conjugates, please see PCT publication Nos: WO2005103263 and WO2008138131, the content of both of which are incorporated herein by reference to their entirety.

In one embodiment, TNALP is a membrane-bound protein anchored through a glycolipid to its C-terminal (Swiss-Prot, P05186). This glycolipid anchor (GPI) is added post translationally after removal of a hydrophobic C-terminal end which serves both as a temporary membrane anchor and as a signal for the addition of the GPI. Hence this disclosure provides both full-length TNALP and TNALP fragments, either with or without the GPI anchor. In some embodiments, the disclosure provides herein a soluble TNALP construct without the GPI anchor. In one embodiment, the disclosure provides a soluble TNALP construct wherein the first amino acid of the hydrophobic C-terminal sequence of TNALP, namely alanine, is replaced by a stop codon. The soluble TNALP (herein called sTNALP) so formed contains all amino acids of the native anchored form of TNALP necessary for the formation of the catalytic site but lacks the GPI membrane anchor. Known TNALP include human TNALP [NP-000469, AAI10910, AAH90861, AAH66116, AAH21289, AAI26166], rhesus TNALP [XP-001109717], rat TNALP [NP_037191], dog TNALP [AAF64516], pig TNALP [AAN64273], mouse [NP_031457], bovine [NP_789828, NP_776412, AAM 8209, AAC33858], and cat [NP_001036028]. In some embodiments, the TNAP is a recombinant human TNAP enzyme (e.g., asfotase alfa; see U.S. Pat. Nos. 7,763,712 and 7,960,529, incorporated herein by reference) for the prevention and/or treatment of craniosynostosis in mice and/or in humans.

The present disclosure also encompasses sequences satisfying a consensus sequence derived from the extracellular domain of human ALP isozymes (e.g., TNALP, PALP, GCALP, IALP, etc.). As used herein the terminology "extracellular domain" is meant to refer to any functional extracellular portion of the native protein (i.e. without the peptide signal). Thus, similar to sTNALP discussed above, the present disclosure also provides other soluble human ALP isozymes, preferably comprising the extracellular domain of such ALPs. It has been shown that recombinant sTNALP retaining original amino acids 1 to 501 (18 to 501 when secreted) (see Oda et al., J. Biochem 126: 694-699, 1999), amino acids 1 to 504 (18 to 504 when secreted) (U.S. Pat. No. 6,905,689 to Bernd et al.) and amino acids 1 to 505 (18-505 when secreted) (US 2007/0081984 to Tomatsu et al.), are enzymatically active. Also presented herein is a recombinant sTNALP retaining amino acids 1 to 502 (18 to 502 when secreted) (FIG. 3) of the original TNALP is enzymatically active. This indicates that amino acid residues can be removed from the C-terminal end of the native protein without affecting its enzymatic activity.

In some embodiments, the protein or polypeptide for replacement therapy comprises a structure: X-protein-Y, wherein X is absent or is an amino acid sequence of at least one amino acid and Y is absent or is an amino acid sequence of at least one amino acid. In one embodiment, X and/or Y is fused to the protein or polypeptide described herein to facilitate or increase the protein or polypeptide production and/or function. For example, X and/or Y may comprise a sequence for purification of the recombinant protein or polypeptide (e.g., His6, FLAG, GST, or any others known tags in the art), a sequence for modifying the recombinant protein or polypeptide (e.g., to increase or decrease its glycosylation, PEGylation, ubiquitination, sialylation, etc.), a sequence for increasing the solubility of the recombinant protein or polypeptide, a sequence for increasing the stability of the recombinant protein or polypeptide (e.g., Fc or other immunoglobulin fragments), a sequence for increasing the enzymatic activity of the recombinant protein or polypeptide (e.g., full-length ALP or ALP fragments), a sequence for decreasing the immunogenicity of the recombinant protein or polypeptide, and/or a sequence for modifying in vivo distribution or localization of the recombinant protein or polypeptide (e.g., a bone-targeting signal, a liver-targeting signal, etc.). In one embodiment, X and/or Y is a bone-targeting signal.

This disclosure further provides a bone delivery conjugate comprising a structure selected from the group consisting of: A) Z-protein-Y-Wn-X; and B) X-Wn-Y-protein-Z. Any one of X, Y, and Z is absent or is an amino acid sequence of at least one amino acid. The Wn is a bone delivery moiety. Exemplary Wn includes, but not limited to, poly-aspartate and poly-glutamate. Exemplary n may be any number no smaller than 3, e.g., 3, 4, 5, 6, 7, 8, 9, 10, 11, 12, 13, 14, 15, 16, 17, 18, 19, 20 and more. In some embodiments, n=6. In other embodiments, n=10 to 16. In another specific embodiment of the present invention, the protein in the bone delivery conjugate is a soluble phosphate regulating gene with homology to endopeptidases on the X chromosome (sPHEX). In another specific embodiment of the present invention, the protein in the conjugate is a soluble alkaline phosphatase (sALP). In one embodiment, the structure of the conjugate is: Z-sALP-Y-Dn-X. The sALP may be any soluble ALPs (such as TNALP, PALP, GCALP and IALP). In some preferred embodiments, the sALP is TNALP. In one embodiment, the sALP has an amino acid sequence encoded by the sequence as set forth in SEQ ID NO: 1. In another preferred embodiment, the sALP has an amino acid sequence as set forth in SEQ ID NO: 2. In a preferred embodiment, n is 10. In another embodiment, n is 11. In a further specific embodiment, n is 12. In another specific embodiment, n is 13. In a further specific embodiment, n is 14. In a still further specific embodiment, n is 15. In a further specific embodiment, n is 16. In some embodiments, the conjugate comprises the structure of sALP-$D_{10}$. In one embodiment, the sALP-$D_{10}$ conjugate has an amino acid sequence encoded by a nucleic acid sequence as set forth in SEQ ID NO: 3. In another embodiment, the sALP-$D_{10}$ conjugate has an amino acid sequence as set forth in SEQ ID NO: 4. In other embodiments, the conjugate comprises a structure of $D_{10}$-sALP.

The disclosure further provides herein a bone delivery conjugate comprising a structure selected from the group consisting of: Z-sALP-Y-spacer-X-Wn-V, Z-Wn-X-spacer-Y-sALP-V, Z-sALP-Y-Wn-X-spacer-V, and Z-Wn-X-sALP-Y-spacer-V. In some preferred embodiments, the conjugate comprises a structure: Z-sALP-Y-spacer-X-Wn-V or Z-Wn-X-spacer-Y-sALP-V. Any one of X, Y, Z, and V may be absent or an amino acid sequence of at least one amino acid. The sALP comprises the full-length or functional fragments of ALPs. In one embodiment, the sALP comprises the extracellular domain of the alkaline phosphatase. In some embodiments, the Wn is a polyaspartate or a polyglutamate. In one embodiments, n=10 to 16. In other embodiments, the Wn is any negatively charged peptide. In some embodiments, the conjugate comprises a structure of hTNALP-Fc-$D_{10}$. In one embodiment, the hTNALP-Fc-$D_{10}$ conjugate has an amino acid sequence encoded by a nucleic acid sequence as set forth in SEQ ID NO: 6 (including the N-terminal peptide signal). In another preferred embodiment, the hsTNALP-Fc-$D_{10}$ conjugate (without the N-terminal peptide signal) has an amino acid sequence as set forth in SEQ ID NO: 7.

In some embodiments, the spacer in the conjugate is an Fc fragment. Without being limited to this theory, it is believed that the Fc fragment allows the conjugate to be more efficiently folded. For example, the expression of a sTNALP-Fc-$D_{10}$ conjugate was higher than that of sTNALP-D10 (see Example 2 of PCT Publication No. WO2008138131, which is incorporated by reference herein in its entirety). One possible explanation is that the introduction of the Fc fragment alleviates the repulsive forces caused by the presence of the highly negatively charges $D_{10}$ sequence added at the C-terminus of the tested sALP sequence. Without being limited to this theory, a conjugate having Fc as the spacer may also have increased in vivo stability and longer serum half-life. Such Fc fragment may have normal effector function or reduced or no effector function. In some embodiments of the present disclosure, the spacer comprises a fragment crystallizable region (Fc). In one embodiment, the Fc comprises a CH2 domain, a CH3 domain and a hinge region. In another embodiment, the Fc is a constant domain of an immunoglobulin selected from the group consisting of IgG-1, IgG-2, IgG-3 and IgG-4. An exemplary amino acid sequence of the IgG1-Fc is set forth in SEQ ID NO: 5.

Useful spacers include, but are not limited to, polypeptides comprising a Fc, and hydrophilic and flexible polypeptides able to alleviate the repulsive forces caused by the presence of the terminal highly negatively charged peptide (e.g., Wn). In one embodiment, the spacer alleviates the steric hindrance preventing two sALP domains from two sALP monomers from interacting with each other to constitute the minimal catalytically active entity.

In some embodiments, alkaline phosphatase enzyme replacement therapy comprises providing an isolated alkaline phosphatase polypeptide to a subject (e.g., the alkaline phosphatase polypeptides described herein.

In some embodiments, constructs (e.g., vectors) for alkaline phosphatase replacement therapy comprise a bone-targeting component (e.g., bone-specific promoter). The present disclosure is not limited to a particular bone-specific promoter. Examples include, but are not limited to, the osteocalcin promoter. In some embodiments, the bone targeting sequence is a deca-aspartate motif. For example, in some embodiments, the mineral/bone-targeted recombinant form of alkaline phosphatase enzyme contains recombinant human soluble alkaline phosphatase (Alpl), the constant region of human IgG1 Fc domain (Fc) to enhance stability, and a deca-aspartate motif to confer binding to mineral (e.g., bone).

In some embodiments, gene knock-in methods utilize introduction of nucleic acids encoding alkaline phosphatase (e.g., under the control of a bone-specific promoter).

Introduction of molecules carrying genetic information into cells is achieved by any of various methods including, but not limited to, directed injection of naked DNA constructs, bombardment with gold particles loaded with said constructs, and macromolecule mediated gene transfer using, for example, liposomes, biopolymers, and the like. In some embodiments, delivery of naked DNA utilizes organically modified silica or silicate (ormosil).

In some embodiments, methods use gene delivery vehicles derived from viruses, including, but not limited to, adenoviruses, retroviruses, vaccinia viruses, and adeno-associated viruses.

Retroviruses are one of the mainstays of current gene therapy approaches. The recombinant retroviruses such as the Moloney murine leukemia virus have the ability to integrate into the host genome in a stable fashion. They contain a reverse transcriptase that allows integration into the host genome.

Retroviral vectors can either be replication-competent or replication-defective. Replication-defective vectors are the most common choice because the viruses have had the coding regions for the genes necessary for additional rounds of virion replication and packaging replaced with other genes, or deleted. These viruses are capable of infecting their target cells and delivering their viral payload, but then fail to continue the typical lytic pathway that leads to cell lysis and death.

Conversely, replication-competent viral vectors contain all necessary genes for virion synthesis, and continue to propagate themselves once infection occurs. Because the viral genome for these vectors is much lengthier, the length of the actual inserted gene of interest is limited compared to the possible length of the insert for replication-defective vectors. Depending on the viral vector, the typical maximum length of an allowable DNA insert in a replication-defective viral vector is usually about 8-10 kB. While this limits the introduction of many genomic sequences, most cDNA sequences can still be accommodated.

Lentiviruses are a subclass of Retroviruses. They have been adapted as gene delivery vehicles (vectors) thanks to their ability to integrate into the genome of non-dividing cells, which is the unique feature of Lentiviruses as other Retroviruses can infect only dividing cells. The viral genome in the form of RNA is reverse-transcribed when the virus enters the cell to produce DNA, which is then inserted into the genome at a random position by the viral integrase enzyme. The vector, now called a provirus, remains in the genome and is passed on to the progeny of the cell when it divides. The provirus can disturb the function of cellular genes and lead to activation of oncogenes promoting the development of cancer, which raises concerns for possible applications of lentiviruses in gene therapy. However, studies have shown that lentivirus vectors have a lower tendency to integrate in places that potentially cause cancer than gamma-retroviral vectors.

For safety reasons lentiviral vectors are typically engineered without the genes required for their replication. To produce a lentivirus, several plasmids are transfected into a so-called packaging cell line, commonly HEK 293. One or more plasmids, generally referred to as packaging plasmids, encode the virion proteins, such as the capsid and the reverse transcriptase. Another plasmid contains the genetic material to be delivered by the vector. It is transcribed to produce the single-stranded RNA viral genome and is marked by the presence of the ψ (psi) sequence. This sequence is used to package the genome into the virion.

Adeno-associated virus (AAV) is a small virus that infects humans and some other primate species. AAV is not currently known to cause disease and consequently the virus causes a very mild immune response. AAV can infect both dividing and non-dividing cells and may incorporate its genome into that of the host cell. These features make AAV a very attractive viral vector for gene therapy.

Furthermore, because of its use as a gene therapy vector, researchers have created an altered AAV called Self-complementary adeno-associated virus (scAAV). Whereas AAV packages a single strand of DNA and requires the process of second-strand synthesis, scAAV packages both strands which anneal together to form double stranded DNA. By skipping second strand synthesis scAAV allows for rapid expression in the cell (McCarty, D M; Monahan, P E; Samulski, R J (2001). "Self-complementary recombinant adeno-associated virus (scAAV) vectors promote efficient transduction independently of DNA synthesis". Gene Therapy 8 (16): 1248-54). Otherwise, scAAV carries many characteristics of its AAV counterpart.

Because of the higher efficiency as compared to retroviruses, vectors derived from adenoviruses are the preferred gene delivery vehicles for transferring nucleic acid molecules into host cells in vivo. The adenoviruses (Ads) comprise a large family of double-stranded DNA viruses found in amphibians, avians, and mammals which have a nonenveloped icosahedral capsid structure (Straus, Adenovirus infections in humans. In The Adenoviruses. 451-498, 1984; Hierholzer et al., J. Infect. Dis., 158: 804-813, 1988; Schnurr and Dondero, Intervirology., 36: 79-83, 1993; Jong et al., J Clin Microbiol., 37:3940-3945:1999). In contrast to retroviruses, adenoviruses can transduce numerous cell types of several mammalian species, including both dividing and nondividing cells, without integrating into the genome of the host cell.

Generally speaking, adenoviral DNA is typically very stable and remains episomal (e.g., extrachromosomal), unless transformation or tumorigenesis has occurred. In addition, adenoviral vectors can be propagated to high yields in well-defined production systems which are readily amenable to pharmaceutical scale production of clinical grade compositions. Typically, the production of recombinant adenoviral vectors relies on the use of a packaging cell line which is capable of complementing the functions of adenoviral gene products that have been either deleted or engineered to be nonfunctional.

Presently, two well-characterized human subgroup C adenovirus serotypes (i.e., hAd2 and hAd5) are widely used as the sources of the viral backbone for most of the adenoviral vectors that are used for genetic therapy. Replication-defective human adenoviral vectors have also been used. Examples of adenoviral vectors and methods for gene transfer are described in PCT publications WO 00/12738 and WO 00/09675 and U.S. Pat. Nos. 6,033,908, 6,019,978, 6,001, 557, 5,994,132, 5,994,128, 5,994,106, 5,981,225, 5,885,808, 5,872,154, 5,830,730, and 5,824,544, each of which is herein incorporated by reference in its entirety.

Methods of delivery of viral vectors include, but are not limited to, intra-arterial, intra-muscular, intravenous, intranasal and oral routes. Generally, rAAV or other virions may be introduced into skeletal cells using either in vivo or in vitro transduction techniques. If transduced ex vivo, the desired recipient cell is removed from the subject, transduced with rAAV virions and reintroduced into the subject. Alternatively, syngeneic or xenogeneic cells can be used where those cells will not generate an inappropriate immune response in the subject.

Suitable methods for the delivery and introduction of transduced cells into a subject have been described. For example, cells can be transduced ex vivo by combining recombinant AAV virions with bone cells e.g., in appropriate media, and screening for those cells harboring the DNA of interest can be screened using conventional techniques such as Southern blots and/or PCR, or by using selectable markers. Transduced cells can then be formulated into pharmaceutical compositions, described more fully below, and the composition introduced into the subject by various techniques, such as by grafting, intramuscular, intravenous, subcutaneous and intraperitoneal injection.

In one embodiment, for in vivo delivery, the rAAV virions are formulated into pharmaceutical compositions and will generally be administered parenterally, e.g., by intramuscular injection directly into skeletal or cardiac muscle or by injection.

In one embodiment, pharmaceutical compositions comprise sufficient genetic material to produce a therapeutically effective amount of the nucleic acid of interest, i.e., an amount sufficient to reduce or ameliorate symptoms of the disease state in question or an amount sufficient to confer the desired benefit. The pharmaceutical compositions also contains a pharmaceutically acceptable excipient. Such excipients include any pharmaceutical agent that does not itself induce the production of antibodies harmful to the individual receiving the composition, and which may be administered without undue toxicity. Pharmaceutically acceptable excipients include, but are not limited to, sorbitol, TWEEN80, and liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in Remington's Pharmaceutical Sciences (Mack Pub. Co., N.J. 1991).

An effective amount of viral vector to be added can be empirically determined. Administration can be effected in one dose, continuously or intermittently throughout the course of treatment. Methods of determining the most effective means and dosages of administration are well known to those of skill in the art and will vary with the viral vector, the composition of the therapy, the target cells, and the subject being treated. Single and multiple administrations can be carried out with the dose level and pattern being selected by the treating physician.

It should be understood that more than one transgene can be expressed by the delivered viral vector. Alternatively, separate vectors, each expressing one or more different transgenes, can also be delivered as described herein. Furthermore, it is also intended that the viral vectors delivered by the methods of the present disclosure be combined with other suitable compositions and therapies.

The exogenous genetic material (e.g., a cDNA encoding alkaline phosphatase) is introduced into the cell ex vivo or in vivo by genetic transfer methods, such as transfection or transduction, to provide a genetically modified cell.

Typically, the exogenous genetic material includes the heterologous gene (usually in the form of a cDNA comprising the exons coding for the therapeutic protein) together with a promoter to control transcription of the new gene. The promoter characteristically has a specific nucleotide sequence necessary to initiate transcription. Optionally, the exogenous genetic material further includes additional sequences (e.g., enhancers) to obtain the desired gene transcription activity. For the purpose of this discussion an "enhancer" is simply any non-translated DNA sequence which works contiguous with the coding sequence (in cis) to change the basal transcription level dictated by the promoter. The exogenous genetic material may be introduced into the cell genome immediately downstream from the promoter so that the promoter and coding sequence are operatively linked so as to permit transcription of the coding sequence. A retroviral expression vector may include an exogenous promoter element to control transcription of the inserted exogenous gene. Such exogenous promoters include both constitutive and inducible promoters.

Naturally-occurring constitutive promoters control the expression of essential cell functions. As a result, a gene under the control of a constitutive promoter is expressed under all conditions of cell growth. Exemplary constitutive promoters include the promoters for the following genes which encode certain constitutive or "housekeeping" functions: hypoxanthine phosphoribosyl transferase (HPRT), dihydrofolate reductase (DHFR), adenosine deaminase, phosphoglycerol kinase (PGK), pyruvate kinase, phosphoglycerol mutase, the actin promoter, and other constitutive promoters known to those of skill in the art. In addition, many viral promoters function constitutively in eucaryotic cells. These include: the early and late promoters of SV40; the long terminal repeats (LTRs) of Moloney Leukemia Virus and other retroviruses; and the thymidine kinase promoter of Herpes Simplex Virus, among many others. Accordingly, any of the above-referenced constitutive promoters can be used to control transcription of a heterologous gene insert.

Genes that are under the control of inducible promoters are expressed only or to a greater degree, in the presence of an inducing agent, (e.g., transcription under control of the metallothionein promoter is greatly increased in presence of certain metal ions). Inducible promoters include responsive elements (REs) which stimulate transcription when their inducing factors are bound. For example, there are REs for serum factors, steroid hormones, retinoic acid and cyclic AMP. Promoters containing a particular RE can be chosen in order to obtain an inducible response and in some cases, the RE itself may be attached to a different promoter, thereby conferring inducibility to the recombinant gene. Thus, by selecting the appropriate promoter (constitutive versus inducible; strong versus weak), it is possible to control both the existence and level of expression of a therapeutic agent in the genetically modified cell. If the gene encoding the therapeutic agent is under the control of an inducible promoter, delivery of the therapeutic agent in situ is triggered by exposing the genetically modified cell in situ to conditions for permitting transcription of the therapeutic agent, e.g., by intraperitoneal injection of specific inducers of the inducible promoters which control transcription of the agent. For example, in situ expression by genetically modified cells of a therapeutic agent encoded by a gene under the control of the metallothionein promoter, is enhanced by contacting the genetically modified cells with a solution containing the appropriate (i.e., inducing) metal ions in situ.

Accordingly, the amount of therapeutic agent that is delivered in situ is regulated by controlling such factors as: (1) the nature of the promoter used to direct transcription of the inserted gene, (e.g., whether the promoter is constitutive or inducible, strong or weak, or tissue specific); (2) the number of copies of the exogenous gene that are inserted into the cell; (3) the number of transduced/transfected cells that are administered (e.g., implanted) to the patient; (4) the size of the implant (e.g., graft or encapsulated expression system); (5) the number of implants; (6) the length of time the transduced/transfected cells or implants are left in place; and (7) the production rate of the therapeutic agent by the genetically modified cell. Selection and optimization of these factors for delivery of a therapeutically effective dose of a particular therapeutic agent is determined by taking into account the above-disclosed factors and the clinical profile of the patient.

In addition to at least one promoter and at least one heterologous nucleic acid encoding the therapeutic agent, the expression vector may include a selection gene, for example, a neomycin resistance gene, for facilitating selection of cells that have been transfected or transduced with the expression vector. Alternatively, the cells are transfected with two or more expression vectors, at least one vector containing the gene(s) encoding the therapeutic agent(s), the other vector containing a selection gene.

The therapeutic agent can be targeted for delivery to an extracellular, intracellular or membrane location. If it is desirable for the gene product to be secreted from the cells, the expression vector is designed to include an appropriate secretion "signal" sequence for secreting the therapeutic gene product from the cell to the extracellular milieu. If it is desirable for the gene product to be retained within the cell, this secretion signal sequence is omitted. In a similar manner, the expression vector can be constructed to include "retention" signal sequences for anchoring the therapeutic agent within the cell plasma membrane. For example, all membrane proteins have hydrophobic transmembrane regions, which stop translocation of the protein in the membrane and do not allow the protein to be secreted. The construction of an expression vector including signal sequences for targeting a gene product to a particular location is deemed to be within the scope of one of ordinary skill in the art without the need for undue experimentation.

In some embodiments, ex vivo methods comprise the transfer of genetic material into skeletal or bone cells or tissues (e.g., including but not limited to, chondrocytes, osteoclasts, osteoblasts, and osteocytes).

II. Treatment Methods

Embodiments of the present disclosure provide methods of treating or preventing craniosynostosis (e.g., via genetic therapy as described above or via administration of alkaline phosphatase (e.g., TNAP) polypeptides (e.g., asfotase alfa)). In some embodiments, treatment is administered to subjects (e.g., neonatal subjects) diagnosed with or at risk of craniosynostosis. In some embodiments, the subject exhibits one or more symptoms or signs of craniosynostosis (e.g., increased intracranial pressure, abnormal cranial bone mineralization, abnormal physical examination, or abnormal radiographic results).

In some embodiments, the subject has a mutation in an FGFR (e.g., FGFR1, FGFR2, or FGFR3) or Alph1 gene. In some embodiments, the subject is tested for the mutation prior to or after providing the exogenous alkaline phosphatase nucleic acid. In some embodiments, parents are tested prior to or during pregnancy. In some embodiments, fetal samples (e.g., fetal nucleic acid obtained from maternal blood samples, placental, or fetal samples) are tested.

In some embodiments, the subject has hypophosphatasia (HPP) and treatment prevents craniosynostosis associated with HPP.

In some embodiments, treatment is initiated in the neonatal period (e.g., within 1 hour, 8 hours, 12 hours, 1 day, 2 days, 3 days, 4 days, 5 days, 6 days, 1 week, 2, weeks, 3 weeks, or one month) of birth.

In some embodiments, treatment is initiated prior to birth. For example, in some embodiments, treatment is initiated in utero. In some embodiments, treatment is initiated during the embryonic stage (e.g., during in vitro fertilization).

In some embodiments, treatment is repeated at least once. In some embodiments, multiple doses are delivered over time to achieve a desired effect, and often, each dose delivers an effective amount of alkaline phosphatase polypeptide in the form of an isolated alkaline phosphatase polypeptide or a nucleic acid encoding the peptide. For example, in some embodiments, nucleic acids encoding alkaline phosphatase are administered daily, weekly, monthly, annually, or less often. In some embodiments, treatment is stopped after a period of time and re-started at a later date.

III. Compositions and Delivery

Provided herein is a composition for treating or preventing craniosynostosis in a subject. Such compositions comprise, for example, a polypeptide or a polynucleotide encoding such polypeptide, which is capable of increasing the activity and/or the expression levels of alkaline phosphatase in said subject. The polypeptide may be the isolated or recombinant alkaline phosphatase, or any polypeptide capable of increasing the activity and/or the expression levels of such alkaline phosphatase. For a detailed discussion of the alkaline phosphastase, please see above discussion of method of treatment.

The compositions described herein can be formulated as a pharmaceutical solution, e.g., for administration to a subject for the treatment or prevention of a complement-associated disorder. The pharmaceutical compositions will generally include a pharmaceutically acceptable carrier. As used herein, a "pharmaceutically acceptable carrier" refers to, and includes, any and all solvents, dispersion media, coatings, antibacterial and antifungal agents, isotonic and absorption delaying agents, and the like that are physiologically compatible. The compositions can include a pharmaceutically acceptable salt, e.g., an acid addition salt or a base addition salt (see, e.g., Berge et al. (1977) *J Pharm Sci* 66:1-19).

The compositions can be formulated according to standard methods. Pharmaceutical formulation is a well-established art, and is further described in, e.g., Gennaro (2000) "Remington: The Science and Practice of Pharmacy," 20$^{th}$ Edition, Lippincott, Williams & Wilkins (ISBN: 0683306472); Ansel et al. (1999) "Pharmaceutical Dosage Forms and Drug Delivery Systems," 7$^{th}$ Edition, Lippincott Williams & Wilkins Publishers (ISBN: 0683305727); and Kibbe (2000) "Handbook of Pharmaceutical Excipients American Pharmaceutical Association," 3$^{rd}$ Edition (ISBN: 091733096X). In some embodiments, a composition can be formulated, for example, as a buffered solution at a suitable concentration and suitable for storage at 2-8° C. (e.g., 4° C.). In some embodiments, a composition can be formulated for storage at a temperature below 0° C. (e.g., −20° C. or −80° C.). In some embodiments, the composition can be formulated for storage for up to 2 years (e.g., one month, two months, three months, four months, five months, six months, seven months, eight months, nine months, 10 months, 11 months, 1 year, 1½ years, or 2 years) at 2-8° C. (e.g., 4° C.). Thus, in some embodiments, the compositions described herein are stable in storage for at least 1 year at 2-8° C. (e.g., 4° C.).

The pharmaceutical compositions can be in a variety of forms. These forms include, e.g., liquid, semi-solid and solid dosage forms, such as liquid solutions (e.g., injectable and infusible solutions), dispersions or suspensions, tablets, pills, powders, liposomes and suppositories. The preferred form depends, in part, on the intended mode of administration and therapeutic application. For example, compositions containing a composition intended for systemic or local delivery can be in the form of injectable or infusible solutions. Accordingly, the compositions can be formulated for administration by a parenteral mode (e.g., intravenous, subcutaneous, intraperitoneal, or intramuscular injection). "Parenteral administration," "administered parenterally," and other grammatically equivalent phrases, as used herein, refer to modes of administration other than enteral and topical administration, usually by injection, and include, without limitation, intravenous, intranasal, intraocular, pulmonary, intramuscular, intraarterial, intrathecal, intracapsular, intraorbital, intracardiac, intradermal, intrapulmonary, intraperitoneal, transtracheal, subcutaneous, subcuticular, intraarticular, subcapsular, subarachnoid, intraspinal, epidural, intracerebral, intracranial, intracarotid and intrasternal injection and infusion (see below).

The compositions can be formulated as a solution, microemulsion, dispersion, liposome, or other ordered structure suitable for stable storage at high concentration. Sterile injectable solutions can be prepared by incorporating a composition described herein in the required amount in an appropriate solvent with one or a combination of ingredients enumerated above, as required, followed by filter sterilization. Generally, dispersions are prepared by incorporating a composition described herein into a sterile vehicle that contains a basic dispersion medium and the required other ingredients from those enumerated above. In the case of sterile powders for the preparation of sterile injectable solutions, methods for preparation include vacuum drying and freeze-drying that yield a powder of a composition described herein plus any additional desired ingredient (see below) from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition a reagent that delays absorption, for example, monostearate salts, and gelatin.

The compositions described herein can also be formulated in immunoliposome compositions. Such formulations can be prepared by methods known in the art such as, e.g., the methods described in Epstein et al. (1985) *Proc Natl Acad Sci USA* 82:3688; Hwang et al. (1980) *Proc Natl Acad Sci USA* 77:4030; and U.S. Pat. Nos. 4,485,045 and 4,544,545. Liposomes with enhanced circulation time are disclosed in, e.g., U.S. Pat. No. 5,013,556.

In certain embodiments, compositions can be formulated with a carrier that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are known in the art. See, e.g., J. R. Robinson (1978) "Sustained and Controlled Release Drug Delivery Systems," Marcel Dekker, Inc., New York.

In some embodiments, compositions can be formulated in a composition suitable for intrapulmonary administration (e.g., for administration via an inhaler or nebulizer) to a mammal such as a human. Methods for formulating such compositions are well known in the art and described in, e.g., U.S. Patent Application Publication No. 20080202513; U.S. Pat. Nos. 7,112,341 and 6,019,968; and PCT Publication Nos. WO 00/061178 and WO 06/122257, the disclosures of each of which are incorporated herein by reference in their entirety. Dry powder inhaler formulations and suitable systems for administration of the formulations are described in, e.g., U.S. Patent Application Publication No. 20070235029, PCT Publication No. WO 00/69887; and U.S. Pat. No. 5,997,848. Additional formulations suitable for intrapulmonary administration (as well as methods for formulating polypeptides) are set forth in, e.g., U.S. Patent Application Publication Nos. 20050271660 and 20090110679.

In some embodiments, compositions can be administered locally, for example, by way of topical application or intravitreal injection. For example, in some embodiments, the compositions can be formulated for administration by way of an eye drop.

Nucleic acids encoding a therapeutic polypeptide can be incorporated into a gene construct to be used as a part of a gene therapy protocol to deliver nucleic acids that can be used to express and produce agents within cells. Expression constructs of such components may be administered in any therapeutically effective carrier, e.g. any formulation or composition capable of effectively delivering the component gene to cells in vivo. Approaches include insertion of the subject gene in viral vectors including recombinant retroviruses, adenovirus, adeno-associated virus, lentivirus, and herpes simplex virus-1 (HSV-1), or recombinant bacterial or eukaryotic plasmids. Viral vectors can transfect cells directly; plasmid DNA can be delivered with the help of, for example, cationic liposomes (lipofectin) or derivatized, polylysine conjugates, gramicidin S, artificial viral envelopes or other such intracellular carriers, as well as direct injection of the gene construct or $CaPO_4$ precipitation (see, e.g., WO04/060407) carried out in vivo. Examples of suitable retroviruses include pLJ, pZIP, pWE and pEM which are known to those skilled in the art (see, e.g., Eglitis et al. (1985) *Science* 230:1395-1398; Danos and Mulligan (1988) *Proc Natl Acad Sci USA* 85:6460-6464; Wilson et al. (1988) *Proc Natl Acad Sci USA* 85:3014-3018; Armentano et al. (1990) *Proc Natl Acad Sci USA* 87:6141-6145; Huber et al. (1991) *Proc Natl Acad Sci USA* 88:8039-8043; Ferry et al. (1991) *Proc Natl Acad Sci USA* 88:8377-8381; Chowdhury et al. (1991) *Science* 254:1802-1805; van Beusechem et al. (1992) *Proc Natl Acad Sci USA* 89:7640-7644; Kay et al. (1992) *Human Gene Therapy* 3:641-647; Dai et al. (1992) *Proc Natl Acad Sci USA* 89:10892-10895; Hwu et al. (1993) *J Immunol* 150:4104-4115; U.S. Pat. Nos. 4,868,116 and 4,980,286; and PCT Publication Nos. WO89/07136, WO89/02468, WO89/05345, and WO92/07573). Another viral gene delivery system utilizes adenovirus-derived vectors (see, e.g., Berkner et al. (1988) *BioTechniques* 6:616; Rosenfeld et al. (1991) *Science* 252:431-434; and Rosenfeld et al. (1992) *Cell* 68:143-155). Suitable adenoviral vectors derived from the adenovirus strain Ad type 5 dl324 or other strains of adenovirus (e.g., Ad2, Ad3, Ad7, etc.) are known to those skilled in the art. Yet another viral vector system useful for delivery of the subject gene is the adeno-associated virus (AAV). See, e.g., Flotte et al. (1992) *Am J Respir Cell Mol Biol* 7:349-356; Samulski et al. (1989) *J Virol* 63:3822-3828; and McLaughlin et al. (1989) *J Virol* 62:1963-1973.

In some embodiments, compositions can be formulated for administration to a subject or, if administered to a fetus, to a female carrying such fetus, along with intravenous gamma globulin therapy (IVIG), plasmapheresis, plasma replacement, or plasma exchange.

The compositions of the present invention may be administered and dosed in accordance with current medical practice, taking into account the clinical condition of the subject, the site and method of administration, the scheduling of administration, the subject's age, sex, body weight and other factors relevant to clinicians of ordinary skill in the art. The "effective amount" for the purposes herein may be determined by such relevant considerations as are known to those of ordinary skill in experimental clinical research, pharmacological, clinical and medical arts. In some embodiments, the amount administered is effective to achieve at least some stabilization, improvement or elimination of symptoms and other indicators as are selected as appropriate measures of disease progress, regression or improvement by those of skill in the art. For example, a suitable amount and dosing regimen is one that causes at least transient expression of the nucleic acid in the target cell.

Any amount of a pharmaceutical composition containing an isolated alkaline phosphatase polypeptide or nucleic acid molecule encoding alkaline phosphatase can be administered to a subject. Typically, the amount of alkaline phosphatase contained within a single dose will be an amount that effectively prevents, delays or corrects bone mineralization defects in a subject having or likely to develop craniosynostosis without inducing significant toxicity. Typically, a alkaline phosphatase in accordance with the present invention can be administered to subjects in doses ranging from 0.001 to 500 mg/kg/day and, in a more specific embodiment, about 0.1 to about 100 mg/kg/day, and, in a more specific embodiment, about 0.2 to about 20 mg/kg/day. Typically, a pharmaceutical composition of the invention can be administered in an amount from about 0.001 mg up to about 500 mg per kg of body weight per day (e.g., 0.05, 0.01, 0.1, 0.2, 0.3, 0.5, 0.7, 0.8, 1 mg, 2 mg, 3 mg, 4mg, 5 mg, 10 mg, 15 mg, 20 mg, 30 mg, 50 mg, 100 mg, or 250 mg). Dosages may be provided in either a single or multiple dosage regimens. For example, in some embodiments the effective amount is a dose that ranges from about 0.1 to about 100 mg/kg/day, from about 0.2 mg to about 20 mg of alkaline phosphatase per day, about 1 mg to about 10 mg of alkaline phosphatase per day, from about 0.07 mg to about 210 mg of alkaline phosphatase per week, 1.4 mg to about 140 mg of alkaline phosphatase per week, about 0.3 mg to about 300 mg of alkaline phosphatase every three days, about 0.4 mg to about 40 mg of alkaline phosphatase every other day, and about 2 mg to about 20 mg of alkaline phosphatase every other day.

When compositions are to be used in combination with a second active agent, the compositions can be coformulated with the second agent or the compositions can be formulated separately from the second agent formulation. For example, the respective pharmaceutical compositions can be mixed, e.g., just prior to administration, and administered together or can be administered separately, e.g., at the same or different times.

The route of delivery used in the methods of the invention allows for noninvasive, self-administration of the therapeutic compositions of the invention. The methods of the invention involve intratracheal or pulmonary administration by aerosolization, nebulization, or instillation of the compositions as described above.

EXPERIMENTAL

The following examples are provided in order to demonstrate and further illustrate certain preferred embodiments and aspects of the present invention and are not to be construed as limiting the scope thereof.

EXAMPLE 1

Materials and Methods

Animals

Preparation and genotyping of Alpl+/− mice were previously reported (Fedde et al., J Bone Miner Res 1999; 14(12):2015-26; Narisawa et al., Dev Dyn 1997; 208:432-446). Alpl−/− and wild type (Alpl+/+) mice were obtained by heterozygous breeding. All animals (breeders, nursing mothers and their pups, and weanlings) in this study were given free access to modified laboratory rodent diet 5001 containing increased levels (325 ppm) of pyridoxine. The Alpl−/− mice are maintained in a 12.5% C57B1/6-87.5% 129J background. This mixed genetic background allows one to investigate HPP in a mouse model that better represents phenotype severity and incidence in the human population. Homozygous mice are identified at birth (day 0) by the lack of enzyme activity, compared to about half of the WT activity in heterozygote Alpl+/− mice. One half μl whole blood obtained at the time of toe clipping was used to measure serum ALP activity in a total reaction volume of 25 μL, velocity of 30 min at OD 405, with 10 mM pnitrophenolphosphate (pNPP) (Millan et al, J Bone Miner Res 2008; 23:777-87). The genotype of the animals was confirmed by PCR using tail DNA obtained at the time of tissue collection as previously described (Yadav et al., Bone 2011; 49(2): 250-6). All animal procedures were approved by the Sanford-Burnham Animal Care and Use Committee (La Jolla, Calif., USA).

Linear Craniofacial Measurements

The craniofacial bones of Alpl−/− mice are present but severely under-mineralized, making visualization of some skeletal landmarks difficult on micro-computed tomographic images. Therefore, digital calipers were utilized to conduct craniofacial linear measurements. P15 Alpl−/− (n=24), P15 Alpl+/+ (n=24), P20 Alpl−/− (n=37) and P20 Alpl+/+ (n=39) mouse skulls were carefully dissected and fixed. P15 refers to day 15 mice and P20 refers to day 20 mice. Linear measurements were calculated using previously reported skeletal landmarks (Perlyn et al., Cleft Palate Craniofac J 2006; 43(6):740-8; Liu et al., Calc Tissue Int 2013; 92(5): 451-466), including five standard measurements currently in use by the Craniofacial Mutant Mouse Resource of the Jackson Laboratory (Bar Harbor, Me.), which are skull length (nasale to paro), skull width (measured between right and left intersections between the squamosal body to the zygomatic process of the squamous portion of the temporal bone), inner canthal distance (measured between right and left intersections of frontal process of maxilla with frontal and lacrimal bones), nose length (nasale to bregma) and nasal bone length (measured from nasale to nasion). The Jackson Laboratory skull height measurement was substituted with a cranial height measurement taken between pari and the inferior portion of the spheno-occipital synchondrosis, due to the omission of the mandible in our study. Linear measurements were also calculated for frontal bone length (nasion to bregma) and parietal bone length (bregma to pari). Linear distances of bilateral structures were averaged from right and left measurements for each mouse. Measurements were performed twice and an average of the two measurements was utilized for statistical comparison of genotypes. Because the overall size of Alpl−/− mice is smaller than Alpl+/+ mice (all craniofacial linear measurements were smaller in TNAP−/− mice), linear measurements were normalized to total skull length (measured from nasale to opisthion). No significant difference between genders was found therefore genders were combined for comparison of genotypes. Data is presented as means +/− standard deviations. Statistical significance was established by the student's t test.

Micro-Computed Tomography

Whole dissected calvaria from P15 Alpl−/− (n=24), P15 Alpl+/+ (n=24), P20 Alpl−/− (n=37) and P20 Alpl+/+ (n=39) were fixed then scanned in water at an 18 μm isotropic voxel resolution using the eXplore Locus SP micro-computed tomography imaging system (GE Healthcare Pre-Clinical Imaging, London, ON, Canada). Measurements were taken at an operating voltage of 80 kV and 80 mA of current, with an exposure time of 1600 ms using the Parker method scan technique, which rotates the sample 180 degrees plus a fan angle of 20 degrees. Scans were calibrated to a hydroxyapatite phantom and 3D images were reconstructed at an effective voxel size of 18 μm3. A fixed threshold of 1400 Hounsfield Units was used to discriminate mineralized tissue. Regions of interest (ROI's) for parietal and frontal bones were established as 1 mm in length, 1 mm in width, depth equivalent to thickness of bone and position starting at a 0.75 mm distance from sagittal and coronal sutures, using the Advanced ROI tool. The ROI tool was also utilized to isolate bones of the cranial base for analysis. Bone volume fraction, bone mineral density, bone mineral content, tissue mineral density and tissue mineral content were measured using Microview version 2.2 software (GE Healthcare Pre-Clinical Imaging, London, ON) and established algorithms (Meganck et al., Bone 2009; 45(6):1104-1116; Umoh et al., Phys Med Biol 2009; 54(7):2147-61). Student's t-tests comparing quantitative results were performed to establish statistically significant differences between genotypes. Micro-CT bone data was analyzed and is reported in accordance with the recommendations of Bouxsein et al. 2010 (J Bone Miner Res 2010; 25(7):1468-86).

Craniosynostosis Assessment

Fusion of the coronal suture (fusion between frontal and parietal bones), lambdoid suture (fusion between parietal and occipital bones) and sagittal suture (fusion between the right and left parietal bones) was initially assessed using the micro-CT scans of Alpl−/− and Alpl+/+ dissected calvaria. Cranial sutures were viewed using the two-dimensional micro-CT slices in an orthogonal view across the entire length of the coronal suture, as previously described (Perlyn tet al., supra; Liu et al., supra). Bone fusion assessments from micro-CT images were verified by visualization of all specimens under a dissecting microscope (Leica M60 TL5000; Leica Microsystems Inc., Buffalo Groves, Ill.). No significant difference between genders was found; therefore genders were combined for comparison of genotypes. Fisher's exact test based upon the number of fused versus patent sutures was performed to establish statistical significance between genotypes.

Histology

Dissected and fixed skulls were serially dehydrated, washed in isopropanol, incubated in xylene and embedded in methyl methacrylate. Methacrylate blocks were trimmed in the sagittal plane to within 2 mm of the sagittal suture. 4 uM sections perpendicular to the coronal suture were prepared with a Leica RM2255 microtome equipped with a tungsten carbide blade (Leica Microsystems Inc., Buffalo Groves, Ill.). Sections were transferred to slides and dried at 42° C. in a slide press overnight. Sections were stained by Von Kossa with toluidine blue by incubation in 5% AgNO3 followed by staining in a 1% toludine blue 1% sodium borate solution.

Establishment of TNAP Deficient Cells

MC3T3E1(C4) pre-osteoblastic cranial cells were transduced with lentiviral particles expressing a puromycin resistance gene and TNAP specific shRNA (Sigma Mission) or non-target shRNA (Sigma Mission, SHC002V) in the presence of 8 ug/ml hexadimethrine bromide. Puromycin resistant colonies were expanded and tested for expression of TNAP.

Cell Culture and Assay

Cells were passaged in custom formulated MEM containing no ascorbate, supplemented with 10% fetal bovine serum (FBS) and penicillin/streptomycin (P/S). Cells were differentiated by media supplementation with 50 ug/ml ascorbate. To induce mineralization, cells were grown for five days in αMEM containing 50 ug/ml ascorbate followed by supplementation with 2.5 mM NaPO4 or 5 mM β-glycerophosphate. For Von Kossa staining, cells were fixed with ethanol and rehydrated in a graded ethanol series. Cells were then rinsed with dH2O, incubated in 5% $AgNO_3$, rinsed again with dH2O, and exposed to light. Tissue non-specific alkaline phosphatase (TNAP) enzyme activity was assayed using the colorimetric substrate, NBT/BCIP (Sigma). For collagenous matrix staining, cells were fixed in Bouin's fixative, washed, air-dried and then incubated with Sirius Red followed by rinsing with 0.01 N HCl. For quantification of mineral, TNAP enzyme activity and Sirius Red staining; wells were scanned and densitometry was performed using NIH Image software. To assay cellular apoptosis, a Cell Death Detection kit (Roche) was utilized according to the manufacturer's instructions. This assay uses antibodies directed against DNA and histones, to quantify mono- and oligonucleosomes that are released into the cytoplasm of cells that die from apoptosis. Briefly, 10,000 cells were seeded into 96-well plates and grown in media containing 10% or 0.5% FBS for 48 hours. Cell lysate was utilized to quantify apoptosis by a colorimetric reaction and absorbance was measured at 405 nm (reference wavelength of 490 nm). To assay cellular proliferation, cells were seeded and grown in media containing 10% FBS. Cells were stained with trypan blue and counted for each time point. Type I collagen coated plates were commercially obtained (Greiner Bio-One). RNA was isolated using Trizol reagent (Invitrogen) following manufacturer protocols. mRNA levels were assayed by reverse transcription and real time PCR. Real time PCR was performed utilizing the murine GAPDH primer/probe set Mm9999915_g1, the murine osteocalcin (OCN) Mm03413826_mH primer/probe set, the murine bone sialoprotein (BSP) primer/probe set Mm00492555_m1, the murine tissue non-specific alkaline phosphatase (TNAP) primer/probe set Mm00475834_m1, the murine osteopontin (OPN) primer/probe set Mm01204014_m1, the murine collagen type 1, alpha 1 (Col1a1) primer/probe set Mm00801666_g1, the murine Runx2 primer/probe set Mm00501578_m1 and Taqman Universal PCR Master Mix (Applied Biosystems). Real-time PCR was performed on a GeneAmp 7700 thermocyler (Applied Biosystems) and quantified by comparison to a standard curve.

Results

Qualitative Assessment of Overall Craniofacial Phenotype in Alpl−/− Mice

Micro-CT isosurface images of P15 and P20 Alpl−/− mouse skulls (FIG. 1C,D,G,H) reveal an obvious craniofacial phenotype involving abnormal tissue mineralization and an abnormal craniofacial shape when compared to wild-type littermates (FIG. 1A,B,E,F). Multiple bones of the cranial vault and face including the squamosal, temporal, frontal, maxillary and zygomatic bones are so severely under-mineralized in Alpl−/− mice that they in part or whole do not appear on micro-CT scans that were calibrated to a hydroxyapatite phantom and constrained to a bone tissue threshold. Parietal, interparietal, occipital, sphenoid and posterior frontal bones in contrast, appear relatively less affected in the Alpl−/− skull. These findings suggest the presence of severe osteomalacia that is bone specific. Notably, while there does appear to be some increase in mineralization of parietal and frontal bones in the P20 Alpl−/− skull as compared to the P15 Alpl−/− skull, bones that are not mineralized in the P15 Alpl−/− skull are also not mineralized in the P20 Alpl−/− skull. In addition to the mineralization abnormalities, the overall shape of the Alpl−/− skull appears different than that of the Alpl+/+ skull. The Alpl−/− skull appears shorter in length and taller in height, leading to an overall dome shaped appearance, when compared to that of the Alpl+/+ skull. These shape abnormalities are apparent in both P15 and P20 Alpl−/− mice, indicating that the shape abnormalities are present by two weeks after birth.

Craniofacial Skeletal Linear Analysis

Figure 2:
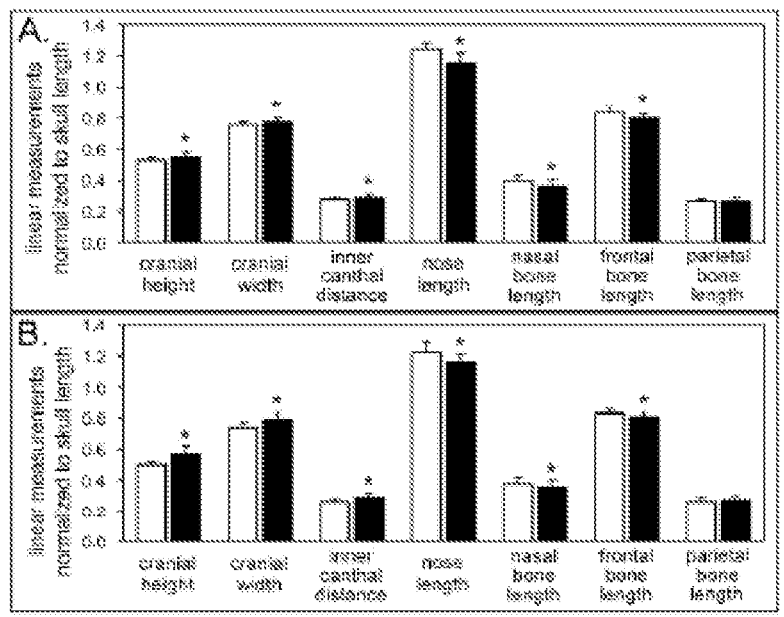
FIGS. 2A and 2B are graphs showing that linear analysis of craniofacial forms demonstrates craniofacial shape abnormalities in Alpl−/− mice. Linear measurements demonstrate significantly increased cranial height, cranial width and inner canthal distance, with significantly diminished nose, nasal bone and frontal bone lengths in both P15 (A) and P20 (B) Alpl−/− mice, as compared to Alpl+/+ mice. Parietal bone length is not different between Alpl−/− and Alpl+/+ mice at either age. *p<0.05 vs. Alpl+/+. White=Alpl+/+, black=Alpl−/−.

To quantify form abnormalities (form includes differences in size and shape) in the craniofacial skeleton of Alpl−/− mice, linear data generated from digital caliper measurements of Alpl−/− and Alpl+/+ skulls was utilized. These measurements demonstrate that the craniofacial form of Alpl−/− mice is consistently different than that of Alpl+/+ mice as early as two weeks after birth, in that multiple linear measurements are statistically different between P15 Alpl−/− and Alpl+/+ mice. Similar differences are seen between between P20 Alpl−/− and Alpl+/+ mice. When normalized to skull length, cranial height, cranial width, and inner canthal distance are longer; while nose length, nasal bone and frontal bone length are shorter in P15 Alpl−/− mice when compared to Alpl+/+ mice (FIG. 2A). Parietal bones are not different in Alpl−/− and Alpl+/+ mice. Similar results are seen for P20 Alpl−/− skulls (FIG. 2B).

Together these results support the assessment of the Alpl−/− skull as being different in form from that of Alpl+/+ mice. Because measurements that are normalized for skull size, these results also indicate that Alpl−/− P15 and P20 skulls are different in shape from those of Alpl+/+ mice. Overall the skulls of Alpl−/− mice appear acrocephalic and dome shaped, similar to that which has been reported in infants with HPP (Fraser, Am J Med 1957; 22(5):730-46; Collmann et al., Childs Nerv Syst 2009; 25(2):217-23).

Micro-CT Based Assessments of Craniofacial Bone Volume, Density and Mineral Content Previous reports demonstrated that the long bones of Alpl−/− mice are significantly diminished in mineral content when compared to those of WT mice when assessed by alizarin stain and micro-CT, which accurately reflects the long bone osteomalacia seen in HPP patients (Narisawa et al., Dev Dyn 1997; 208:432-446; Anderson et al., Am J Pathol 2005; 166:1711-1720). To determine the extent to which mineralization of the craniofacial skeleton is affected in Alpl−/− mice, micro-CT based analyses of bone volume, density and mineral content was performed on calvarial and cranial base bones of Alpl−/− mice and wild type littermates. Because isosurface images based upon the micro-CT scans (FIG. 1) showed diminished craniofacial bone mineralization that appeared more severe in frontal than parietal bones, and because it was suspected based upon the overall skull shape that these two bones could be involved in fusions, bone parameters were quantified for these two bones. Results (Table 1) show that normalized micro-CT based parameters of P15 Alpl−/− frontal and parietal bones (bone volume fraction, bone mineral density and tissue mineral density) are not significantly different from those of P15 Alpl+/+ frontal and parietal bones, indicating that mineralization of these bones is not significantly affected by a lack of TNAP enzyme by two weeks post-birth. In contrast, bone volume fraction, bone mineral density and tissue mineral density of P20 Alpl−/− frontal and parietal bones are significantly lower than that seen in P20 Alpl+/+ frontal and parietal bones, indicating that TNAP deficiency leads to significant osteomalacia of these calvarial bones by approximately three weeks after birth. Bone volume fraction, bone mineral density and tissue mineral density not significantly greater in frontal bones of P20 Alpl−/− mice than those of P15 Alpl−/− mice, indicating that bone mineralization is not progressing in this bone as the mice continue to grow. Bone volume fraction, bone mineral density and tissue mineral density are significantly greater in parietal bones of P20 Alpl−/− mice than those of P15 Alpl−/− mice, indicating that bone mineralization is occurring in this bone as the mice continue to grow, albeit to a lesser extent as that seen in wild type mice. Together, these findings demonstrate that the Alpl−/− mouse exhibits progressive osteomalacia of calvarial bones, similar to that seen in the craniofacial and long bones of Alpl−/− mice (Fedde et al., J Bone Miner Res 1999; 14(12):2015-26; Narisawa et al., Dev Dyn 1997; 208:432-446) and HPP patients (Mornet Orphanet J Rare Dis 2007; 2:40; Whyte Ann N Y Acad Sci 2010; 1192:190-200; OnlineMendelian Inheritance in Man).

Micro-CT analysis of P15 Alpl−/− cranial base bones shows significantly diminished tissue mineral density in P15 Alpl−/− mice, indicating that, in contrast to the calvarial bones, mineralization of cranial base bones is significantly affected by a lack of TNAP enzyme by approximately two weeks post-birth. Bone volume fraction, bone mineral density and tissue mineral density are significantly lower in P20 Alpl−/− cranial base bones than in P20 Alpl+/+ cranial base bones, indicating that osteomalacia of these bones is also present at three weeks after birth. Bone volume fraction and bone mineral density decreased significantly from fifteen to twenty days after birth in Alpl−/− cranial base bones. These results are again consistent with the progressive clinical course osteomalcia typically seen in infantile hypophosphatasia.

Craniosynostosis Assessment

Figure 3:
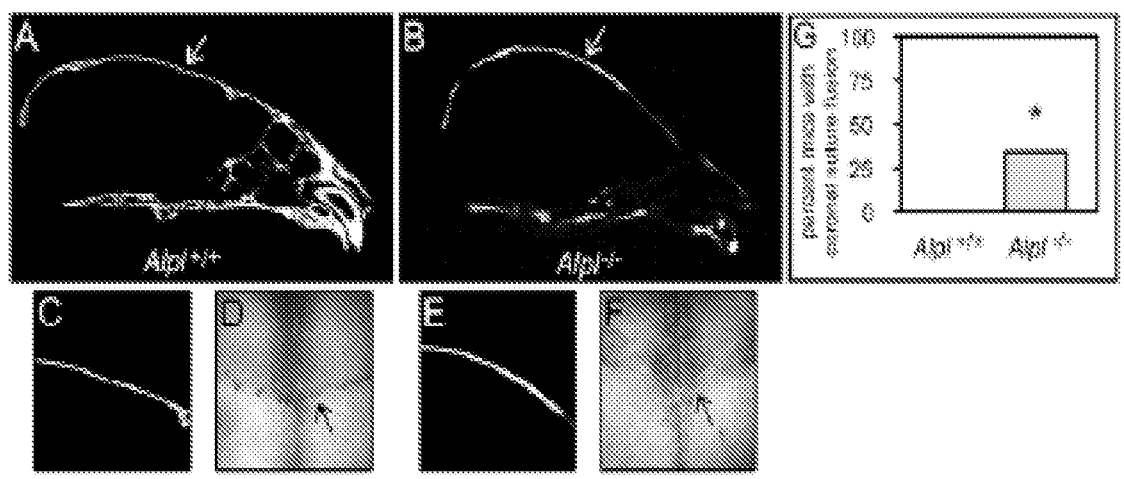
FIGS. 3A-3F are micro CT images showing craniosynostosis in Alpl−/− mice. Coronal suture fusion assessment in 20-day-old mice. Representative micro CT images show fusion of the coronal suture in Alpl−/− (B) but not in Alpl+/+ (A) skulls (white arrows point to open coronal suture in wild type and fused coronal suture in mutant). Magnification of coronal suture and bone surrounding the coronal suture in Alpl+/+ (C) and Alpl−/− (E) mice. 32× Magnification of dissected skulls also demonstrates loss of patency of the coronal future near the sagittal midline in Alpl−/− (F) mice but not Alpl+/+ (D) mice (black arrows point to patent coronal suture in Alpl+/+ mice and fused coronal suture in Alpl−/− mice). No P20 mice exhibited fusion of the sagittal or lambdoid sutures, regardless of genotype.
FIG. 3G is a graph showing statistical comparison of the incidence of coronal suture fusion in Alpl+/+ and Alpl−/− mice demonstrates that a significant number of Alpl−/− mice exhibit craniosynostosis in the form of coronal suture fusion when compared to Alpl+/+ mice.
Figure 4:
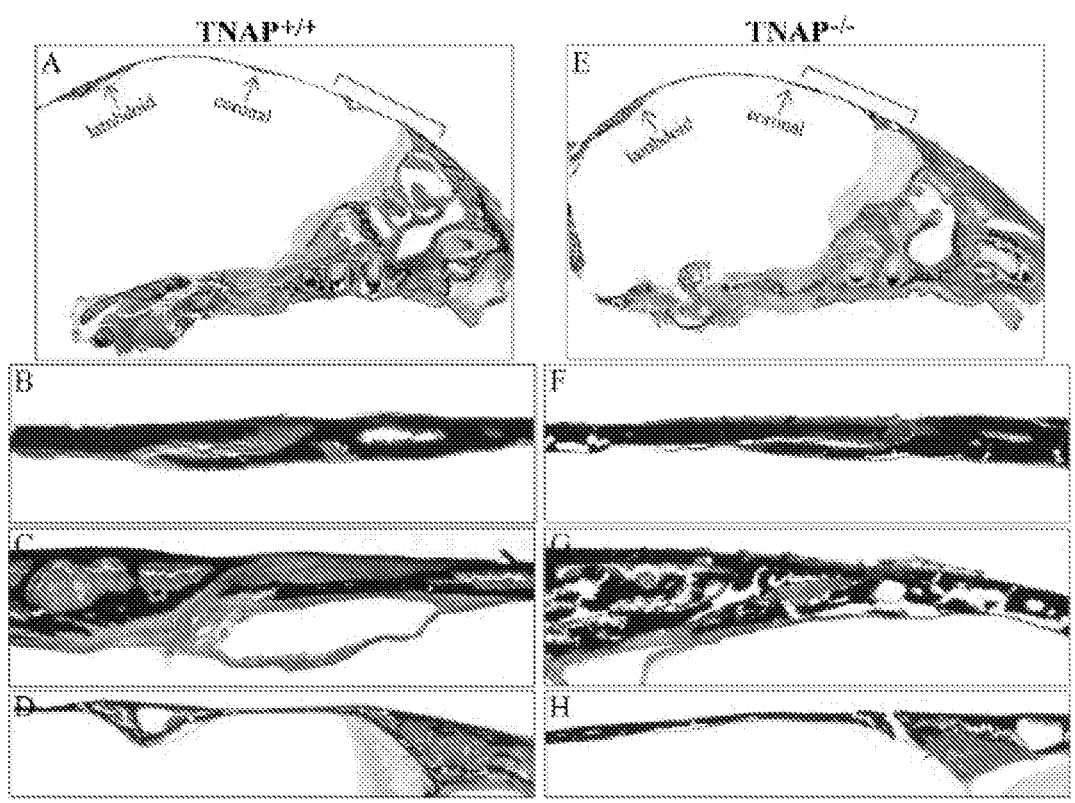
FIGS. 4A-4H are photographs showing histology of P15 calvarial bones and sutures. Histologic staining of non-decalcified sagittal sections of P15 Alpl+/+ (A) and Alpl−/− (E) mouse skulls are shown (black stains mineral). Arrows point to lamdoid and coronal sutures. (B,F) 10× magnification of Alpl+/+ (B) and Alpl−/− (E) coronal suture and surrounding tissues. (C,G) 10× magnification of Alpl+/+ (C) and Alpl−/− (F) lambdoid suture and surrounding tissues. (G,H) 10× magnification of Alpl+/+ (G) and Alpl−/− (H) anterior frontal bone (red bracket shown in A,E). Note the clearly demarcated cortical bone and large arrow spaces in the Alpl+/+ skull (G). In addition to diminished mineralization, the Alpl−/− bone exhibit diminished marrow space (H).
Figure 5:
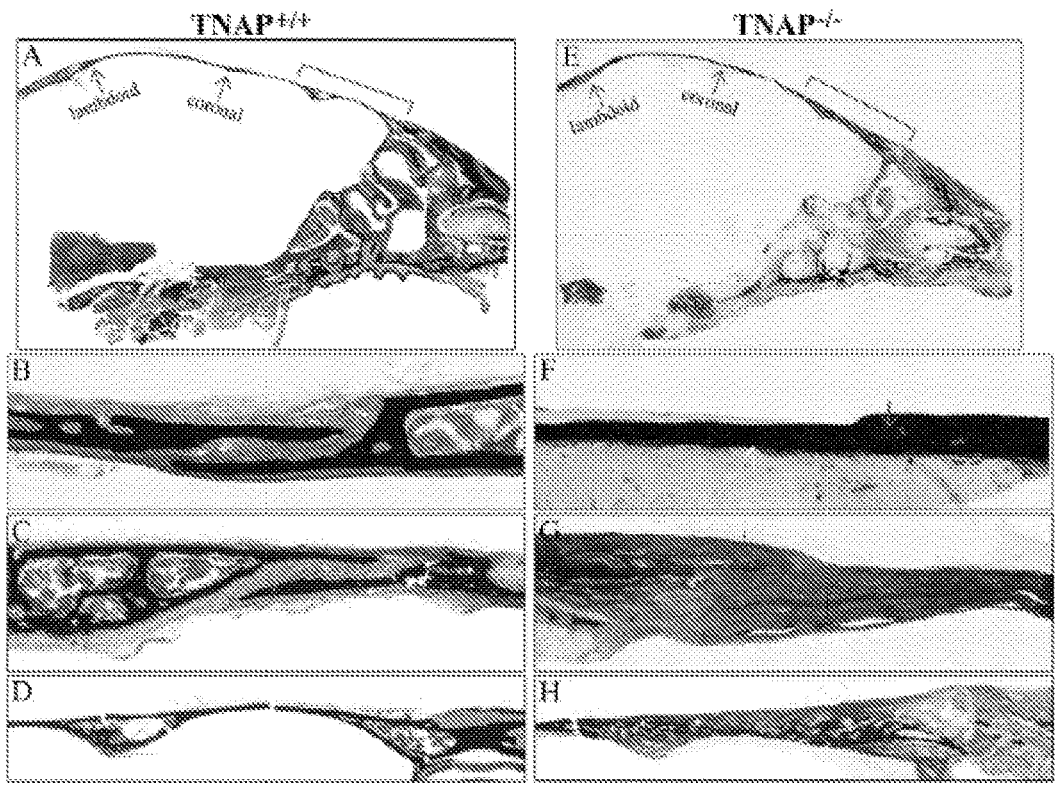
FIGS. 5A-5H are photographs showing histology of P20 calvarial bones and sutures. Histologic staining of non-decalcified sagittal sections of P20 Alpl+/+ (A) and Alpl−/− (E) mouse skulls are shown. Red arrows point to lamdoid and coronal sutures. (B,E) 10× magnification of Alpl+/+ (B) and Alpl−/− (F) coronal suture and surrounding tissues. (C,G) 10× magnification of Alpl+/+ (C) and Alpl−/− (F) lamdoid suture and surrounding tissues. (G,H) 10× magnification of Alpl+/+ (G) and Alpl−/− (H) anterior frontal bone (bracket shown in A,D). Cortical bone ad marrow spaces in the Alpl+/+ skull (G). In addition to diminished mineralization, the Alpl−/− bone lacks distinct cortex, trabeculae and decreased marrow space (H).

Any degree of craniosynostosis will prevent growth of involved cranial bones along the entire length of the fused suture, because separation of cranial bones is necessary for new bone growth to occur in that area. Isosurface micro-CT images suggested potential bony bridges between frontal and parietal bones of Alpl−/− mice (FIG. 1) and the overall craniofacial shape of Alpl−/− mice is similar to that seen in human patients and mice with coronal suture fusion (fusion between frontal and parietal bones) (Liu et al., Calc Tissue Int 2013; 92(5):451-466; Cohen M M Jr. J Craniofac Surg 2009; 20 Suppl 1:646-51). Fusion vs. patency of the cranial sutures in P20 Alpl−/− and Alpl+/+ mice were assessed using the two-dimensional micro-CT slices in an orthogonal view across the entire length of the coronal suture (Perlyn et al., Cleft Palate Craniofac J 2006; 43(6):740-8; Liu et al., supra). The coronal suture was patent in all Alpl+/+ mice and partially fused in 34% of TNAP−/− mice (FIG. 3). The sagittal and lambdoid sutures were patent in all mice, regardless of genotype. Craniosynostosis was not evident in P15 mice, regardless of genotype. Presence or lack of craniosynostosis was also documented by histology (FIGS. 4, 5).

Histologic Assessment of the Craniofacial Skeleton

To confirm fusion between calvarial bones and to assess the overall effect of TNAP deficiency on craniofacial skeletal development, histologic staining of nondecalcified tissue sections was performed. Von Kossa with toluidine blue staining of P15 and P20 Alpl−/− mice confirms that all craniofacial bones are present and that many bones have large regions lacking mineralization (FIGS. 4, 5). Additionally, while calvarial and facial bones of Alpl+/+ mice appear well-defined with clearly establish cortices, trabeculae and marrow; many Alpl−/− calvarial and facial bones appear thickened, with disorganized bone morphology including no clear distinction between cortical and trabecular bone, and diminished or absent marrow spaces. The coronal suture appears normally patent in both P15 and P20 Alpl+/+ mice. The coronal suture is also patent in P15 Alpl−/− mice, although diminished in width when compared to that of P15 Alpl+/+ mice (FIG. 4B,F). In P20 Alpl−/− mice, while some suture tissue is present, parietal and frontal bones are fused along the inferior aspect of the coronal suture (FIG. 5 B,F). The lambdoid suture is patent in both P15 and P20 Alpl−/− and Alpl+/+ mice although lamdoid suture width is diminished in both P15 and P20 Alpl−/− mice (FIG. 4C,G; FIG. 5C,G). Thickened and hypomineralized bone matrix is present in bones surrounding the lambdoid suture in P20 Alpl−/− mice.

The anterior frontal bone also exhibits thickening and hypomineralization with diminished marrow space that is worse in P20 than P15 in Alpl−/− mice (FIG. 4D,H; FIG. 5D,H). Because calvarial and facial bones are intramembraneous, these results indicatet that TNAP is essential for normal bone mineralization and morphology by calvarial osteoblasts. These results also demonstrate that craniosynostosis does not appear in Alpl−/− mice until approximately three weeks after birth.

Figure 6:
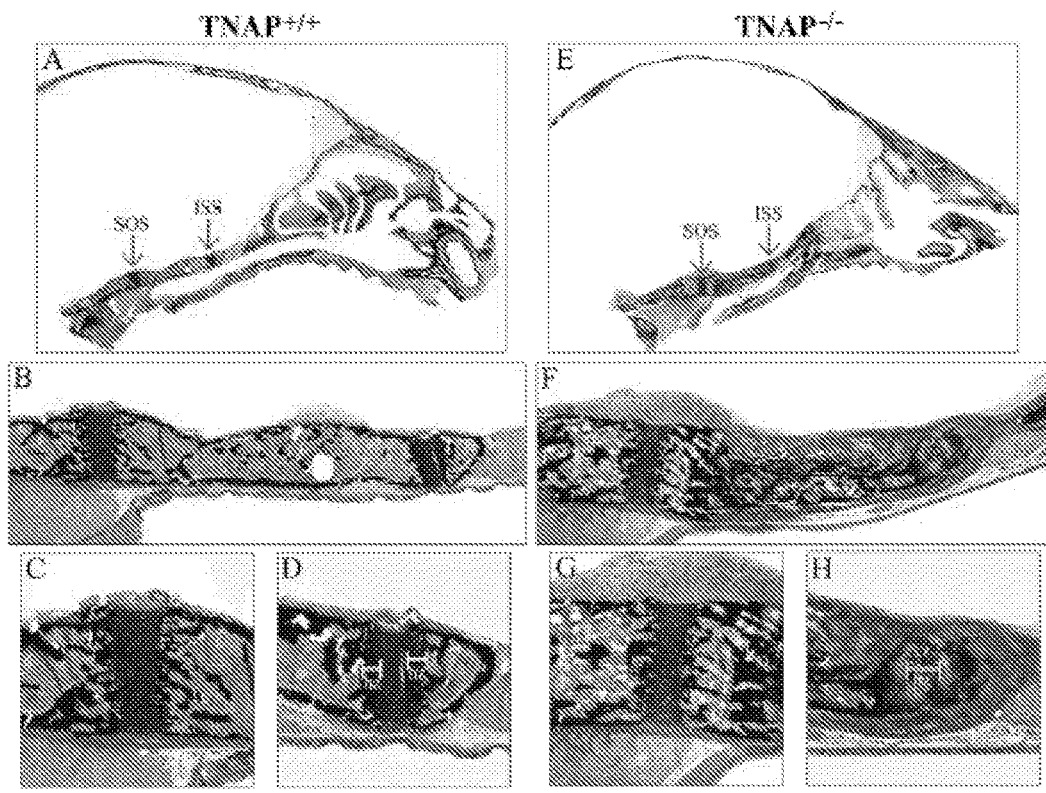
FIGS. 6A-6H are photographs showing histology of P15 cranial base bones and synchondroses. Histologic staining of nondecalcified mid-sagittal sections of P15 Alpl+/+ (A) and Alpl−/− (E) mouse skulls are shown (black stains mineral). Red arrows point to spheno-occipital (SOS) and inter-sphenoidal (ISS) synchondroses. (B,F) 10× magnification of Alpl+/+ (B) and Alpl−/− (F) the cranial base including SOS and ISS. (C,D,G,H) 40× magnification of Alpl+/+ SOS (C), Alpl+/+ ISS (D), Alpl−/− SOS (G) and Alpl−/− ISS (H).
Figure 7:
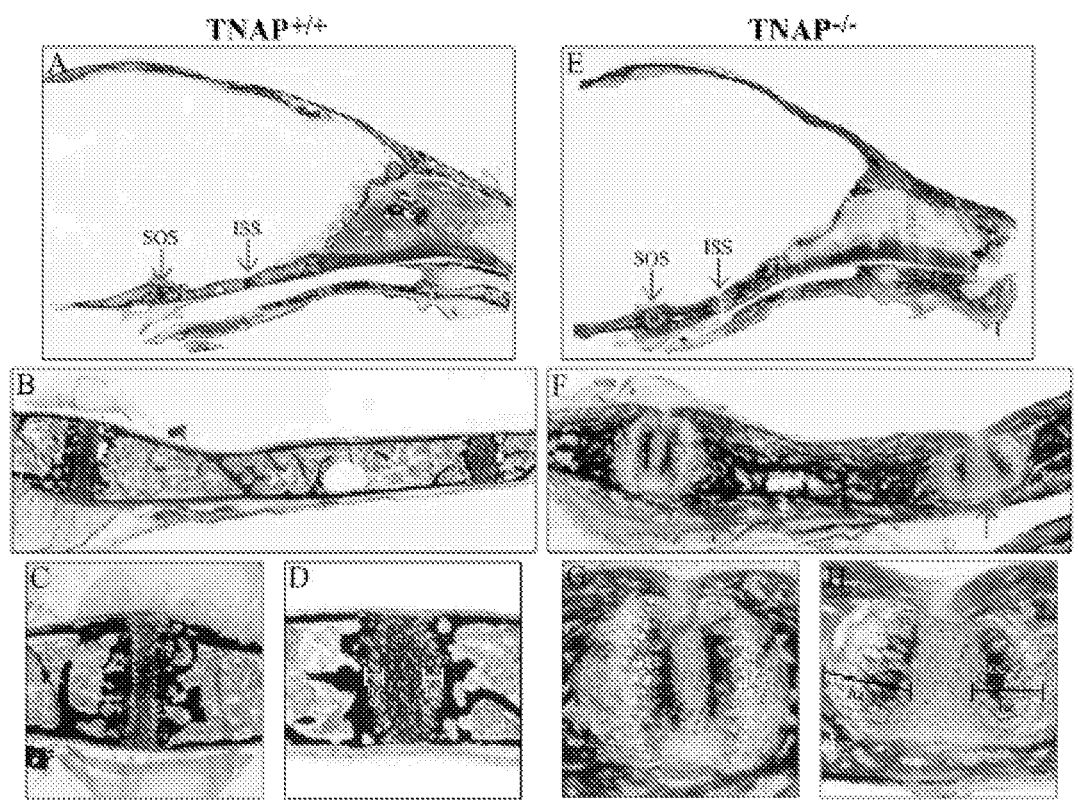
FIGS. 7A-7H are photographs showing histology of P20 cranial base bones and synchondroses. Histologic staining of nondecalcified mid-sagittal sections of P20 Alpl+/+ (A) and Alpl−/− (E) mouse skulls are shown. (B,F) 10× magnification of Alpl+/+ (B) and Alpl−/− (F) the cranial base including SOS and ISS. (C,D,G,H) 40× magnification of Alpl+/+ SOS (C), Alpl+/+ ISS (D), Alpl−/− SOS (G) and Alpl−/− ISS (H).

Because microCT scans showed cranial base abnormalities and because abnormalities in long bone growth plates of Alpl−/− mice were previously reported (Fedde et al., J Bone Miner Res 1999; 14(12):2015-26; Narisawa et al., Dev Dyn 1997; 208:432-446; Yadav et al., Bone 2011; 49(2):250-6), histologic staining of the cranial base was performed. Abnormalities are evident in both cartilaginous and bony aspects of the P15 and P20 Alpl−/− cranial base. In P15 Alpl−/− skulls, the sphenoid exhibits a thick layer of hypomineralized bone matrix present external to the mineralized portion of the diaphysis (FIG. 6F). This tissue appears disorganized; lacking in cortex, trabeculae and marrow spaces. Additionally, while the spheno-occipital synchondrosis (SOS) of P15 Alpl−/− mice appears fairly normal relative to that of P15 Alpl+/+ mice (FIG. 6C,G), the intersphenoidal synchondrosis (ISS) is abnormal, exhibiting a widely expanded single hypertrophic zone (FIG. 6D,H). Mineral is also absent from hypertrophic cell columns in the ISS of P15 Alpl−/− mice. More striking abnormalities are seen in cartilaginous and bony aspects of the P20 Alpl−/− cranial base (FIG. 7). The diaphysis of both the sphenoid and occipital bones appear thickened and disorganized with no clear delineation between cortices and trabeculae (FIG. 7F). Mineral is present within the inner third of bone but does not extend to the outer surface. Marrow space appears diminished. Notably, there is also evidence of non-mineralized bone matrix bridging (fusion) between anterior and posterior aspects of the sphenoid along the inferior aspects of the intersphenoidal synchondrosis (ISS). In addition, the synchondroses themselves are quite abnormal. In contrast to the single secondary ossification center present in the P20 Alpl+/+ SOS and no secondary ossification center present in the P20 Alpl+/+ ISS, both Alpl−/− synchondroses contain two secondary ossification centers and exhibit marked expansion of hypertrophic zones (FIG. 7C,D,G,H). Mineral is absent from the lateral hypertrophic zones in both the SOS and ISS of Alpl−/− mice (does not insert between hypertrophic cell columns). These findings confirm that TNAP is essential for normal endochondral bone growth, including the cranial base. Together, these results also indicate that cranial base abnormalities are apparent within two weeks after birth, and get worse with continued growth in Alpl−/− mice. Because defects in cranial base growth can also lead to the craniofacial shape abnormalities found in lpl−/− mice, these results also indicate that craniofacial shape abnormalities and craniosynostosis occur secondarily to cranial base abnormalities in these mice.

TNAP Deficient Calvarial Cells Exhibit Aberrant Osteoblastic Cell Behavior

Figure 8:
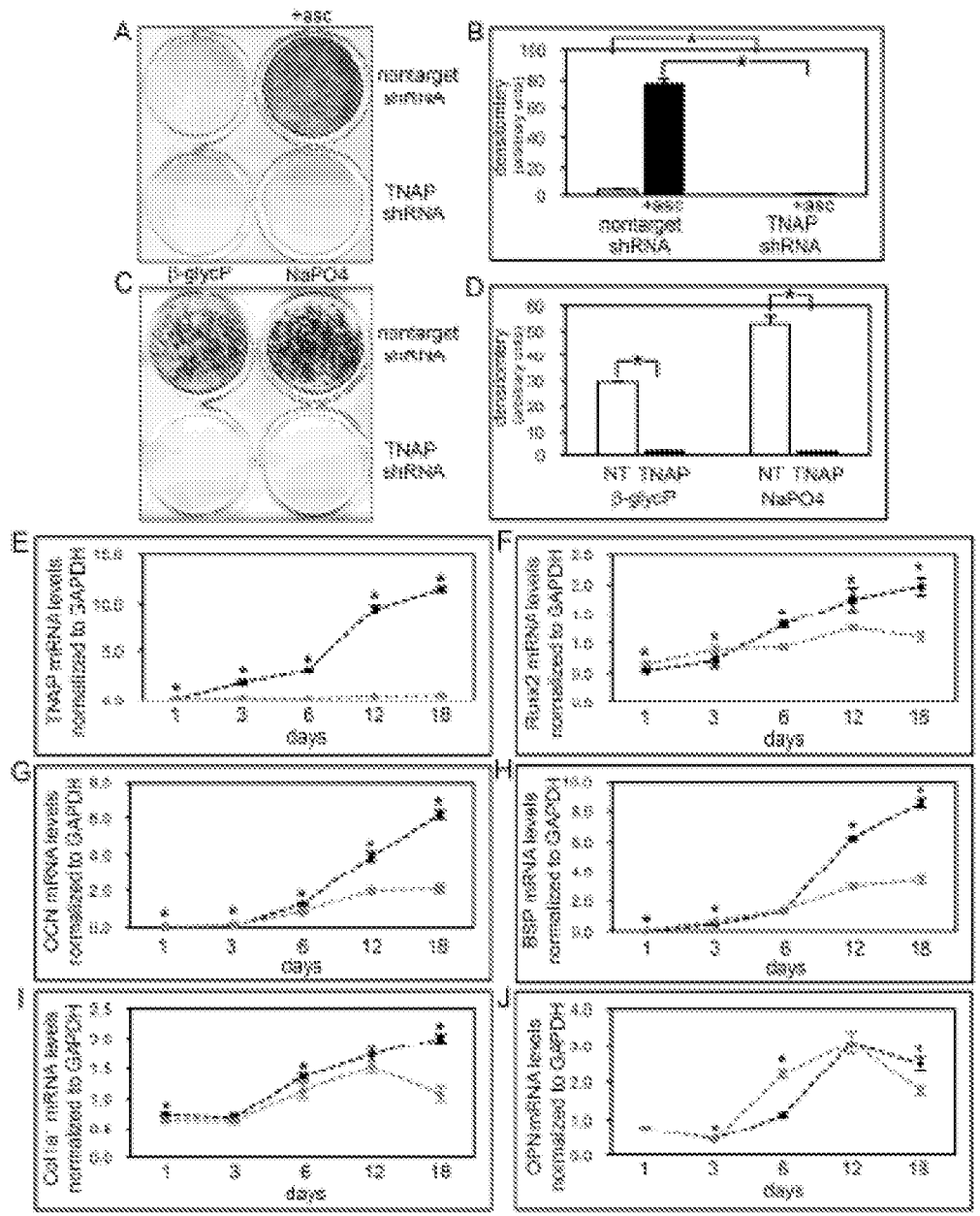
FIGS. 8A-8J show TNAP deficient calvarial cell mineralization and osteoblastic gene expression. (A,B) MC3T3E1 (C4) calvarial cells stably expressing TNAP specific or non-target shRNA were cultured with or without ascorbate to induce osteoblast differentiation. (C,D) Cells were cultured with ascorbate and β-glycerophosphate or NaPO4 to induce mineralized nodule formation. (E-J) Cells were cultured with ascorbate to induce osteoblast differentiation.

Histologic staining of Alpl−/− calvarial bones revealed mineralization and bone morphologic abnormalities (bones lacked clearly defined cortical bone, trabecular bone and marrow), indicating that the influence of TNAP on calvarial cells extends beyond that of promoting hydroxyapatite crystal growth. Therefore, it was next established how TNAP deficiency promotes abnormal calvarial bone development by stably suppressing TNAP expression via shRNA in calvarial MC3T3E1(C4) cells. Results of control experiments confirm that TNAP shRNA expressing cells have extremely low levels of TNAP enzyme activity and mRNA (FIG. 8A,B,E), and that these cells do not form mineralized nodules when provided with either TNAP dependent β-glycerophosphate) or TNAP independent (NaPO4) sources of phosphate for mineralization (FIG. 8C,D). These mineralization results are explained by the fact that TNAP promotes bone mineralization by generating inorganic phosphate, by hydrolyzing the mineralization inhibitor pyrophosphate and by de-phosphorylating the mineralization inhibitor osteopontin (Hessle et al., Proc Natl Acad Sci 2002; 99:9445-9449; Narisawa et al., J Bone Miner Res 2013; 28(7):1587-98; Anderson et al., Am J Pathol 2005; 166:1711-1720; Johnson et al., Am J Physiol Regul Integr Comp Physiol 2000; 279:R1365-1377). A time course of gene expression during osteoblast differentiation in culture shows a different overall pattern of mRNA expression in TNAP shRNA expressing, than non-target shRNA expressing cells (FIG. 8F-J). Runx2 mRNA expression increases upon differentiation in control cells, and this increased expression is maintained for up to 18 days of culture in differentiation media. In contrast, while Runx2 mRNA expression also increases upon differentiation of TNAP shRNA expressing cells, it does so to a lesser extent. Additionally, the higher expression level of Runx2 is not maintained and actually decreases from 12 to 18 days of differentiation in the TNAP shRNA expressing cells. Similarly, while osteocalcin (OCN), bone sialoprotein (BSP) and col1a1 mRNA expression increase in both non-target and TNAP shRNA expressing cells at early differentiation time points, expression increases to a significantly greater extent in non-target than TNAP shRNA expressing cells at later time points of differentiation (col1a1 mRNA expression actually decreases at later time points). Osteopontin (OPN, Sppl) mRNA expression is higher in TNAP shRNA expressing cells at intermediate differentiation time points and is lower in TNAP shRNA expressing cells at later stages of differentiation. Taken together these results indicate that TNAP deficient calvarial cells successfully initiate osteoblastic differentiation but do not sustain it. The results also show that TNAP shRNA expressing cells express significantly higher levels of Runx2, BSP and OCN mRNA days 1 and 3 of differentiation and OPN at days 3 and 6 of differentiation. Overall it was demonstrated that TNAP deficiency alters osteoblastic gene expression, and that the expression of osteoblastic genes may be normal or even enhanced in early and intermediately differentiated TNAP deficient calvarial cells, but this expression becomes diminished with continued differentiation, when compared to control cells.

Figure 9:
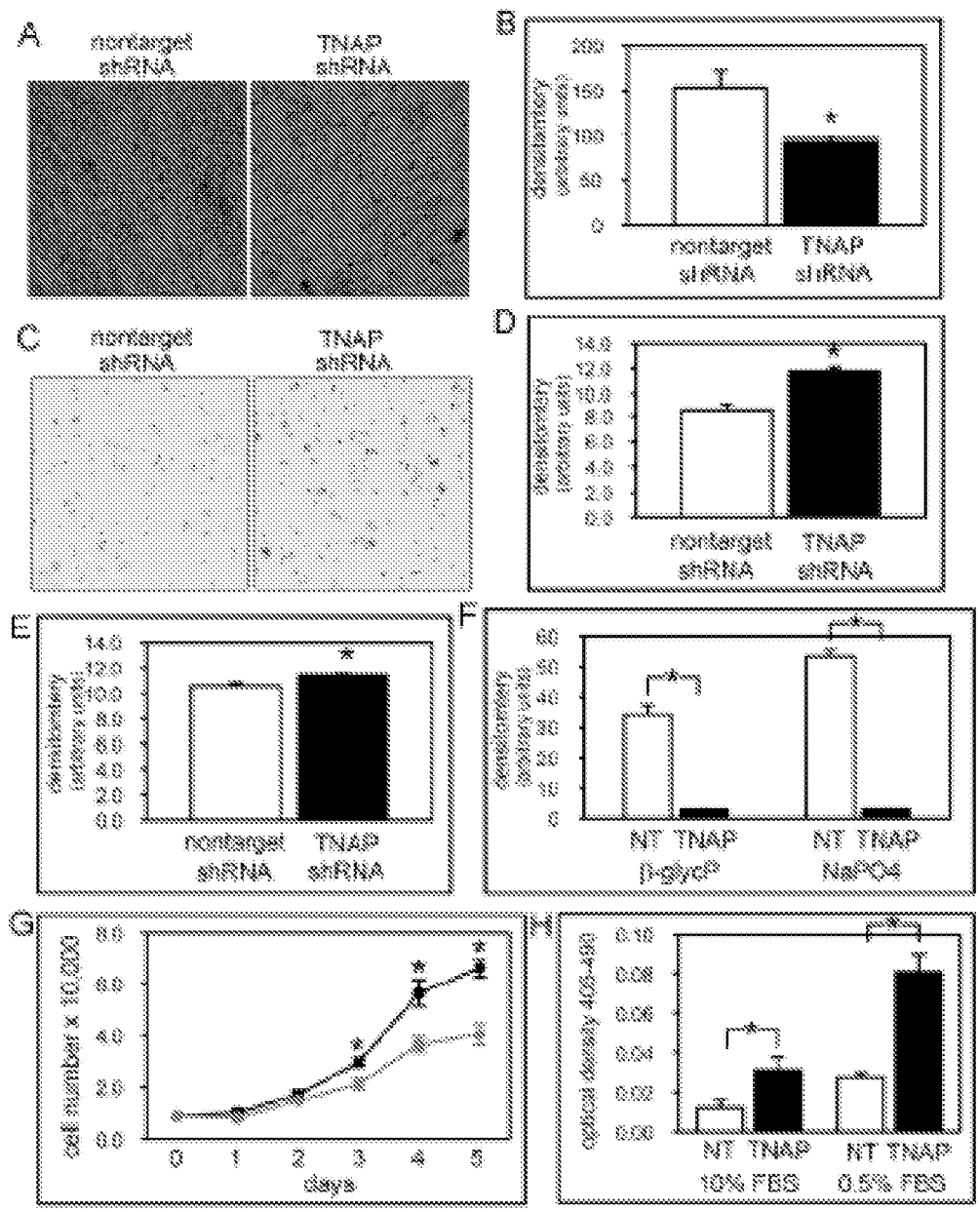
FIGS. 9A-9H show TNAP deficient calvarial cell matrix deposition, adhesion, proliferation and apoptosis. (A,B) Cells were cultured with ascorbate to induce osteoblast differentiation and collagen was stained with Sirius Red. Staining was quantified by densitometry. (C,D) Photograph and quantification of cell adhesion assay. Cell adhesion (E) and mineralization (F) assays were performed on collagen pre-coated plates and quantified. (G) Cells were cultured for up to five days. Cells were stained with trypan blue and counted at indicated time points. (H) Cells were cultured with 10% FBS (fetal bovine serum) or 0.5% FBS to induce apoptosis.

Because col1a1 mRNA expression was diminished in TNAP shRNA expressing cells and because histology of Alpl−/− calvarial bones showed evidence of abnormal matrix deposition (thickening, with a lack of clearly demarcated cortices or marrow spaces), the TNAP and non-target shRNA cells were stained for collagen deposition. Sirius red staining showed ample collagen deposition by both experimental and control cells, yet quantification of the stain revealed diminished collagen deposition by the TNAP shRNA expressing cells (FIG. 9B). Staining also revealed that while the non-target shRNA expressing cells exhibited a well aligned cellular pattern that is typical of differentiating osteoblasts in culture, the TNAP shRNA expressing cells exhibited a more disorganized cellular pattern (FIG. 9A). This latter finding indicated that TNAP shRNA expressing cells were potentially interacting with their matrix in a different manner than control cells. Cell adhesion experiments subsequently showed significantly greater cell adhesion by TNAP shRNA than control cells (FIG. 9C,D). Because TNAP shRNA cells produced less collagen than control cells, cell adhesion on collagen coated plates was assayed. Cell adhesion increased for control cells but did not change for the TNAP shRNA expressing cells on collagen-coated plates, diminishing the likelihood that lower collagen deposition by these cells contributed significantly to their phenotype (FIG. 9E). Mineralization was also assayed on collagen-coated plates and no increase was found in mineral nodule formation by TNAP shRNA expressing cells on these plates (FIG. 9F). TNAP shRNA expressing cells also grew slower than non-target shRNA expressing cells. When quantified, results clearly show diminished proliferation by the TNAP deficient cells (FIG. 9G). Finally, TNAP shRNA expressing cells were tested for their tendency to undergo apoptosis. Results of these experiments demonstrate that a greater percentage of TNAP shRNA expressing cells underwent apoptosis than control cells under normal and lower serum conditions (FIG. 9H). Together these results demonstrate that TNAP deficiency leads to multiple changes in calvarial osteoblastic cell behavior in vitro.

chain reaction using 5'-gagtaccatgctgactgcatgc-3' (SEQ ID NO: 8) and 5'-ggagaggcatctctgtttcaagacc-3' (SEQ ID NO:9) primers. Pups were sacrificed at 4 weeks post-natal for analysis. Blood was collected by aortic puncture under surgical anesthesia. Mice were weighed, and body length was measured from for each animal.

Mineral-Targeted TNAP Lentivirus and Injections

Mineral-targeted TNAP lentivirus was generously provided by Dr. Jose Millán (Burnham Institute for Medical Research, La Jolla, Calif.). This lentivirus expresses a fusion protein containing TNAP enzyme fused at its C-terminal end to a constant region of the human IgG1 Fc domain and to a deca-aspartate sequence. The deca-aspartate sequence confers a positive charge and targets the enzyme to hydroxyapatite, which is negatively charged (Tomatsu et al., Mol

TABLE I

Frontal Bone Volume, Density and Mineral Content in $Alpl^{-/-}$ and $Alpl^{+/+}$ Mice.

| | Bone Volume (mm³) | Bone Volume Fraction | Bone Mineral Content (mg) | Bone Mineral Density (mg/cc) | Tissue Mineral Content (mg) | Tissue Mineral Density (mg/cc) |
|---|---|---|---|---|---|---|
| P15 TNAP$^{-/-}$ frontal | .008 +/- .003* | 0.54 +/- 0.14 | .007 +/- .002* | 478 +/- 43 | .005 +/- .002* | 563 +/- 23 |
| P15 TNAP$^{+/+}$ frontal | .006 +/- .003 | 0.47 +/- 0.18 | .006 +/- .001 | 468 +/- 51 | .004 +/- .002 | 557 +/- 30 |
| P20 TNAP$^{-/-}$ frontal | .008 +/- .005* | 0.54 +/- 0.28 | .007 +/- .003* | 478 +/- 111* | .005 +/- .003* | 588 +/- 34* |
| P20 TNAP$^{+/+}$ frontal | .010 +/- .004 | 0.65 +/- 0.25 | .008 +/- .002 | 538 +/- 77 | .006 +/- .003 | 610 +/- 34 |
| P15 TNAP$^{-/-}$ parietal | .007 +/- .002 | 0.58 +/- 0.13 | .006 +/- .001 | 484 +/- 33 | .004 +/- .001 | 558 +/- 27 |
| P15 TNAP$^{+/+}$ parietal | .007 +/- .002 | 0.61 +/- 0.12 | .006 +/- .001 | 501 +/- 30 | .004 +/- .001 | 568 +/- 19 |
| P20 TNAP$^{-/-}$ parietal | .011 +/- .002* | 0.68 +/- 0.01* | .009 +/- .001* | 539 +/- 32* | .007 +/- .001* | 612 +/- 21* |
| P20 TNAP$^{+/+}$ parietal | .015 +/- .003 | 0.74 +/- 0.08 | .011 +/- .002 | 574 +/- 30 | .009 +/- .002 | 637 +/- 19 |

*Indicates statistical significance between genotypes.

TABLE II

Comparison of Cranial Base Bone Volume, Density and Mineral Content in $Alpl^{-/-}$ vs. $Alpl^{+/+}$ Mice.

| | Base Volume (mm³) | Bone Volume Fraction | Bone Mineral Content (mg) | Bone Mineral Density (mg/cc) | Tissue Mineral Content (mg) | Tissue Mineral Density (mg/cc) |
|---|---|---|---|---|---|---|
| P15 TNAP$^{-/-}$ | 2.0 +/- 0.8* | 0.06 +/- 0.02 | 4.1 +/- 1.3* | 119 +/- 17 | 1.2 +/- 0.5* | 599 +/- 19* |
| P15 TNAP$^{+/+}$ | 2.5 +/- 0.5 | 0.06 +/- 0.02 | 5.1 +/- 0.7 | 125 +/- 21 | 1.6 +/- 0.4 | 642 +/- 28 |
| P20 TNAP$^{-/-}$ | 1.5 +/- 0.9* | 0.04 +/- 0.02* | 3.1 +/- 1.3* | 94 +/- 26* | 0.9 +/- 0.6* | 610 +/- 25* |
| P20 TNAP$^{+/+}$ | 3.4 +/- 1.1 | 0.08 +/- 0.02 | 5.7 +/- 1.4 | 127 +/- 21 | 2.3 +/- 0.8 | 667 +/- 24 |

*Indicates statistical significance between genotypes.

EXAMPLE 2

Materials and Methods

FGFR2C342Y/+Mice

All animal procedures were performed according to the University of Michigan's University Committee on Use and Care of Animals. FGFR2C342Y/+ mice were backcrossed onto the BALB/c strain for at least eight generations prior to analysis. Genotyping of FGFR2C342Y/+ mice was performed as previously described (Eswarakumar et al., Proc Natl Acad Sci USA 2004 Aug. 24; 101(34):12555-60). Briefly, DNA from tail digests was amplified by polymerase Ther 2010 June; 18(6):1094-102). A single injection of this bone-targeted lentivirus in neonatal mice was previously shown to result in a long-term high levels of TNAP enzyme expression and correction of the long bone hypo-mineralization phenotype seen in the TNAP null mouse model of infantile hypophosphatasia (Yamamoto et al., J Bone Miner Res 2011 January; 26(1):135-42).

In this study, five litters of mice (n=32 pups, 16 FGFR2+/+, 16 FGFR2C342Y/+) were injected three days after birth with the lentivirus ($1.0 \times 10^7$ transforming units per mouse) via the jugular vein. Four litters of mice (n=28 pups, 14 FGFR2+/+, 14 FGFR2C342Y/+), were injected with an equivalent volume of sterile phosphate buffered saline (PBS), to serve as controls. Each litter was injected with a different viral lot/preparation.

Serum Alkaline Phosphatase Activity, Phosphate and Calcium Analysis

Alkaline phosphatase activity serum levels were quantified by spectrophotometry, using the colorimetric reagent 4-nitrophenyl-phosphate disodium hexahydrate (Sigma). Serial dilutions of alkaline phosphatase enzyme (Sigma) were used to generate a standard curve to calculate alkaline phosphatase enzyme activity units for the experimental samples. Inorganic phosphate and calcium quantification was performed using commercially available kits (Pointe Scientific). Inorganic phosphorus (mg/dL) and calcium (mg/dL) levels were calculated by comparison to standard curves.

Micro-Computed Tomography

Whole skulls were dissected and fixed in ethanol. Calvaria were embedded in 1% agarose and scanned sing a micro-CT system (μCT100 Scanco Medical, Bassersdorf, Switzerland). Scan settings were: voxel size 18 μm, medium resolution, 70 kVp, 114 μA, 0.5 mm AL filter, and integration time 500 ms. Scans were calibrated to the manufacturer's hydroxyapatite phantom.

Suture Fusion Assessment

Patency or fusion of craniofacial sutures was established by serial viewing of individual slices in the axial, sagittal and coronal planes throughout the entire length of the suture in question using Microview Version 2.1.2 (GE Healthcare PreClinical Imaging, London, ON), as previously described (Hatch & Liu 2013). Presence or absence of bone fusion was verified by analysis of micro-CT scans by two independent reviewers.

Three-Dimensional Craniofacial Morphological Analysis

Three-dimensional X, Y, Z coordinate data from thirty-three landmarks placed on micro-CT images of mouse skulls were used to quantifiably assess craniofacial form in this study, as previously described. Landmarks were placed via simultaneous viewing on two dimensional slices of skulls using Dolphin Imaging 11.0 software (Dolphin Imaging and Management Solutions, Chatsworth, Calif.). This software is able to display the skulls in the axial, sagittal, and coronal slices with the three-dimensional surface reconstruction for landmark verification in all views simultaneously. Reliability of this method was previously reported (Liu et al., Calcif Tissue Int 2013 May; 92(5):451-66). Landmark coordinate data were imported into WinEDMA 1.0.1 software (Theodore Cole, Department of Basic Medical Science, School of Medicine, University of Missouri, Kansas City, Mo.). This software uses three-dimensional x, y, z coordinate data from each sample to quantify and compare forms between two sample populations by Euclidean distance matrix analysis (EDMA), which allows for an invariant statistical comparison of forms. Briefly, EDMA is a morphometric analysis created by Richstmeier and Lele in 2001 that uses landmark coordinate data without using a fixed coordinate axis (Lele S, Richtsmeier J T. An invariant approach to statistical analysis of shapes. Boca Raton, Fla.: Chapman & Hall/CRC; 2001). This analysis calculates all the linear distances between all possible pairs of landmarks in each individual and compares these distances as ratios between groups.

In this study, Crouzon mice injected with the TNAP lentivirus (litters 1-4) were compared with Crouzon mice injected with vehicle (PBS). Litter 5 was not used for EDMA analysis since their serum alkaline phosphatase levels were comparable to PBS injected mice, indicating lack of efficacy of the virus in these mice. Landmarks were grouped into regional subsets (Table 3), due to the high number of landmarks used. All bootstrapping procedures were calculated with 1000 resamples and confidence intervals were calculated with a one-way $\alpha=0.05$.

Statistical Analysis

Mice injected with the TNAP lentivirus displayed varying levels of AP enzyme activity, indicating variable efficacy of the virus. Therefore, logistic regression was used to model the log odds of the binary outcome of cranial suture or synchondrosis fusion versus nonfusion as a linear function of AP enzyme activity. This statistical model allows us to draw conclusions about the relationship between the level of AP enzyme activity and our ability to influence suture fusion, despite the variability in AP enzyme activity levels between mice. Linear regression was used to analyze the effect of the AP level, genotype, and gender on continuous outcomes including body weight, body length, serum inorganic phosphorus and serum calcium levels.

Results

Serum Alkaline Phosphatase Activity

Figure 10:
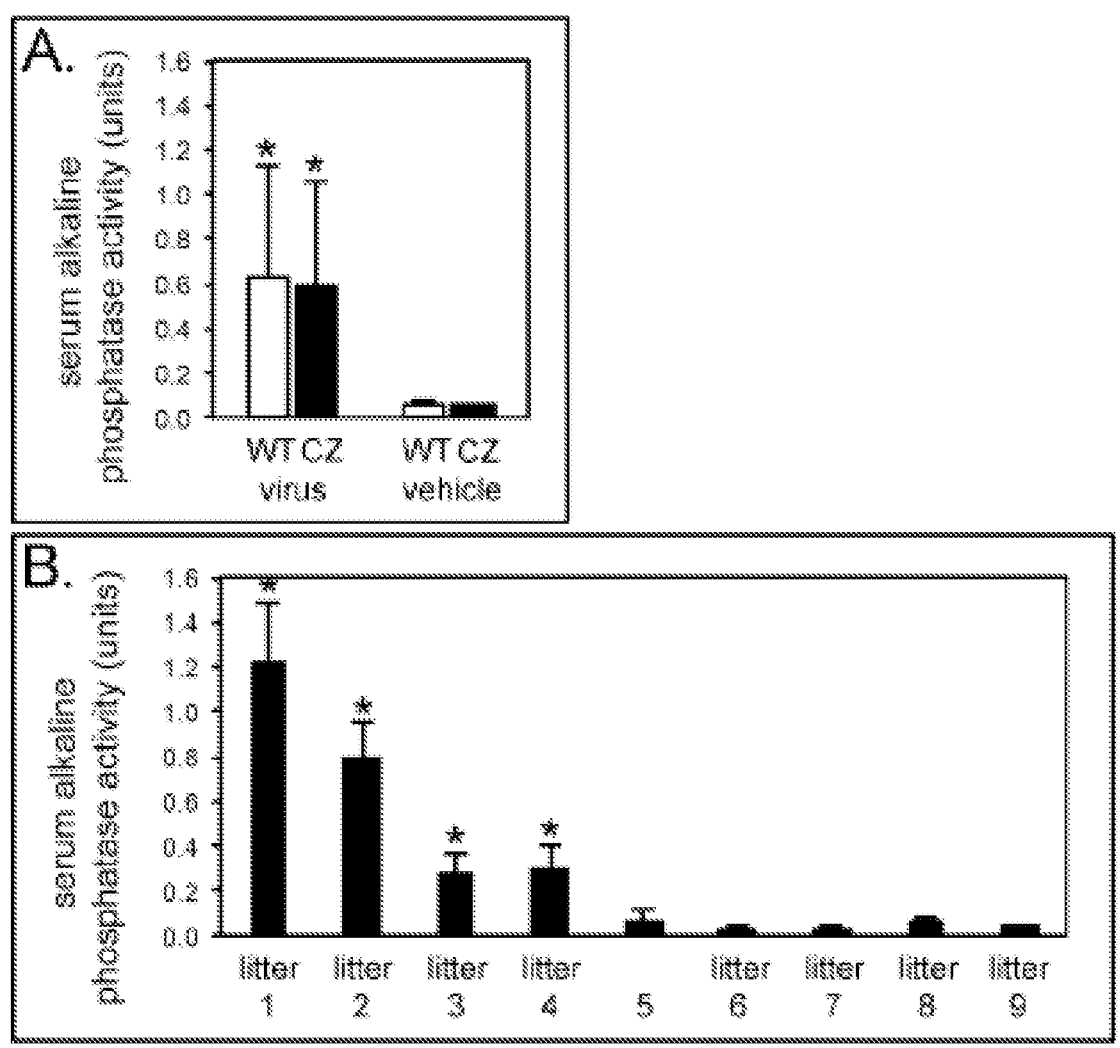
FIG. 10 shows serum alkaline phosphatase enzyme activity levels by genotype, treatment group and litter of mice. *p<0.05 vs. control mice

Injection with the lentivirus significantly increased serum alkaline phosphatase (AP) enzyme activity levels, when compared to PBS injected mice. Despite injecting similar titers of virus, AP levels showed high variability, which was dependent upon the lot of virus/litter injected (FIG. 10). AP activity per litter steadily declined with each subsequent litter of mice. The first litter of mice (n=8) had the highest AP activity, with an average level of 1.2 units. The second litter of mice (n=7) had an average AP level of 0.790 units, while the third and fourth litters had even lower levels. The fifth litter was injected with the lentivirus but showed AP activity levels similar to that seen in PBS injected mice. No differences between genotypes or genders were found.

Body Weight and Body Length Measurements

For body weight, with every unit increase in AP level, there is a decrease in body weight by 1.4 grams for both Crouzon and wild type mice (p=0.004) (Table 3). Although Crouzon mice weigh on average 2.9 grams less than wild type mice regardless of AP level (p<0.0001), there is no statistically significant interaction between AP level and genotype. In other words, AP level did not have a greater or lesser effect on overall body weight in Crouzon mice than in wild type mice. The overall R2 value is 0.519 (overall p<0.0001), which means that the regression model accounts for 51.9% of the variability in weight. For body length, with every unit increase in AP level, there is a decrease in body length by 4.5 mm for both Crouzon and micro-CT mice (p<0.003) (Table 3). Crouzon mice measure on average 6.5 mm less than wild type mice regardless of AP level (p<0.0001). In other words, AP level did not have a greater or lesser effect on overall body length in Crouzon mice than in wild type mice. The overall R2 value is 0.395 (overall p<0.0001) which means that the regression model accounts for 39.5% of the variability in body length.

Serum Inorganic Phosphorus and Calcium Assays

AP level, genotype and gender did not have a statistically significant effect on serum inorganic phosphorus or calcium levels.

Suture Fusion

Figure 11:
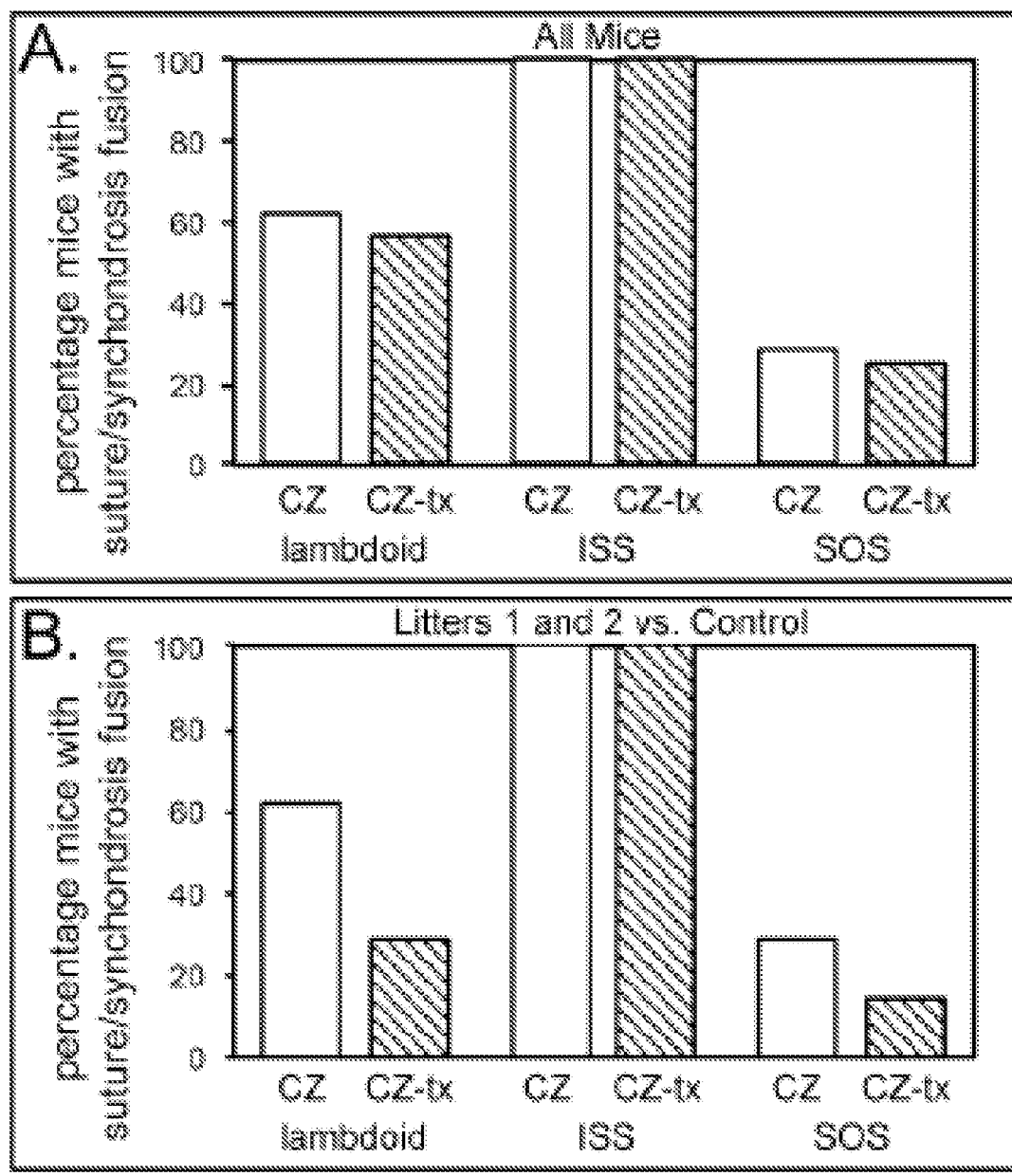
FIG. 11 shows the percentage of TNAP lentivirus injected (tx) vs. control FGFR2C342Y/+ (Cz) mice with cranial suture and synchondrosis fusion.

All Crouzon mice, regardless of treatment, exhibited fusion of the intersphenoidal synchondrosis (ISS, located between the presphenoid and basisphenoid bones of the anterior cranial base). No Crouzon mice, regardless of treatment, exhibited fusion of the sagittal suture. The spheno-occipital synchondrosis (SOS, located between the basisphenoid and basioccipital bones of the posterior cranial base) was fused in 28.6% of control Crouzon mice and in 25.0% of lentivirus injected Crouzon mice. The lambdoid suture was fused in 61.9% of control Crouzon mice and in 56.3% of lentivirus injected Crouzon mice (FIG. 11A).

Injection with the lentivirus resulted in higher expression levels in the first two litters of injected mice than in subsequent litters. When comparing these two treatment litters with all control litters, the SOS was fused in 28.6% of control Crouzon mice and in 14.3% of lentivirus injected Crouzon mice. The lambdoid suture was fused in 61.9% of control Crouzon mice and in 28.6% of lentivirus injected Crouzon mice (FIG. 11B).

To account for the variable efficacy of injected virus, logistic regression was used to assess the effect of AP level on suture fusion in Crouzon mice. For the spheno-occipital suture, for every unit increase in AP level, the odds of fusion decreases by 41.7%. However the p value did not reach significance (p=0.602). For the lambdoid suture, for every unit increase in AP level, the odds of fusion decreases by 84.2%. This result falls just short of significance (p=0.068) (Table 4).

Morphological Analysis

EDMA was used to quantify craniofacial form differences between TNAP injected Crouzon mice and control Crouzon mice. The craniofacial subset comparisons that were statistically significant according to the non-parametric bootstrapping procedure were for the inferior surface (p=0.02) and cranial vault vertical (p=0.01) regions (Table 5). EDMA results indicate that the overall effect of the TNAP lentivirus treatment is a decrease in skull length in both vertial and transverse dimensions. It has been shown that calvarial width and vertical height of Crouzon mice is increased when compared to wild type mice. Calvarial vertical height and transverse dimensions were diminished in lentivirus injected Crouzon mice as compared to control Crouzon mice, indicating that delivery of the recombinant TNAP enzyme rescues this abnormality in shape.

TABLE 3

Body Weight and Length as Influenced by AP level, genotype and gender.

| Overall | | | Coefficient | 95% Confidence Intervals | |
|---|---|---|---|---|---|
| $R^2$ with p value | Parameters | | (β) with p value | lower bound | upper bound |
| Body Weight (g) | $R^2$ = .519 p < .0001 | intercept | 14.04 p < .0001 * | 13.20 | 14.88 |
| | | AP level | −1.42 p = .004 * | −2.36 | −0.47 |
| | | Genotype (Cz) | −2.88 p < .0001 * | −3.70 | −2.08 |
| | | Gender (F) | −0.55 p = .12 | −1.38 | .28 |
| Body Length (mm) | $R^2$ = .395 p < .0001 | intercept | 78.38 p < .0001 * | 75.73 | 81.04 |
| | | AP level | −4.547 p = .003 * | −7.53 | −1.56 |
| | | Genotype (Cz) | −6.513 p < .0001 * | −9.08 | −3.95 |
| | | Gender (F) | −2.175 p = .10 | −4.80 | 0.46 |

* Indicates statistical significance between genotypes.

TABLE 4

Cranial suture and synchondrosis fusion as Influenced by AP level.

| Suture or Synchondrosis | Parameter | Cofficient (β) with p value | 95% Confidence Intervals | | Odds Ratio for Fusion |
|---|---|---|---|---|---|
| | | | lower bound | upper bound | |
| Lambdoid | AP level | −1.85 p < .068 | 0.02 | 1.14 | 84.2% |
| SOS | AP level | −0.54 p < .602 | .08 | 4.4 | 41.7% |

TABLE 5

Craniofacial Morphologic Analysis.

| Landmark Subset | Number of Landmarks in Subset | Form Comparison p value |
|---|---|---|
| superior surface | 9 | .080 |
| inferior surface | 9 | .023* |
| lateral surface | 9 | .657 |
| cranial vault vertical | 7 | .014* |
| cranial vault transverse | 7 | .496 |

Euclidean distance matrix analysis reveals form differences in craniofacial regions between experimental and control Crouzon mice.
The p-value reported is for the T-statistic bootstrapping procedure to test the null hypothesis of similarity in form between groups.
*statistical significance between groups.

EXAMPLE 3

Materials and Methods

Animals

Preparation and genotyping of Alpl+/− mice were previously reported (Narisawa S, et al., Dev Dyn. 1997; 208:432-446; Hessle L, et al., Proc Natl Acad Sci. 2002; 99:9445-9449; Yadav M C, et al., Bone. 2011; 49(2):250-6). Alpl+/− mice were maintained in a 12.5% C57Bl/6-87.5% 129 J mixed genetic background. Alpl−/− and wild type (Alpl+/+)

mice were obtained by heterozygous breeding. Mice were given free access to modified rodent diet containing increased levels of pyridoxine (vitamin B6, 325 ppm) to suppress seizures and extend life span in Alpl−/− mice. Animal use followed federal guidelines for the care and use of animals in research. Alpl−/− mice on this background are variable in terms of severity their bone phenotype. Severity of the long bone mineralization defect in Alpl−/− mice was scored using mouse paw radiographs, as follows. A normal paw phenotype has all secondary ossification centers present and mineralized digits. A mild phenotype has some secondary ossification centers absent and mineralized digits. A moderate phenotype has all secondary ossification centers absent and mineralized digits. A severe phenotype has profound dysmorphology, with absent ossification centers and no digit mineralization.

Enzyme Replacement

Recombinant TNAP enzyme (asfotase-alfa) is composed of soluble human TNAP fused to the constant region of human IgG1 (Fc), and a C-terminal deca-aspartate motif that confers targeting to hydroxyapatite (Whyte M P, et al., N Engl J Med. 2012; 366(10):904-13; Nishioka T, et al., Mol Genet Metab. 2006; 88(3):244-55). Alpl−/− mice were injected subcutaneously with 2.0 or 8.2 mg/kg of protein starting at birth, according to previously established protocols for rescue of murine HPP. Efficacy of this dose and delivery method for this recombinant form of TNAP was previously shown to increase serum alkaline phosphatase levels; and rescue long bone, rib, vertebral and tooth defects in murine HPP (Millan J L, et al., J Bone Miner Res. 2008; 23:777-87; Yadav M C, et al., Bone. 2011; 49(2):250-6; McKee M D, et al., J Dent Res. 2011; 90:470-6). Craniofacial skeletal assessments were performed on treated Alpl−/− mice, as compared to untreated Alpl−/− mice and wild type controls. Animal genotype and treatment group was blinded for analyses, then unblinded for statistics.

Linear Craniofacial Measurements

Digital calipers were used to conduct craniofacial linear skeletal measurements because identification of some skeletal landmarks on micro CT scans can be difficult due to craniofacial bone hypomineralization in untreated Alpl−/− mice. 15-day-old untreated Alpl−/− (n=46), 8.2 mg/kg/day treated Alpl−/− (n=45) and control Alpl+/+ (n=46) mouse skulls were carefully dissected and fixed. Linear measurements were calculated using previously reported craniofacial skeletal landmarks (Richtsmeier J T, et al., Dev Dyn. 2000; 217(2):137-45; Perlyn C A, et al., Cleft Palate Craniofac J. 2006; 43(6):740-8; Liu J, et al., Calc Tissue Int. 2013; 92(5):451-466; Liu J, et al., Bone. 2014; 67:81-94) including five standard measurements currently in use by the Craniofacial Mutant Mouse Resource of Jackson Laboratory (Bar Harbor, Me.). Linear measurements were normalized to total skull length (measured from nasale to opisthion) to account for potential size differences between Alpl−/− and Alpl+/+ mice. No significant difference between genders was found therefore genders were combined for comparison of genotype and treatment groups.

Micro Computed Tomography

Whole skulls were scanned at an 18 μm isotropic voxel resolution using the eXplore Locus SP micro-computed tomography imaging system (GE Healthcare Pre-Clinical Imaging, London, ON, Canada), as previously described (Liu et al, Bone. 2014; 67:81-94; Liu J, et al., Calc Tissue Int. 2013; 92(5):451-466). Density, volume and mineral content of cranial bones was measured using previously established methods and regions of interest using Microview version 2.2 software (GE Healthcare Pre-Clinical Imaging, London, ON) and established algorithms (Liu J, et al., Calc Tissue Int. 2013; 92(5):451-466; Meganck J A, et al., Bone. 2009; 45(6):1104-1116; Umoh J U, et al., Phys Med Biol. 2009; 54(7):2147-61).

Craniofacial Morphometric Analysis

A subset of thirty-three previously established craniofacial landmarks were placed on micro CT scans of the 15-day-old skulls, and included only those landmarks that were readily visualized on micro CT scans of all samples (Richtsmeier J T, et al., Dev Dyn. 2000; 217(2):137-45; Liu J, et al., Calc Tissue Int. 2013; 92(5):451-466). Landmarks were placed and landmark coordinate data was generated using Dolphin Imaging 11.0 software (Dolphin Imaging and Management Solutions, Chatsworth, Calif.), as previously reported (Liu J, et al., Calc Tissue Int. 2013; 92(5):451-466). Landmark coordinate data was imported into WinEDMA 1.0.1 software (Department of Basic Medical Science, School of Medicine, University of Missouri, Kansas City, Mo.) for comparison of form, size and shape by Euclidean Distance Matrix Analysis (EDMA) (Liu J, et al., Calc Tissue Int. 2013; 92(5):451-466; Lele S and Richtsmeier J T. An invariant approach to statistical analysis of shapes. 2001, Chapman & Hall/CRC, Boca Raton, Fla.). Briefly, EDMA is a morphometric analysis that uses landmark x, y, z coordinate data without using a fixed coordinate axis. The analysis calculates all the linear distances between all possible pairs of landmarks in each individual and compares these distances as ratios between groups.

Craniosynostosis Assessment

Fusion of the coronal suture (fusion between frontal and parietal bones), sagittal suture
(fusion between the right and left parietal bones) and lambdoid sutures (fusion between parietal and intraparietal bones) was identified on micro CT scans of dissected calvaria. Cranial sutures were viewed using the two-dimensional micro-CT slices in an orthogonal view across the entire length of the coronal suture, as previously described (Liu J, et al., Calc Tissue Int. 2013; 92(5):451-466; Liu et al, Bone. 2014; 67:81-94; Perlyn et al., Cleft Palate Craniofac J. 2006; 43(6):740-8). Bone fusions identified on micro CT images were verified by visualization of specimens under a dissecting microscope (Leica M60 TL5000; Leica Microsystems Inc., Buffalo Groves, Ill.).

Histology

For microscopic visualization of mineralized tissues; dissected and fixed skulls were serially dehydrated, washed in isopropanol, incubated in xylene and then embedded in methyl methacrylate. This method does not remove mineral and therefore allows for assessment of bone fusion. Methacrylate blocks were trimmed in the sagittal plane to within 4 mm of the sagittal suture. 4 μM sections perpendicular to the coronal suture were prepared with a Leica RM2255 microtome equipped with a tungsten carbide blade (Leica Microsystems Inc., Buffalo Groves, Ill.). Sections were transferred to slides and dried overnight. Sections were stained for mineral by incubation in 5% AgNO3 (Von Kossa stain) followed by counter-staining in a 1% toluidine blue 1% sodium borate solution.

To assess proliferation in mouse calvarial tissues; fixed and decalcified tissues from 5 dayold mice were paraffin embedded. 8 μM sections perpendicular to the coronal suture were sectioned and stained using anti-Ki67 primary antibody (Spring Bioscience), a horse radish peroxidase-conjugated secondary antibody, colorimetric detection with chromogen diaminobenzidine (DAB) and counter staining with hematoxylin and eosin.

Cell Preparation and Culture

Primary cells were isolated from dissected calvaria by collagenase digestion, as previously described (Liu J, et al., Calc Tissue Int. 2013; 92(5):451-466; 42]. Briefly, bones were rinsed with media then serially digested in a solution containing 2 mg/ml collagenase P and 1 mg/ml trypsin. Cells from the third digestion were utilized for experiments. TNAP specific shRNA and non-target shRNA expressing MC3T3E1(C4) pre-osteoblastic calvarial cells were previously characterized (Liu et al, Bone. 2014; 67:81-94). Cells were induced to differentiate by culture in custom formulated aMEM media containing no phosphate, supplemented with 50 ug/ml ascorbate, 10% fetal bovine serum (FBS) and 10,000 μg/ml penicillin/streptomycin (P/S). Where indicated, sodium phosphate was added at a final concentration of 5 mM. RNA was isolated using Trizol reagent (Invitrogen) following manufacturer protocols. mRNA levels were assayed by reverse transcription and real time PCR.

Real time PCR was performed utilizing the murine glyceraldehye 3-phosphate dehydrogenase (GAPDH) primer/probe set Mm01545399_m1, the murine osteocalcin (OCN) Mm03413826_mH primer/probe set, the murine bone sialoprotein (BSP) primer/probe set Mm00492555_m1, the murine tissue non-specific alkaline phosphatase (TNAP) primer/probe set Mm00475834_m1, the murine Runx2 primer/probe set Mm00501578_m1 and Taqman Universal PCR Master Mix (Applied Biosystems). Real-time PCR was performed on a GeneAmp 7700 thermocyler (Applied Biosystems) and quantified by comparison to a standard curve. mRNA levels are reported after normalization to GAPDH mRNA levels. Alkaline phosphatase enzyme activity was assayed using the colorimetric substrate, NBT/BCIP (Sigma). For quantification, wells were scanned and densitometry was measured using NIH Image software. To assay cellular proliferation, cells were seeded and grown in media containing 10% fetal bovine serum for five days. Cells were stained with trypan blue and counted in quintuplet at each time point.

Results

Figure 13:
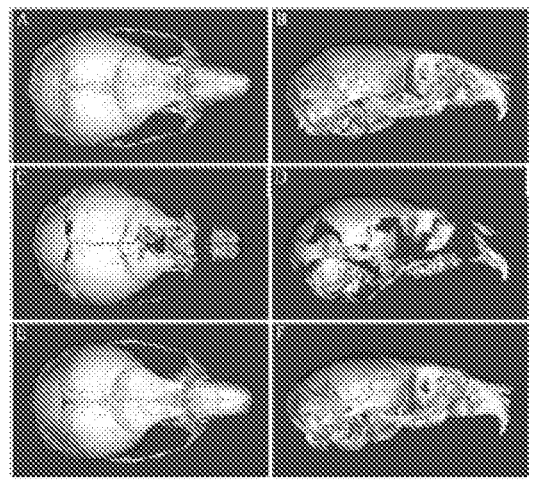
FIG. 13 shows qualitative rescue of craniofacial mineralization and shape abnormalities by mineral-targeted TNAP enzyme replacement in murine HPP. Micro CT based, isosurface images of 15-day post-natal Alpl+/+ (A,B), untreated Alpl−/− (C,D) and treated Alpl−/− mouse skulls (E,F) are shown.

TNAP Enzyme Replacement Rescues Mineralization Defects in the Craniofacial Skeleton of Alpl−/− Mice Micro CT isosurface images of 15 day-old Alpl−/− mice treated with 8.2 mg/kg/day of recombinant enzyme (FIG. 13E,F) show rescue of craniofacial bone mineralization defects, when compared to untreated Alpl−/− (FIG. 13C,D) and wild type mice (FIG. 13A,B). Consistent with the typical HPP phenotype, multiple cranial vault and facial bones of untreated Alpl−/− mice lack adequate mineralization to appear on micro CT scans constrained to a bone tissue threshold. This hypomineralization phenotype is not evident in treated Alpl−/− mice. Micro CT based quantification of individual cranial bones revealed a surprising phenotype involving increased frontal bone mineral volume, density and mineral content in untreated Alpl−/− mice, as compared to wild type mice at post-natal day 15 (Table 6). This phenotype was not seen in the treated Alpl−/− mice. Tissue mineral content of the parietal bone was also increased in untreated P15 Alpl−/− mice but not in treated Alpl−/− mice. Together, these results indicate that treatment with mineral-targeted TNAP normalizes both hypomineralization (eg: maxilla, zygoma and anterior aspects of frontal bone) and hypermineralization (e.g., parietal bone and posterior aspects of frontal bone) defects seen in the craniofacial skeleton of Alpl−/− mice.

TNAP Enzyme Replacement Rescues Craniosynostosis in Alpl−/− Mice

Figure 14:
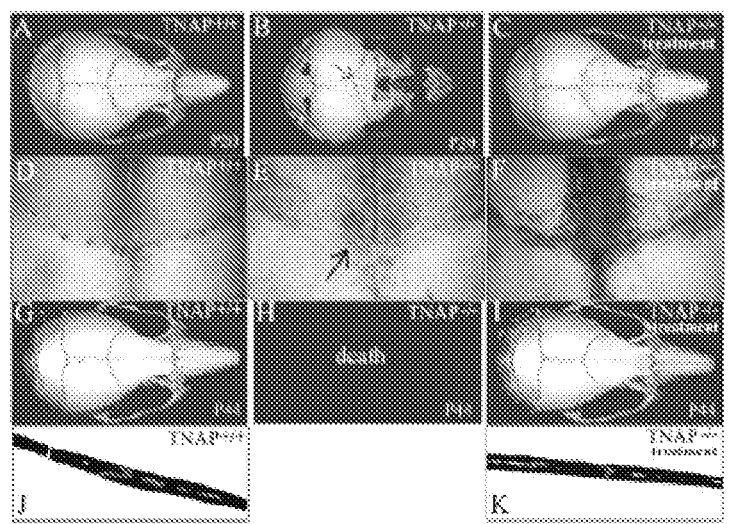
FIG. 14 shows mineral-targeted TNAP enzyme replacement rescues craniosynostosis in murine HPP. A,B,C) Isosurface micro CT images show coronal suture fusion present in untreated P20 Alpl−/− mice (B), but not in 2.0 mg/kg/day treated Alpl−/− (C) or in Alpl+/+ (A) mice (arrow points to fused coronal suture in untreated P20 Alpl−/− mice). D,E,F) Dissected skulls of P20 mice were visualized through a dissection microscope. Fusion of the coronal suture is apparent in untreated Alpl−/− (E) but not in treated Alpl−/− (F) or in Alpl+/+ (D) mice (black arrow points to fused coronal suture in untreated P20 Alpl−/− mice). G,H,I) Isosurface micro-CT images show that treated P44 Alpl−/− mice show no evidence of craniosynostosis. Skulls of P44 8.2 mg/kg/day treated mice (I) appear normal, as compared to Alpl+/+ (G) mice (H). Because untreated Alpl−/− mice do not survive past three weeks post-birth, untreated P44 Alpl−/− cannot be shown. J, K) Histologic staining of non-decalcified bone surrounding the coronal suture of P44 skulls is shown (black stain is mineralized tissue (32×).

Bony fusion between frontal and parietal bones (fusion of the coronal suture) occurs in approximately one third of Alpl−/− mice between two and three weeks after birth (Liu et al, Bone. 2014; 67:81-94). Results described herein show that TNAP enzyme replacement prevents craniosynostosis. Craniosynostosis in the form of coronal suture fusion is evident in untreated Alpl−/− mice, but not in Alpl−/− mice treated with 2.0 g/kg/day or 8.2 mg/kg/day recombinant TNAP enzyme; as demonstrated by micro CT, microscopic visualization of dissected skulls and histology (FIG. 14). Craniosynostosis was not seen in any treated Alpl−/− mice (n=16) and the incidence of coronal suture fusion was significantly higher in untreated compared to treated Alpl−/− mice (p<0.05, two tailed Fisher's exact test).

Figure 15:
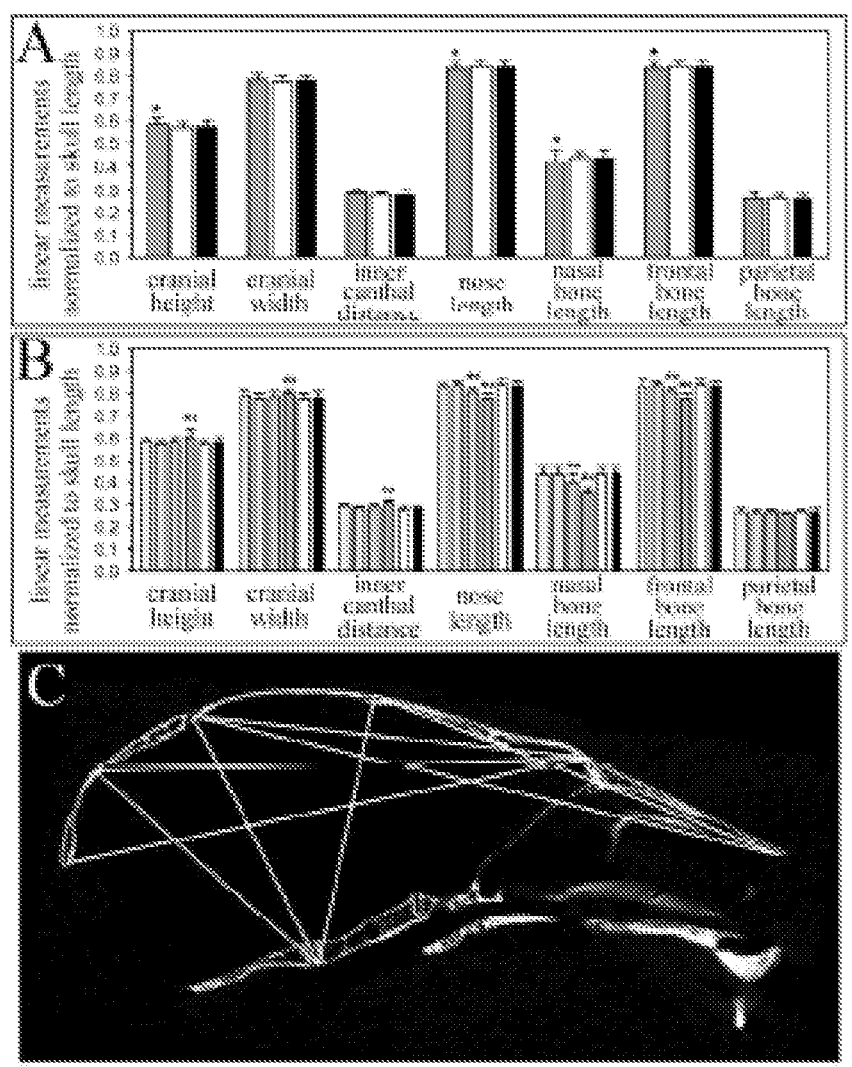
FIG. 15 shows that TNAP enzyme replacement normalizes craniofacial shape abnormalities in murine HPP. A) When grouped by genotype and treatment, linear craniofacial measurements of P15 mice show that untreated Alpl−/− mice exhibit increased cranial height and decreased nose length, nasal bone length and frontal bone length as compared to wild type mice. Grey=untreated Alpl−/−, white=Alpl+/+, black=8.2/mg/day treated Alpl−/−. B) Severity of the HPP phenotype is variable in Alpl−/− mice on this mixed genetic background. C) Representative craniofacial landmark distance EDMA mean ratios calculated using x, y, z coordinate data from micro CT scans, are shown on a mouse skull sagittal micro CT section.

TNAP Enzyme Replacement Diminishes Craniofacial Shape Abnormalities in Alpl−/− Mice Alpl−/− mice exhibit craniofacial shape abnormalities within two weeks after birth (Liu et al, Bone. 2014; 67:81-94). Daily treatment with 8.2 mg/kg of mineral-targeted soluble TNAP rescued these abnormalities to a large extent. Digital caliper linear measurements normalized to skull length demonstrate that nose length, nasal bone length and frontal bone length are shorter in P15 untreated Alpl−/− mice, but not in treated Alpl−/− mice when compared to wild type controls (FIG. 15A). Because severity of the HPP phenotype is variable in Alpl−/− mice on this mixed genetic background, craniofacial shape differences were measured by severity of the long bone hypomineralization phenotype. These results reveal more extreme craniofacial skeletal defects in P15 Alpl−/− mice that are dependent both upon severity of the HPP long bone mineralization phenotype and TNAP enzyme supplementation (FIG. 15B). Cranial height, cranial width and inner canthal distance are significantly larger; while nose length, nasal bone length and frontal bone length are significantly smaller in Alpl−/− mice of the severe long bone ossification phenotype category, when compared to treated Alpl−/− and Alpl+/+ mice. All Alpl+/+ and 44 of 46 treated Alpl−/− mice were scored as having normal long bone ossification phenotypes (two treated Alpl−/− mice were scored as having mild long bone ossification phenotypes) and all of these mice also had a normal craniofacial shape.

Three-dimensional coordinate data from landmarks placed on micro CT scans of mouse skulls were also used to compare craniofacial form and shape by Euclidean Distance Matrix Analysis (EDMA). Results show that the overall craniofacial skeletal form (form includes size and shape) of untreated Alpl−/− mice is different than that of Alpl−/− mice treated with 8.2 mg/kg/day of recombinant TNAP (T=1.10, p<0.001) by two weeks after birth. Shape analysis using geometric mean as a scaling factor confirmed that untreated vs. treated skulls are also statistically different in shape by two weeks after birth (Z=−0.052, □=0.01). EDMA shape confidence intervals for individual linear measurements were consistent with results of the digital caliper analysis. Anterior-posterior skull length distances were smaller while skull height distances were larger in untreated, when compared to treated Alpl−/− mice (FIG. 15C). Together these results support the assessment that TNAP enzyme replacement minimizes the skull and facial shape defects seen in affected Alpl−/− mice. Overall untreated Alpl−/− mice have skulls are acrocephalic (tall) and brachycephalic (wide), when compared to those of treated of Alpl−/− mice and wild type controls.

Figure 16:
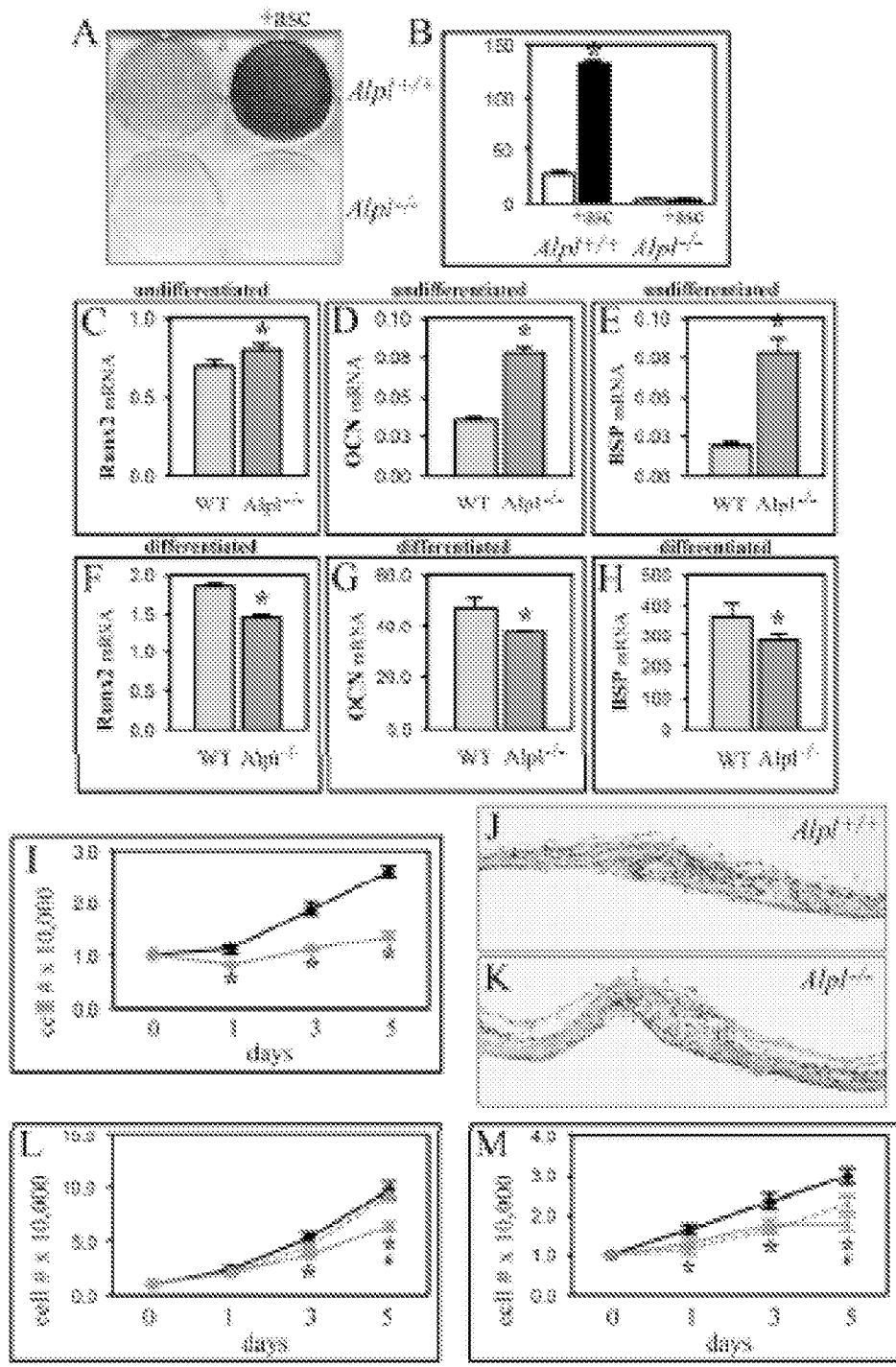
FIG. 16 shows gene expression and proliferation changes in Alpl−/− calvarial cells. (A,B) Primary calvarial cells were cultured with ascorbate to induce osteoblast differentiation. (C-H) RNA was isolated from cells after culture with or without ascorbate to induce osteoblast differentiation. Runx2, osteocalcin (OCN) and bone sialoprotein (BSP) mRNA levels were measured by real time PCR. (I) Cells were stained with trypan blue and counted at indicated time points after plating to assay for proliferation. (J, K) Calvarial tissue sections were stained with Ki67 antibody as a marker of proliferation. 10× magnification of parietal and frontal bones surrounding the coronal suture from P5 Alpl+/+ (J) and Alpl−/− (K) mice are shown. Note diminished number of proliferative cells in Alpl−/− calvaria. (L) MC3T3E1(C4) cells stably transduced with TNAP specific or non-target shRNA were cultured in media supplemented with/without 5mM sodium phosphate. Inorganic phosphoate (Pi) increased the proliferation of Alpl−/− cells (M).
Figure 17:
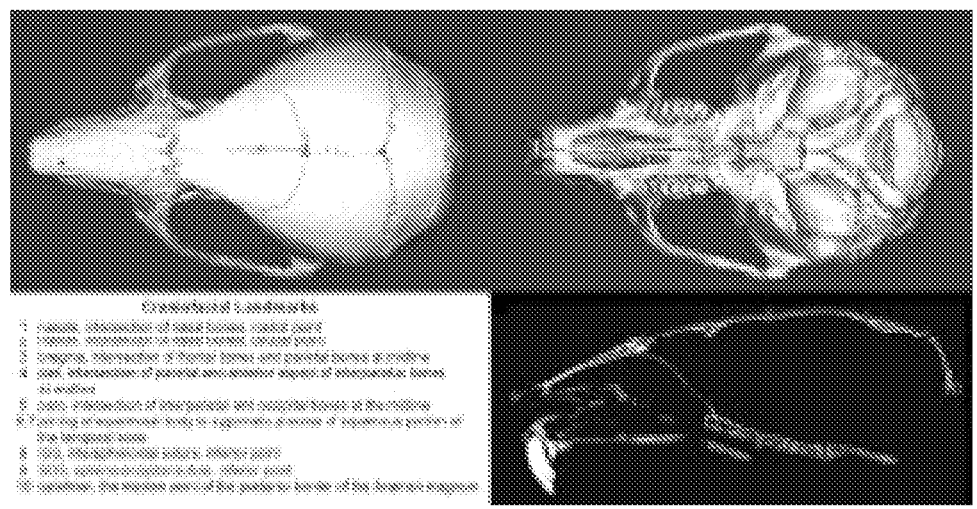
FIG. 17 shows craniofacial Landmarks used to perform Euclidean distance matrix analysis.

Role of Inorganic Phosphate (Pi) in TNAP Deficiency Induced Cellular Abnormalities Calvarial MC3T3E1(C4) cells in which TNAP expression was suppressed by shRNA exhibit cellular abnormalities including aberrant osteoblastic gene expression and diminished proliferation [25]. Consistent with this data, primary cells isolated from Alpl−/− calvaria express higher levels of Runx2, osteocalcin (OCN) and bone sialoprotein (BSP) mRNA before osteoblast differentiation in culture (FIG. 16C-E) and lower levels upon differentiation, when compared to wild type cells (FIG. 16F-H). Alpl−/− cells are also less proliferative than Alpl+/+ cells (FIG. 16I). Diminished proliferation of bone lining and suture cells is also apparent in Alpl−/− calvaria (FIG. 16K) as compared to Alpl++/ (FIG. 16J). Regions of high proliferation are evident along the leading edge of both frontal and parietal bones adjacent to the coronal suture in wild type mice. Less proliferation is evident in these and other regions of Alpl−/− calvarial tissues.

Alpl−/− mice do not exhibit systemic hypophosphatemia but TNAP does function to generate inorganic phosphate (Pi) at the extracellular membrane (Johnson K A, et al., Am J Physiol Regul Integr Comp Physiol. 2000; 279:R1365-1377; Hessle L, et al., Proc Natl Acad Sci. 2002; 99:9445-9449). Extracellular Pi influences matrix mineralization, and can also stimulate changes in gene expression and proliferation (Nam H K, et al., J Biol Chem 2011; 286(45):39059-71; Conrads K A, et al., Mol Cell Proteomics. 2005; 4(9): 1284-96; Khoshniat S, et al., Cell Mol Life Sci. 2011; 68(2):205-18; Camalier C E, et al., J Cell Physiol. 2013; 228(7):1536-50). Therefore, the potential for Pi to rescue proliferation and gene expression abnormalities seen in TNAP deficient cells was assayed. Results show that addition of Pi to culture media increased the proliferation of TNAP deficient MC3T3E1(C4) cells to the levels seen in control cells (FIG. 16L). Consistently, Pi also increased the proliferation of Alpl−/− cells (FIG. 16M). Treatment with Pi did not rescue gene expression differences between TNAP deficient and control MC3T3E1(C4) cells, or between Alpl−/− and Alpl+/+ cells. Together these results indicate that diminished extracellular Pi mediates some but not all of the cellular changes induced by TNAP deficiency.

In conclusion, post-natal treatment with a mineral-targeted form of TNAP (asfotase-alfa) is efficacious for preventing craniosynostosis and diminishing craniofacial shape defects in murine infantile HPP. Infantile hypophosphatasia is a progressive disorder and craniosynostosis in HPP and other rachitic disorders tends to occur later than that seen in other forms of craniosynostosis (Seruya M, et al., J Craniofac Surg. 2013; 24(1):96-8).

TABLE 6

Cranial Bone Volume, Density and Mineral Content in untreated vs. treated Alpl−/− and Alpl+/+ Mice.

|  | Bone Volume Fraction | Bone Mineral Content (mg) | Bone Mineral Density (mg/cc) | Tissue Mineral Content (mg) | Tissue Mineral Density (mg/cc) |
| --- | --- | --- | --- | --- | --- |
| Alpl$^{-/-}$ vehicle frontal | 0.31 +/− .16# | .007 +/− .002*# | 441 +/− 67*# | .003 +/− .002# | 602 +/− 31*# |
| Alpl$^{-/-}$ treatment frontal | 0.23 +/− .10 | .006 +/− .001 | 401 +/− 34 | .002 +/− .001 | 580 +/− 26 |
| Alpl$^{+/+}$ frontal | 0.25 +/− .15 | .006 +/− .002 | 411 +/− 49 | .002 +/− .002 | 569 +/− 28 |
| Alpl$^{-/-}$ vehicle parietal | 0.32 +/− .13 | .007 +/− .001 | 432 +/− 39 | .003 +/− .002 | 594 +/− 27* |
| Alpl$^{-/-}$ treatment parietal | 0.29 +/− .12 | .003 +/− .001 | 415 +/− 42 | .003 +/− .001 | 579 +/− 32 |
| Alpl$^{+/+}$ none parietal | 0.37 +/− .12 | .007 +/− .001 | 443 +/− 37 | .003 +/− .002 | 579 +/− 27 |

*Indicates statistical significance between genotypes.
indicates statistical significance between treatment groups.

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

I claim:

1. A method of treating or preventing craniosynostosis, comprising administering an alkaline phosphatase polypeptide to a human subject selected from the group consisting of a neonatal human subject, a human fetus, and a human embryo, wherein said alkaline phosphatase polypeptide decreases coronal suture fusion in the human subject.

2. The method of claim 1, wherein the alkaline phosphatase polypeptide is selected from the group consisting of: tissue non-specific alkaline phosphatase (TNALF), placental alkaline phosphatase (PALP), germ cell alkaline phosphatase (GCALP), intestinal alkaline phosphatase (IALP), asfotase alfa, and any functional fragment thereof.

3. The method of claim 1, wherein the alkaline phosphatase polypeptide comprises a soluble alkaline phosphatase (sALP).

4. The method of claim 1, wherein the alkaline phosphatase polypeptide comprises a bone-targeting moiety.

5. The method of claim 4, wherein the alkaline phosphatase polypeptide comprises a polypeptide having the structure selected from the group consisting of: Z-sALP-Y-spacer-X-$W_n$-V and Z-$W_n$-X-sALP-Y-spacer-V, wherein V is absent or is an amino acid sequence of at least one amino acid;

X is absent or is an amino acid sequence of at least one amino acid;

Y is absent or is an amino acid sequence of at least one amino acid;

Z is absent or is an amino acid sequence of at least one amino acid; and $W_n$ is a polyaspartate or a polyglutamate wherein n is 3-20.

6. The method of claim 5, wherein the spacer comprises a fragment crystallizable region (Fc).

7. The method of claim 6, wherein the Fc is the Fc of an immunoglobulin selected from the group consisting of IgG-1, IgG-2, IgG-3, and IgG-4.

8. The method of claim 2, wherein the TNALP comprises the amino acid sequence set forth by SEQ ID NO: 2.

9. The method of claim 5, wherein the alkaline phosphatase polypeptide comprises the amino acid sequence set forth by SEQ ID NO: 6 or SEQ ID NO: 7.

10. The method of claim 9, wherein the alkaline phosphatase polypeptide consists of the amino acid sequence set forth by SEQ ID NO: 7.

11. The method of claim 1, wherein said administering is in utero is initiated within 1 day of birth, within 3 days of birth, within 1 week of birth, or within 2 weeks of birth.

12. The method of claim 1, wherein said administering is repeated at least once.

13. The method of claim 1, wherein said human subject has hypophosphatasia (HPP) or is at risk of developing HPP.

\* \* \* \* \*